United States Patent
He et al.

(10) Patent No.: US 10,501,446 B2
(45) Date of Patent: *Dec. 10, 2019

(54) PHOTOCHROMIC COMPOUNDS

(71) Applicant: Transitions Optical, Inc., Pinellas Park, FL (US)

(72) Inventors: Meng He, Palm Harbor, FL (US); Darrin R. Dabideen, Monroeville, PA (US); Terry A. Kellar, II, Millbrae, CA (US); Anil Kumar, Murrysville, PA (US)

(73) Assignee: Transitions Optical, Inc., Pinellas Park, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/007,067

(22) Filed: Jun. 13, 2018

(65) Prior Publication Data

US 2018/0291007 A1    Oct. 11, 2018

Related U.S. Application Data

(60) Division of application No. 15/219,434, filed on Jul. 26, 2016, now Pat. No. 10,000,472, which is a division of application No. 14/174,978, filed on Feb. 7, 2014, now Pat. No. 9,405,041, which is a division of application No. 13/452,030, filed on Apr. 20, 2012, now Pat. No. 8,705,160, which is a division of application No. 12/329,092, filed on Dec. 5, 2008, now Pat. No. 8,211,338, which is a continuation-in-part of application No. 10/846,629, filed on May 17, 2004, now Pat. No. 7,342,112.

(60) Provisional application No. 60/484,100, filed on Jul. 1, 2003.

(51) Int. Cl.
| | |
|---|---|
| C07D 405/10 | (2006.01) |
| G02C 7/10 | (2006.01) |
| G02B 1/04 | (2006.01) |
| G03C 1/73 | (2006.01) |
| G03C 1/685 | (2006.01) |
| G02B 5/30 | (2006.01) |
| C09K 9/02 | (2006.01) |
| C07D 311/92 | (2006.01) |
| C07D 311/94 | (2006.01) |
| G02B 5/22 | (2006.01) |
| G02B 5/23 | (2006.01) |

(52) U.S. Cl.
CPC .......... *C07D 405/10* (2013.01); *C07D 311/92* (2013.01); *C07D 311/94* (2013.01); *C09K 9/02* (2013.01); *G02B 1/04* (2013.01); *G02B 5/223* (2013.01); *G02B 5/23* (2013.01); *G02B 5/3016* (2013.01); *G02C 7/102* (2013.01); *G03C 1/685* (2013.01); *G03C 1/73* (2013.01); *C09K 2211/1011* (2013.01); *C09K 2211/1029* (2013.01); *C09K 2211/1033* (2013.01); *C09K 2211/1088* (2013.01); *Y10T 428/31507* (2015.04); *Y10T 428/31551* (2015.04); *Y10T 428/31663* (2015.04); *Y10T 428/31786* (2015.04); *Y10T 428/31938* (2015.04)

(58) Field of Classification Search
None
See application file for complete search history.

(56) References Cited

U.S. PATENT DOCUMENTS

| | | |
|---|---|---|
| 303,673 A | 8/1884 | Small |
| 2,319,826 A | 5/1943 | Pellett |
| 2,334,446 A | 11/1943 | Serrell |
| 2,475,921 A | 7/1949 | Smith |
| 2,481,830 A | 9/1949 | Dreyer |
| 2,544,659 A | 3/1951 | Dreyer |
| 3,276,316 A | 10/1966 | Makas |
| 3,361,706 A | 1/1968 | Meriwether et al. |
| 3,562,172 A | 2/1971 | Ono et al. |

(Continued)

FOREIGN PATENT DOCUMENTS

| | | |
|---|---|---|
| CA | 2034316 A1 | 7/1991 |
| CA | 2549471 A1 | 7/2005 |

(Continued)

OTHER PUBLICATIONS

Chatterjea, "Syntheses of furano compounds. IX. A synthesis of alpha-brazan and the related quinone", Journal of the Indian Chemical Society, 1956, pp. 447-454, vol. 33, (Abstract Only).

Araujo et al.; "Photochromism"; Techniques in Chemistry; 1971; pp. 734-853; vol. III; Chapter 3; Glenn H. Brown; Editor, Wiley-Interscience a Division of John Wiley & Sons, Inc.

Atassi et al.; "Reversible photoinduced modifications of polymers doped with photochromes: anisotropy, photo-assisted poling and surface gratings."; Mol. Cryst. Liq. Cryst.; 1998; pp. 11-22; vol. 315.

(Continued)

*Primary Examiner* — Kamal A Saeed
(74) *Attorney, Agent, or Firm* — The Webb Law Firm

(57) ABSTRACT

A photochromic compound is provided, which may be a pyran, an oxazine, or a fulgide. The photochromic compound has at least one substituent Q attached thereto, each Q independently being —$N_3$, —CN, —COOR', —CCR', —C(R')C(R')R', —OCOR', —OCOOR', —SR', —$OSO_2R'''$, and/or —CON(R')R', wherein each R' is hydrogen, an unsubstituted or substituted alkyl group having from 1 to 18 carbon atoms; an unsubstituted or substituted aryl group, an unsubstituted or substituted alkene or alkyne group having from 2 to 18 carbon atoms, wherein the substituents are halo or hydroxyl and R''' is —$CF_3$ or a perfluorinated alkyl group having from 2 to 18 carbon atoms The number, locations and nature of the constituents Q are dependent upon the structure of the photochromic compound.

14 Claims, 6 Drawing Sheets

(56) References Cited

U.S. PATENT DOCUMENTS

| | | |
|---|---|---|
| 3,567,605 A | 3/1971 | Becker |
| 3,578,602 A | 5/1971 | Ono et al. |
| 3,653,863 A | 4/1972 | Araujo et al. |
| 4,039,254 A | 8/1977 | Harsch |
| 4,043,637 A | 8/1977 | Hovey |
| 4,049,338 A | 9/1977 | Slocum |
| 4,166,043 A | 8/1979 | Uhlmann et al. |
| 4,190,330 A | 2/1980 | Berreman |
| 4,215,010 A | 7/1980 | Hovey et al. |
| 4,279,474 A | 7/1981 | Belgorod |
| 4,342,668 A | 8/1982 | Hovey et al. |
| 4,367,170 A | 1/1983 | Uhlmann et al. |
| 4,539,048 A | 9/1985 | Cohen |
| 4,539,049 A | 9/1985 | Cohen |
| 4,549,894 A | 10/1985 | Araujo et al. |
| 4,556,605 A | 12/1985 | Mogami et al. |
| 4,637,698 A | 1/1987 | Kwak et al. |
| 4,637,896 A | 1/1987 | Shannon |
| 4,648,925 A | 3/1987 | Goepfert et al. |
| 4,650,526 A | 3/1987 | Claffey et al. |
| 4,683,153 A | 7/1987 | Goepfert et al. |
| 4,685,783 A | 8/1987 | Heller et al. |
| 4,720,356 A | 1/1988 | Chu |
| 4,728,173 A | 3/1988 | Toth |
| 4,756,605 A | 7/1988 | Okada et al. |
| 4,756,973 A | 7/1988 | Sakagami et al. |
| 4,785,097 A | 11/1988 | Kwak |
| 4,810,433 A | 3/1989 | Takayanagi et al. |
| 4,816,584 A | 3/1989 | Kwak et al. |
| 4,818,096 A | 4/1989 | Heller et al. |
| 4,826,977 A | 5/1989 | Heller et al. |
| 4,838,673 A | 6/1989 | Richards et al. |
| 4,863,763 A | 9/1989 | Takeda et al. |
| 4,865,668 A | 9/1989 | Goepfert et al. |
| 4,873,026 A | 10/1989 | Behre et al. |
| 4,873,029 A | 10/1989 | Blum |
| 4,880,667 A | 11/1989 | Welch |
| 4,929,693 A | 5/1990 | Akashi et al. |
| 4,931,219 A | 6/1990 | Kwiatkowski et al. |
| 4,931,220 A | 6/1990 | Haynes et al. |
| 4,931,221 A | 6/1990 | Heller |
| 4,959,471 A | 9/1990 | Melzig |
| 4,962,013 A | 10/1990 | Tateoka et al. |
| 4,974,941 A | 12/1990 | Gibbons et al. |
| 4,977,028 A | 12/1990 | Goepfert et al. |
| 4,983,479 A | 1/1991 | Broer et al. |
| 5,024,850 A | 6/1991 | Broer et al. |
| 5,053,302 A | 10/1991 | Makino et al. |
| 5,066,818 A | 11/1991 | Gemert et al. |
| 5,067,795 A | 11/1991 | Senatore |
| 5,073,294 A | 12/1991 | Shannon et al. |
| 5,130,058 A | 7/1992 | Tanaka et al. |
| 5,130,353 A | 7/1992 | Fischer et al. |
| 5,139,707 A | 8/1992 | Guglielmetti et al. |
| 5,155,607 A | 10/1992 | Inoue et al. |
| 5,166,345 A | 11/1992 | Akashi et al. |
| 5,177,227 A | 1/1993 | Fischer et al. |
| 5,180,470 A | 1/1993 | Smith et al. |
| 5,180,524 A | 1/1993 | Casilli et al. |
| 5,185,390 A | 2/1993 | Fischer et al. |
| 5,186,867 A | 2/1993 | Castaldi et al. |
| 5,189,448 A | 2/1993 | Yaguchi |
| 5,194,973 A | 3/1993 | Isogai et al. |
| 5,200,116 A | 4/1993 | Heller |
| 5,202,053 A | 4/1993 | Shannon |
| 5,204,850 A | 4/1993 | Obata |
| 5,238,931 A | 8/1993 | Yoshikawa et al. |
| 5,238,981 A | 8/1993 | Knowles |
| 5,247,377 A | 9/1993 | Omeis et al. |
| 5,274,132 A | 12/1993 | Van Gemert |
| 5,289,547 A | 2/1994 | Ligas et al. |
| 5,359,085 A | 10/1994 | Iwamoto et al. |
| 5,359,443 A | 10/1994 | Toyooka et al. |
| 5,384,077 A | 1/1995 | Knowles |
| 5,389,287 A | 2/1995 | Nishiyama et al. |
| 5,389,698 A | 2/1995 | Chigrinov et al. |
| 5,391,327 A | 2/1995 | Ligas et al. |
| 5,395,566 A | 3/1995 | Kobayakawa et al. |
| 5,405,958 A | 4/1995 | Van Gemert |
| 5,464,669 A | 11/1995 | Kang et al. |
| 5,466,398 A | 11/1995 | Van Gemert et al. |
| 5,543,267 A | 8/1996 | Stumpe et al. |
| 5,543,533 A | 8/1996 | Allegrini et al. |
| 5,602,661 A | 2/1997 | Schadt et al. |
| 5,608,567 A | 3/1997 | Grupp |
| 5,641,846 A | 6/1997 | Bieringer et al. |
| 5,644,416 A | 7/1997 | Morikawa et al. |
| 5,645,767 A | 7/1997 | Van Gemert |
| 5,658,501 A | 8/1997 | Kumar et al. |
| 5,698,141 A | 12/1997 | Kumar |
| 5,707,557 A | 1/1998 | Melzig et al. |
| 5,723,072 A | 3/1998 | Kumar |
| 5,744,070 A | 4/1998 | Kumar |
| 5,746,949 A | 5/1998 | Shen et al. |
| 5,770,115 A | 6/1998 | Misura |
| 5,808,100 A | 9/1998 | Momoda et al. |
| 5,831,090 A | 11/1998 | Paltchkov et al. |
| 5,846,452 A | 12/1998 | Gibbons et al. |
| 5,869,658 A | 2/1999 | Lin et al. |
| 5,903,330 A | 5/1999 | Funfschilling et al. |
| 5,943,104 A | 8/1999 | Moddel et al. |
| 5,952,515 A | 9/1999 | Melzig et al. |
| 5,955,520 A | 9/1999 | Heller et al. |
| 5,961,892 A | 10/1999 | Gemert et al. |
| 5,962,617 A | 10/1999 | Slagel |
| 6,004,486 A | 12/1999 | Chan |
| 6,022,497 A | 2/2000 | Kumar |
| 6,025,026 A | 2/2000 | Smith et al. |
| 6,036,890 A | 3/2000 | Melzig et al. |
| 6,049,428 A | 4/2000 | Khan et al. |
| 6,060,001 A | 5/2000 | Welch et al. |
| 6,066,797 A | 5/2000 | Toyomura et al. |
| 6,080,338 A | 6/2000 | Kumar |
| 6,096,375 A | 8/2000 | Ouderkirk et al. |
| 6,106,744 A | 8/2000 | Van Gemert et al. |
| 6,113,814 A | 9/2000 | Gemert et al. |
| 6,136,968 A | 10/2000 | Chamontin et al. |
| 6,141,135 A | 10/2000 | Nagoh et al. |
| 6,146,554 A | 11/2000 | Melzig et al. |
| 6,150,430 A | 11/2000 | Walters et al. |
| 6,153,126 A | 11/2000 | Kumar |
| 6,160,597 A | 12/2000 | Schadt et al. |
| 6,177,032 B1 | 1/2001 | Smith et al. |
| 6,177,932 B1 | 1/2001 | Galdes et al. |
| 6,187,444 B1 | 2/2001 | Bowles, III et al. |
| 6,197,225 B1 | 3/2001 | Tanizawa et al. |
| 6,201,588 B1 | 3/2001 | Walton et al. |
| 6,208,393 B1 | 3/2001 | Bawolek et al. |
| 6,239,778 B1 | 5/2001 | Palffy-Muhoray et al. |
| 6,245,399 B1 | 6/2001 | Sahouani et al. |
| 6,256,152 B1 | 7/2001 | Coldrey et al. |
| 6,268,055 B1 | 7/2001 | Walters et al. |
| 6,281,366 B1 | 8/2001 | Frigoli et al. |
| 6,284,418 B1 | 9/2001 | Trantolo |
| 6,294,112 B1 | 9/2001 | Clarke et al. |
| 6,296,785 B1 | 10/2001 | Nelson et al. |
| 6,303,673 B1 | 10/2001 | Clarke et al. |
| 6,312,811 B1 | 11/2001 | Frigoli et al. |
| 6,334,681 B1 | 1/2002 | Perrott et al. |
| 6,337,409 B1 | 1/2002 | Hughes et al. |
| 6,338,808 B1 | 1/2002 | Kawata et al. |
| 6,340,765 B1 | 1/2002 | Momoda et al. |
| 6,340,766 B1 | 1/2002 | Lin |
| 6,348,604 B1 | 2/2002 | Nelson et al. |
| 6,353,102 B1 | 3/2002 | Kumar |
| 6,369,869 B2 | 4/2002 | Schadt et al. |
| 6,432,544 B1 | 8/2002 | Stewart et al. |
| 6,433,043 B1 | 8/2002 | Misura et al. |
| 6,436,525 B1 | 8/2002 | Welch et al. |
| 6,474,695 B1 | 11/2002 | Schneider et al. |
| 6,491,990 B1 | 12/2002 | Parri et al. |
| 6,506,488 B1 | 1/2003 | Stewart et al. |
| 6,531,076 B2 | 3/2003 | Crano et al. |
| 6,555,028 B2 | 4/2003 | Walters et al. |

(56) References Cited

U.S. PATENT DOCUMENTS

| | | |
|---|---|---|
| 6,555,029 B1 | 4/2003 | Ruscio et al. |
| 6,579,422 B1 | 6/2003 | Kakinuma |
| 6,597,422 B1 | 7/2003 | Funfschilling et al. |
| 6,602,603 B2 | 8/2003 | Welch et al. |
| 6,613,433 B2 | 9/2003 | Yamamoto et al. |
| 6,630,597 B1 | 10/2003 | Lin et al. |
| 6,641,874 B2 | 11/2003 | Kuntz et al. |
| 6,660,727 B1 | 12/2003 | Mann et al. |
| 6,683,709 B2 | 1/2004 | Mann et al. |
| 6,690,495 B1 | 2/2004 | Kosa et al. |
| 6,705,569 B1 | 3/2004 | Sanders et al. |
| 6,717,644 B2 | 4/2004 | Schadt et al. |
| 6,723,859 B2 | 4/2004 | Kawabata et al. |
| 6,736,998 B2 | 5/2004 | Petrovskaia et al. |
| 6,761,452 B2 | 7/2004 | Moravec et al. |
| 6,797,383 B2 | 9/2004 | Nishizawa et al. |
| 6,806,930 B2 | 10/2004 | Moia |
| 6,844,686 B1 | 1/2005 | Schneck et al. |
| 6,874,888 B1 | 4/2005 | Dudai |
| 6,891,038 B2 | 5/2005 | Krongauz et al. |
| 6,986,946 B2 | 1/2006 | Nishizawa et al. |
| 7,008,568 B2 | 3/2006 | Qin |
| 7,097,303 B2 | 8/2006 | Kumar et al. |
| 7,118,806 B2 | 10/2006 | Nishizawa et al. |
| 7,166,357 B2 | 1/2007 | Kumar et al. |
| 7,247,262 B2 | 7/2007 | Evans et al. |
| 7,256,921 B2 | 8/2007 | Kumar et al. |
| 7,262,295 B2 | 8/2007 | Walters et al. |
| 7,320,826 B2 | 1/2008 | Kumar et al. |
| 7,342,112 B2 | 3/2008 | Kumar et al. |
| 7,357,503 B2 | 4/2008 | Mosse et al. |
| 7,416,682 B2 | 8/2008 | Frigoli et al. |
| 7,465,415 B2 | 12/2008 | Wang et al. |
| 7,521,004 B2 | 4/2009 | Momoda et al. |
| 7,557,206 B2 | 7/2009 | Kumar et al. |
| 7,557,208 B2 | 7/2009 | Walters et al. |
| 7,560,124 B2 * | 7/2009 | Kumar .............. C07D 311/94 424/704 |
| 7,579,022 B2 | 8/2009 | Kumar et al. |
| 7,582,749 B2 | 9/2009 | Kumar et al. |
| 8,211,338 B2 * | 7/2012 | He ..................... C07D 311/92 252/586 |
| 8,545,984 B2 | 10/2013 | He et al. |
| 8,697,890 B2 | 4/2014 | Sukhomlinova et al. |
| 9,034,219 B2 | 5/2015 | He et al. |
| 2002/0039627 A1 | 4/2002 | Ichihashi et al. |
| 2002/0090516 A1 | 7/2002 | Loshak et al. |
| 2002/0167639 A1 | 11/2002 | Coates et al. |
| 2002/0180916 A1 | 12/2002 | Schadt et al. |
| 2003/0008958 A1 | 1/2003 | Momoda et al. |
| 2003/0045612 A1 | 3/2003 | Misura et al. |
| 2003/0189684 A1 | 10/2003 | Kuntz et al. |
| 2004/0046927 A1 | 3/2004 | Montgomery |
| 2004/0068071 A1 | 4/2004 | Hoff et al. |
| 2004/0090570 A1 | 5/2004 | Kosa et al. |
| 2004/0125337 A1 | 7/2004 | Boulineau et al. |
| 2004/0158028 A1 | 8/2004 | Buhler |
| 2004/0185255 A1 | 9/2004 | Walters et al. |
| 2004/0185268 A1 | 9/2004 | Kumar et al. |
| 2004/0186241 A1 | 9/2004 | Gemert |
| 2004/0191520 A1 | 9/2004 | Kumar et al. |
| 2004/0207809 A1 | 10/2004 | Blackburn et al. |
| 2004/0223221 A1 | 11/2004 | Sugimura et al. |
| 2004/0228817 A1 | 11/2004 | Simon et al. |
| 2004/0228818 A1 | 11/2004 | Simon et al. |
| 2005/0003107 A1 | 1/2005 | Kumar et al. |
| 2005/0004361 A1 | 1/2005 | Kumar et al. |
| 2005/0012998 A1 | 1/2005 | Kumar et al. |
| 2005/0146680 A1 | 7/2005 | Muisener et al. |
| 2005/0151926 A1 | 7/2005 | Kumar et al. |
| 2005/0202267 A1 | 9/2005 | Ha et al. |
| 2005/0276767 A1 | 12/2005 | Blin et al. |
| 2006/0022176 A1 | 2/2006 | Wang et al. |
| 2007/0041073 A1 | 2/2007 | Kumar et al. |
| 2007/0131362 A1 | 6/2007 | Buchert et al. |
| 2007/0188698 A1 | 8/2007 | Mosse et al. |
| 2007/0275234 A1 | 11/2007 | Lim et al. |
| 2009/0309076 A1 | 12/2009 | He et al. |
| 2009/0323011 A1 | 12/2009 | He et al. |
| 2010/0014010 A1 | 1/2010 | He et al. |
| 2011/0129678 A1 | 6/2011 | He et al. |
| 2011/0140056 A1 | 6/2011 | He et al. |
| 2011/0143141 A1 | 6/2011 | He et al. |

FOREIGN PATENT DOCUMENTS

| | | |
|---|---|---|
| EP | 0313941 A1 | 5/1989 |
| EP | 0315224 A1 | 5/1989 |
| EP | 0321563 A1 | 6/1989 |
| EP | 0331233 A2 | 9/1989 |
| EP | 0336193 A2 | 10/1989 |
| EP | 0397263 A1 | 11/1990 |
| EP | 0442166 A1 | 8/1991 |
| EP | 0446717 A2 | 9/1991 |
| EP | 0488164 A2 | 6/1992 |
| EP | 0543678 A1 | 5/1993 |
| EP | 0619358 A1 | 10/1994 |
| EP | 0686685 B1 | 12/1995 |
| EP | 0686686 A1 | 12/1995 |
| EP | 0770116 A1 | 5/1997 |
| EP | 0772069 A1 | 5/1997 |
| EP | 0926146 A1 | 6/1999 |
| EP | 0965626 A1 | 12/1999 |
| EP | 0965628 A1 | 12/1999 |
| EP | 1044979 A2 | 10/2000 |
| EP | 1162482 A2 | 12/2001 |
| EP | 1184379 A1 | 3/2002 |
| EP | 1203967 A1 | 5/2002 |
| EP | 1394595 A1 | 3/2004 |
| EP | 1674460 A1 | 6/2006 |
| GB | 583842 | 1/1947 |
| GB | 2169417 A | 7/1986 |
| GB | 2189417 A | 10/1987 |
| JP | 59135428 A | 8/1984 |
| JP | 63175094 A | 7/1988 |
| JP | 63234084 A | 9/1988 |
| JP | 63250381 A | 10/1988 |
| JP | 63250382 A | 10/1988 |
| JP | 63275587 A | 11/1988 |
| JP | 6430744 A | 2/1989 |
| JP | 6490286 A | 4/1989 |
| JP | 1170904 A | 7/1989 |
| JP | 1258681 A | 10/1989 |
| JP | 280490 A | 3/1990 |
| JP | 2101080 A | 4/1990 |
| JP | 2194084 A | 7/1990 |
| JP | 2243694 A | 9/1990 |
| JP | 366692 A | 3/1991 |
| JP | 3137634 A | 6/1991 |
| JP | 3200118 A | 9/1991 |
| JP | 3200218 A | 9/1991 |
| JP | 3221563 A | 9/1991 |
| JP | 3227986 A | 10/1991 |
| JP | 3227988 A | 10/1991 |
| JP | 4117387 A | 4/1992 |
| JP | 4358117 A | 12/1992 |
| JP | 6214195 A | 8/1994 |
| JP | 6295687 A | 10/1994 |
| JP | 6306354 A | 11/1994 |
| JP | 741758 A | 2/1995 |
| JP | 762337 A | 3/1995 |
| JP | 7165762 A | 6/1995 |
| JP | 827155 A | 1/1996 |
| JP | 827461 A | 1/1996 |
| JP | 8157467 A | 6/1996 |
| JP | 8176139 A | 7/1996 |
| JP | 8209119 A | 8/1996 |
| JP | 8295690 A | 11/1996 |
| JP | 973149 A | 3/1997 |
| JP | 9124645 A | 5/1997 |
| JP | 11322739 A | 11/1999 |
| JP | 2001114775 A | 4/2001 |
| JP | 2001192378 A | 7/2001 |
| JP | 2002194084 A | 7/2002 |

(56) References Cited

FOREIGN PATENT DOCUMENTS

| | | | |
|---|---|---|---|
| JP | 2005112772 A | 4/2005 | |
| JP | 2005187420 A | 7/2005 | |
| WO | 8905464 A1 | 6/1989 | |
| WO | 8911674 A1 | 11/1989 | |
| WO | 9201959 A1 | 2/1992 | |
| WO | 9310112 A1 | 5/1993 | |
| WO | 9317071 A1 | 9/1993 | |
| WO | 9601684 A1 | 1/1996 | |
| WO | 9601884 A1 | 1/1996 | |
| WO | 9705213 A1 | 2/1997 | |
| WO | 9706455 A1 | 2/1997 | |
| WO | 9710241 A1 | 3/1997 | |
| WO | 9722894 A | 6/1997 | |
| WO | 9819207 A1 | 5/1998 | |
| WO | 9920630 A1 | 4/1999 | |
| WO | 9943666 A1 | 9/1999 | |
| WO | 0015630 A1 | 3/2000 | |
| WO | 0019252 A1 | 4/2000 | |
| WO | 0035902 A1 | 6/2000 | |
| WO | 0077559 A1 | 12/2000 | |
| WO | 0102449 A2 | 1/2001 | |
| WO | 0119813 A1 | 3/2001 | |
| WO | 0155960 A1 | 8/2001 | |
| WO | 0170719 A2 | 9/2001 | |
| WO | 0177122 A2 | 10/2001 | |
| WO | 0229489 A2 | 4/2002 | |
| WO | 02058921 A1 | 8/2002 | |
| WO | 03019270 A1 | 3/2003 | |
| WO | 03032066 A1 | 4/2003 | |
| WO | 2004003107 A1 | 1/2004 | |
| WO | 2004011964 A1 | 2/2004 | |
| WO | 2004041961 A1 | 5/2004 | |
| WO | 2005005570 A1 | 1/2005 | |
| WO | 2005084826 A1 | 9/2005 | |
| WO | 2005085912 A1 | 9/2005 | |
| WO | 2006060683 A2 | 6/2006 | |
| WO | 2008051420 A2 | 5/2008 | |
| WO | 2010065393 A1 | 6/2010 | |

OTHER PUBLICATIONS

Bachels et al.; "Novel Photo-Aligned LC-Polmer Wide-View Film for TN Displays"; Eurodisplay; 2002; pp. 183-186.

Castellano; "Surface Anchoring of Liquid Crystal Molecules on Various Substrates"; Mol. Cryst. Liq. Cryst.; 1983; pp. 33-41; vol. 94.

Chigrinov et al.; "New results on liquid crystal alignment by photopolymerization"; Proceedings of the SPIE—The Internationali Society for Optical Engineering, SPIE; 1995; pp. 130-140; vol. 2409.

"Choleric filters and films"; http://web.archive.org/web/20040325025143/http://rolic.com/050application/05223content.htm; Aug. 25, 2004.

Dyadyusha et al.; "Light-Induced Planar Orientation of a Nematic Liquid Crystal on an Anisotropic Surface Without Microrelief"; Ukr. fiz. zhurn; 1991; pp. 1059-1062; vol. 36:7.

Furrow et al.; "Practical Procedures for the Preparation of N-tert-Butyldimethylsilylhydrazones and Their Use in Modified Wolff-Kishner Reductions and in the Synthesis of Vinyl Halides and gem-Dihalides"; J. Am. Chem. Soc.; 2004; pp. 5436-5445; vol. 126.

Hattori et al.; "Facile Construction of the 1-Phenylnaphthyl Skeleton via an Ester-mediated Nucleophilic Aromatic Substitution Reaction. Applications to the Synthesis of Phenylnaphthalide Lignans"; J. Chem. Soc. Perkin Trans.; 1995; pp. 235-241.

Hattori et al.; "Practical Synthesis of 4'-Methylbiphenyl-2-carboxylic Acid"; Synthesis; 1995; pp. 41-43.

Hikmet et al.; "Gel layers for inducing adjustable pretilt angles in liquid crystal systems"; J. Appl. Phys.; 1991; pp. 1265-1269; vol. 70:3.

Huang et al.; "Effect of aligning layer thickness on photo-aligned ferroelectric liquid crystal displays"; Proceedings of the 6th Chinese Optoelectronics Symposium; Hong Kong, China; IEEE; (New York); 2003; pp. 231-234.

Ishihara et al.; "Regioselective Friedel-Crafts Acylation of 1,2,3,4-Tetrahydroquinoline and Related Nitrogen Heterocycles: Effects of NH Protective Groups and Ring Size"; J. Chem. Soc. Perkin Trans.; 1992, pp. 3401-3406.

Ishiyama et al.; "Palladium (0)-Catalyzed Cross-Coupling Reaction of Alkoxydiboron with Haloarenes: A Direct Procedure for Arylboronic Esters"; J. Org. Chem.; 1995; pp. 7508-7510; vol. 60.

Kozenkov et al.; "Photoanisotropic Effects in Poly (Vinyl-Cinnamate) Derivatives and Their Applications"; Mol. Cryst. Liq. Cryst.; 2004; pp. 251-267; vol. 409.

Kvasnikov et al.; "Birefringence in Polyvinylcinnamate Films Induced by Polarized Light"; Doklady Akademii nauk SSSR; 1977; pp. 633-636; vol. 237:3.

Moia et al.; "Optical LLP/LCD Devices: A new Generation of Optical Security Elements"; Proceedings of SPIE: Optical Security and Counterfeit Deterrence, Techniques III; Jan. 27-28, 2000; pp. 196-203; vol. 3973; San Jose, California.

Moia; "New coloured optical security elements using Rolic's LLP/LCP technology: devices for 1st to 3rd level inspection"; Proceedings of SPIE: Optical Security and Counterfeit Deterrence Techniques IV; Jan. 23-25, 2002; pp. 194-202; vol. 4677; San Jose, California.

Olah; "Friedel-Crafts and Related Reactions"; Interscience Publishers; 1964; pp. 1 vol. 3; Chapter XXXI (Aromatic Ketone Synthesis).

"Polymerization" in Hawley's Condensed Chemical Dictionary Thirteenth Edition; 1997; pp. 901-902; published by John Wiley & Sons, Inc., revised by Richard J. Lewis, Sr.

Schadt; "Liquid Crystal Displays and Novel Optical Thin Films Enabled by Photo-Alignment"; Mol. Cryst. and Liq. Cryst.; 2001; pp. 151-169; vol. 364.

Schadt; "Optics and Applications of Photo-Aligned Liquid Crystalline Surfaces"; Nonlinear Optics; 2000; pp. 1-12; vol. 25.

Schadt et al.; "Surface-Induced Parallel Alignment of Liquid Crystals by Lineraly Polymerized Photopolymers"; Jpn. J. Appl. Phys.; 1992; pp. 2155-2164; vol. 31.

Seiberle et al.; "Invited Paper: Photo-Aligned Anisotropic Optical Thin Films"; SID 03 Digest, Society of Information Displays; 2003; pp. 1162-1165.

Wang et al.; "Addition of Grignard Reagents to Aryl Acid Chlorides: An Efficient Synthesis of Aryl Ketones"; Organic Letters; 2005; pp. 5593-5595; vol. 7:25.

Chen et al., "Claisen rearrangement/Baylis-Hillman reaction/ring-closing metathesis as bases for the construction of substituted cyanonaphthalenes", Tetrahedron, 2007, p. 2824-2828, vol. 63.

Flett, "Intensities of some group characteristic infra-red bands", Spectrochimica Acta, 1962, pp. 1537-1556, vol. 18.

Kramer et al., "Development of a Selective Enzyme-Linked Immunosorbent Assay for 1-Naphthol—the Major Metabolite of Carbaryl (1-Naphthyl N-Methylcarbamate)", Journal of Agricultural Food Chemistry, 1994, pp. 934-943, vol. 42.

* cited by examiner

PHOTOCHROMIC COMPOUNDS

CROSS-REFERENCE TO RELATED APPLICATIONS

This application is a divisional of U.S. patent application Ser. No 15/219,434, filed Jul. 26, 2016, which is a divisional of U.S. patent application Ser. No. 14/174,978, filed Feb. 7, 2014, now U.S. Pat. No. 9,405,041 B2, which is a divisional of U.S. patent application Ser. No. 13/452,030, filed Apr. 20, 2012, now U.S. Pat. No. 8,705,160 B2, which is a divisional of U.S. patent application Ser. No. 12/329,092, filed Dec. 5, 2008, now U.S. Pat. No. 8,211,338 B2, which is a continuation-in-part of U.S. patent application Ser. No. 10/846,629, filed May 17, 2004, now U.S. Pat. No. 7,342,112 B2, which claims the benefit of U.S. Provisional Application No. 60/484,100, filed Jul. 1, 2003, all of which are hereby specifically incorporated by reference.

STATEMENT REGARDING FEDERALLY SPONSORED RESEARCH OR DEVELOPMENT

Not applicable.

REFERENCE TO A SEQUENCE LISTING

Not applicable.

BACKGROUND

Various non-limiting embodiments disclosed herein relate generally to photochromic compounds. Other non-limiting embodiments relate to devices and elements made using the photochromic compounds disclosed herein.

Conventional photochromic compounds have at least two states, a first state having a first absorption spectrum and a second state having a second absorption spectrum that differs from the first absorption spectrum, and are capable of switching between the two states in response to at least actinic radiation. Further, conventional photochromic compounds can be thermally reversible. That is, conventional photochromic compounds are capable of switching between a first state and a second state in response to at least actinic radiation and reverting back to the first state in response to thermal energy. As used herein "actinic radiation" means electromagnetic radiation, such as but not limited to ultraviolet and visible radiation that is capable of causing a response. More specifically, conventional photochromic compounds can undergo a transformation in response to actinic radiation from one isomer to another, with each isomer having a characteristic absorption spectrum, and can further revert back to the first isomer in response to thermal energy (i.e., be thermally reversible). For example, conventional thermally reversible photochromic compounds are generally capable of switching from a first state, for example a "clear state," to a second state, for example a "colored state," in response to actinic radiation and reverting back to the "clear" state in response to thermal energy.

Dichroic compounds are compounds that are capable of absorbing one of two orthogonal plane polarized components of transmitted radiation more strongly than the other. Thus, dichroic compounds are capable of linearly polarizing transmitted radiation. As used herein, "linearly polarize" means to confine the vibrations of the electric vector of light waves to one direction or plane. However, although dichroic materials are capable of preferentially absorbing one of two orthogonal plane polarized components of transmitted radiation, if the molecules of the dichroic compound are not suitably positioned or arranged, no net linear polarization of transmitted radiation will be achieved. That is, due to the random positioning of the molecules of the dichroic compound, selective absorption by the individual molecules will cancel each other such that no net or overall linear polarizing effect is achieved. Thus, it is generally necessary to suitably position or arrange the molecules of the dichroic compound within another material in order to form a conventional linear polarizing element, such as a linearly polarizing filter or lens for sunglasses.

In contrast to the dichroic compounds, it is generally not necessary to position or arrange the molecules of conventional photochromic compounds to form a conventional photochromic element. Thus, for example, conventional photochromic elements, such as lenses for photochromic eyewear, can be formed, for example, by spin coating a solution containing a conventional photochromic compound and a "host" material onto the surface of the lens, and suitably curing the resultant coating or layer without arranging the photochromic compound in any particular orientation. Further, even if the molecules of the conventional photochromic compound were suitably positioned or arranged as discussed above with respect to the dichroic compounds, because conventional photochromic compounds do not strongly demonstrate dichroism, elements made therefrom are generally not strongly linearly polarizing.

It would be advantageous to provide photochromic compounds that can exhibit useful photochromic and/or dichroic properties in at least one state, and that can be used in a variety of applications to impart photochromic and/or dichroic properties.

BRIEF DESCRIPTION OF THE SEVERAL VIEWS OF THE DRAWING(S)

Various non-limiting embodiments of the present invention will be better understood when read in conjunction with the drawings, in which.

Figure 3:
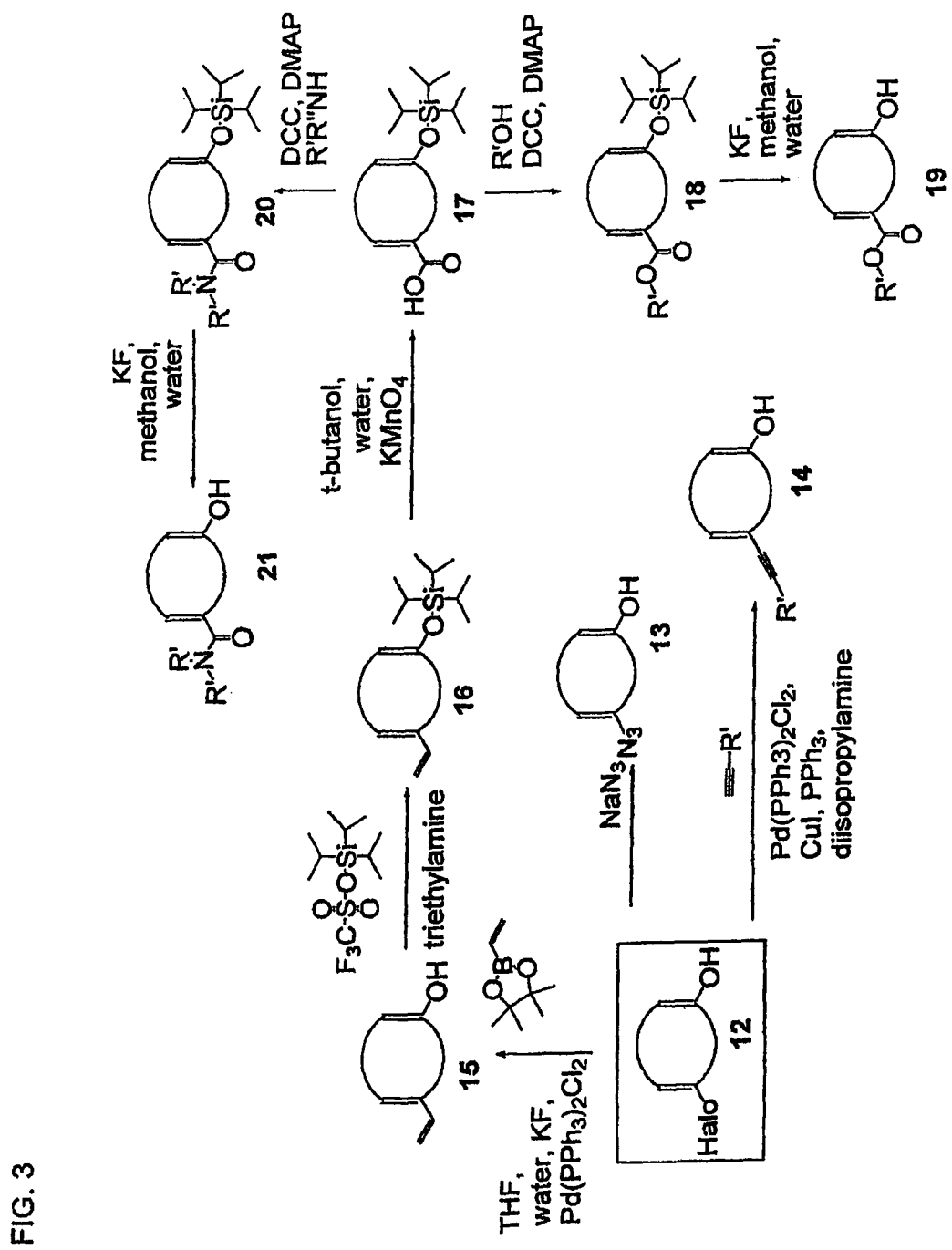
Figure 4:
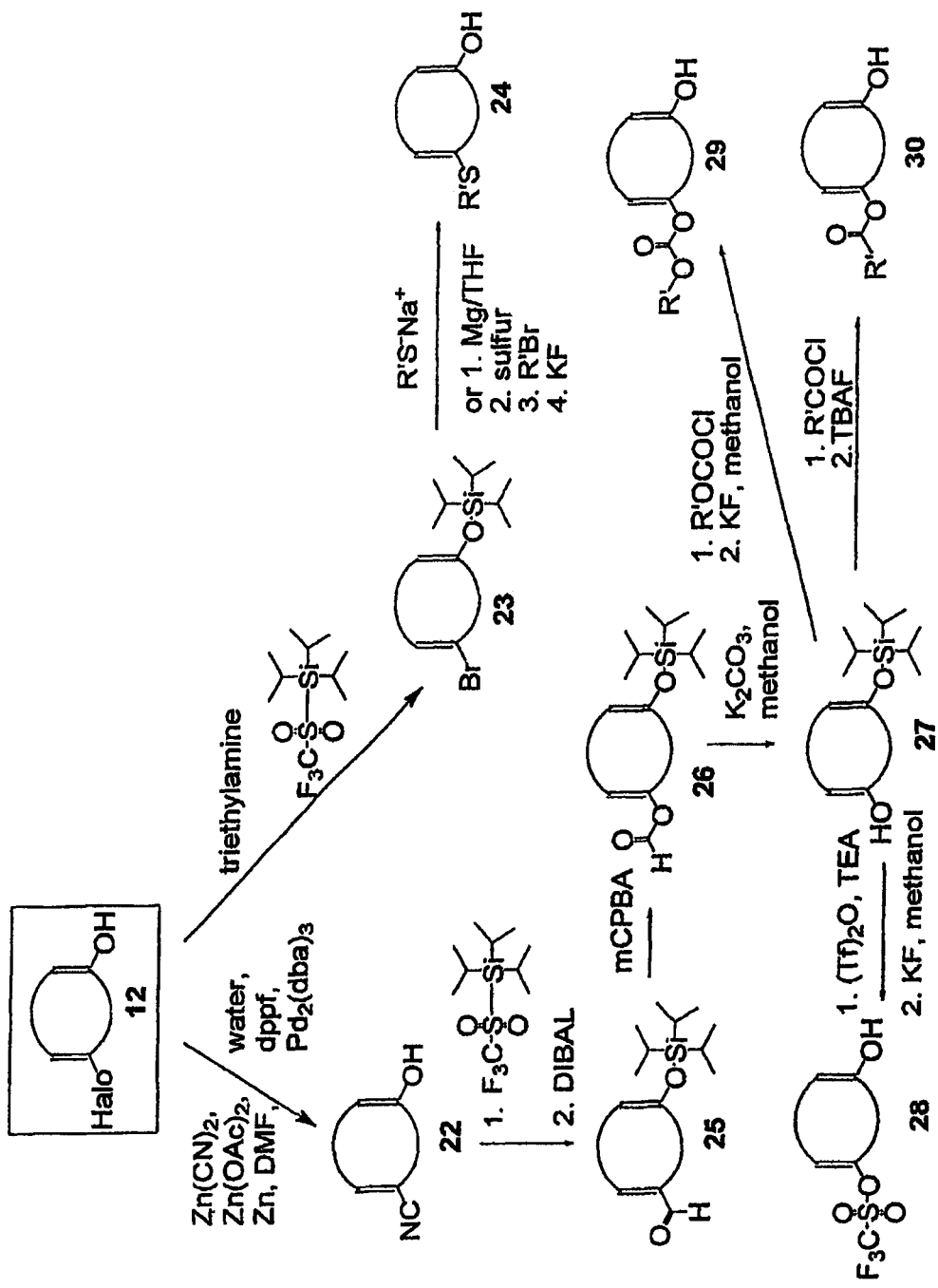

FIGS. 3 and 4 each show general reaction schemes for preparing naphthols having different Q groups according to the present invention.

Figure 5:
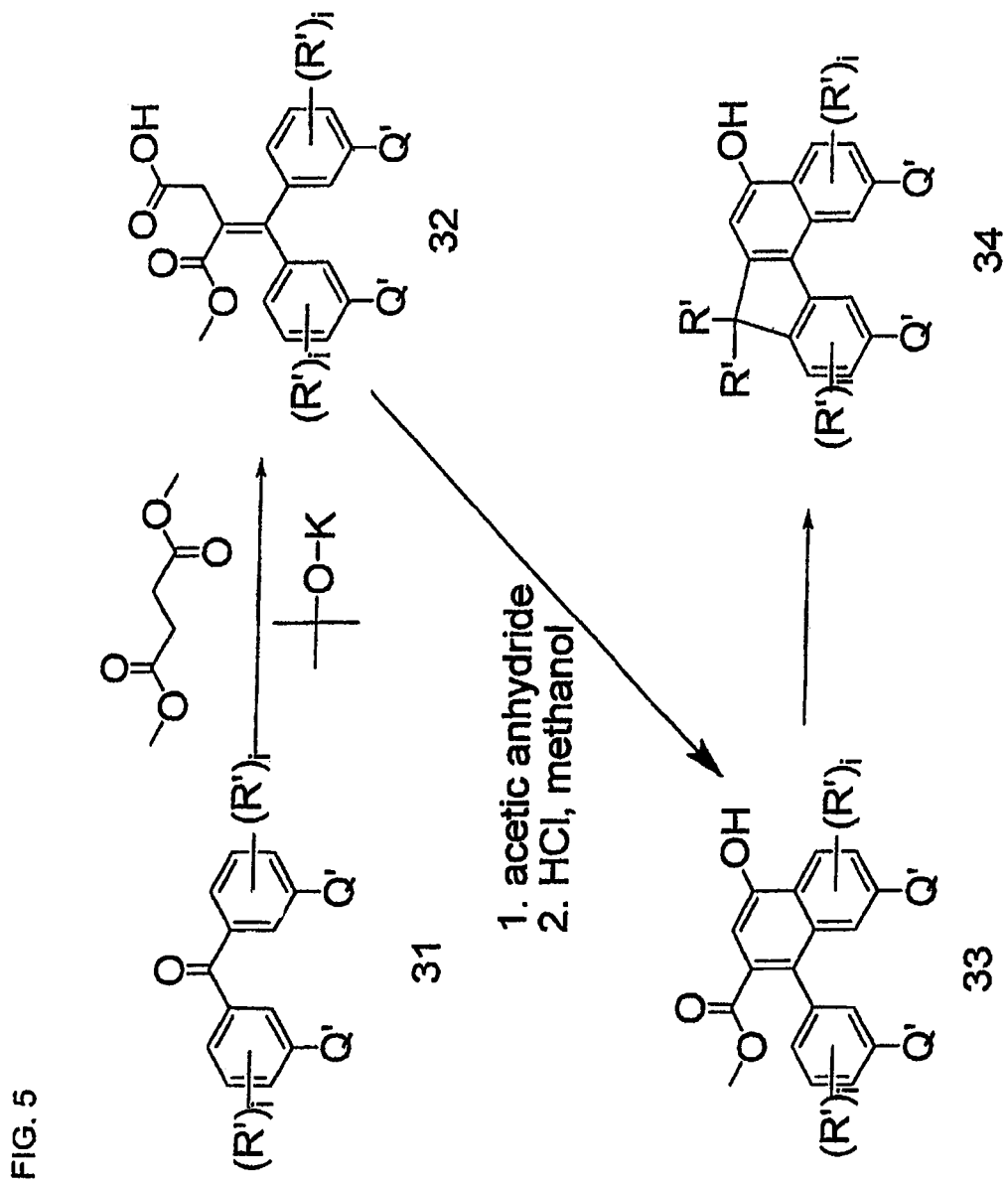

FIG. 5 shows a reaction scheme for preparing indeno-fused naphthols according to the present invention.

Figure 6:
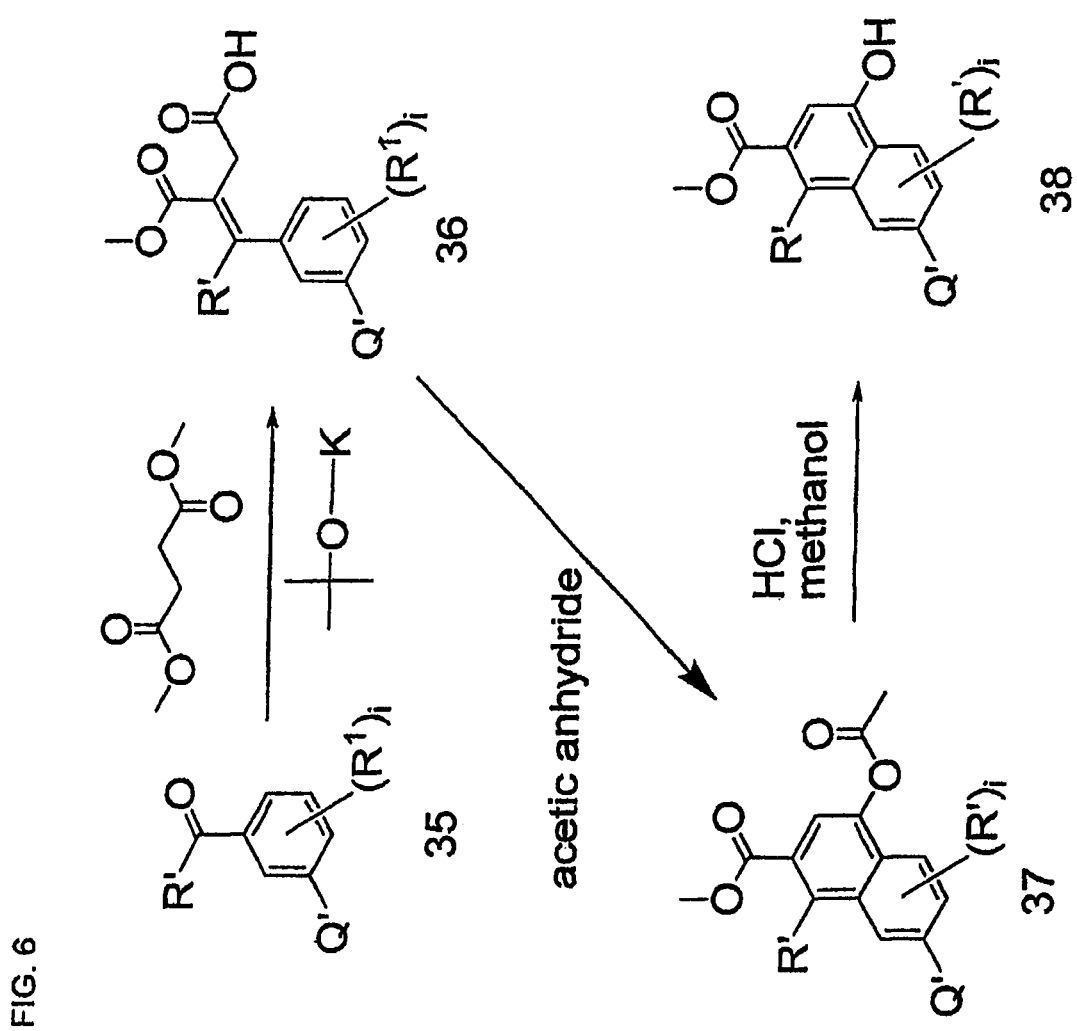

FIG. 6 shows a reaction scheme for preparing naphthols according to the present invention.

DETAILED DESCRIPTION

As used in this specification and the appended claims, the articles "a," "an," and "the" include plural referents unless expressly and unequivocally limited to one referent.

Additionally, for the purposes of this specification, unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Further, while the numerical ranges and parameters setting forth the broad scope of the invention are approximations as discussed above, the numerical values set forth in the Examples section are reported as precisely as possible. It should be understood, however, that such numerical values inherently contain certain errors resulting from the measurement equipment and/or measurement technique.

Various non-limiting embodiments of the invention will now be described. One non-limiting embodiment provides a thermally reversible, photochromic compound having a Q group at the position described hereinafter and optionally a Lengthening group L also described hereinafter. Another non-limiting embodiment provides a photochromic compound adapted to have at least a first state and a second state, wherein the thermally reversible, photochromic compound has an average absorption ratio greater than 2.3 in at least one state as determined according to the CELL METHOD, which is described in detail below. Further, according to various non-limiting embodiments, the thermally reversible, photochromic compound has an average absorption ratio greater than 2.3 in an activated state as determined according to the CELL METHOD. As used herein, the term "photochromic compound" (PC) includes thermally reversible photochromic compounds chosen from indeno[2',3'-3,4] naphtho[1,2-b]pyran, indeno[3',2'-3,4]naphtho[1,2-b]pyran, thiopheno[2',3'-3,4]naphtho[1,2-b]pyran, thiopheno[3',2'-3,4]naphtho[1,2-b]pyran, benzothiopheno[2',3'-3,4]naphtho[1,2-b]pyran, benzothiopheno[3',2'-3,4]naphtho[1,2-b]pyran, furo[2',3'-3,4]naphtho[1,2-b]pyran, furo[3',2'-3,4]naphtho[1,2-b]pyran, benzofuro[2',3'-3,4]naphtho[1,2-b]pyran, benzofuro[3',2'-3,4]naphtho[1,2-b]pyran, 2H-naphtho[1,2-b]pyran, 3H-naphtho[2,1-b]pyran, a benzopyran, a spiro[1,3-dihydroindole-3,3'-naphtho[2,1-b][1,4]] oxazine, a spiro[1,3-dihydroindole-2,2'-naphtho[1,2-b][1,4]]floxazine a fulgide and mixtures thereof. As used herein with respect to photochromic compounds, the term "activated state" refers to the photochromic compound when exposed to sufficient actinic radiation to cause the at least a portion of the photochromic compound to switch states. Further, as used herein the term "compound" means a substance formed by the union of two or more elements, components, ingredients, or parts and includes, without limitation, molecules and macromolecules (for example polymers or oligomers) formed by the union of two or more elements, components, ingredients, or parts.

Generally speaking, the CELL METHOD of measuring average absorption ratio of a photochromic compound involves obtaining an absorption spectrum for the photochromic compound, in an activated or unactived state, in each of two orthogonal polarization directions while the photochromic compound is at least partially aligned in an aligned liquid crystal medium that is contained within a cell assembly. More specifically, the cell assembly comprises two opposing glass substrates that are spaced apart by 20 microns+/−1 micron. The substrates are sealed along two opposite edges to form the cell. The inner surface of each of the glass substrates is coated with a polyimide coating, the surface of which has been at least partially ordered by rubbing. Alignment of the photochromic compound is achieved by introducing the photochromic compound and a liquid crystal medium into the cell assembly and allowing the liquid crystal medium to align with the rubbed polyimide surface. Because the photochromic compound is contained within the liquid crystal medium, alignment of the liquid crystal medium causes the photochromic compound to be aligned. It will be appreciated by those skilled in the art that the choice of the liquid crystal medium and the temperature used during testing can affect the measured absorption ratio. Accordingly, as set forth in more detail in the Examples, for purposes of the CELL METHOD, absorption ratio measurements are taken at room temperature (73° F.+/−0.5° F. or better) and the liquid crystal medium is Licristal® E7 (which is reported to be a mixture of cyanobiphenyl and cyanoterphenyl liquid crystal compounds).

Once the liquid crystal medium and the photochromic compound are aligned, the cell assembly is placed on an optical bench (which is described in more detail in the Examples). To obtain the average absorption ratio in the activated state, activation of the photochromic compound is achieved by exposing the photochromic compound to UV radiation for a time sufficient to reach a saturated or near saturated state (that is, a state wherein the absorption properties of the photochromic compound do not substantially change over the interval of time during which the measurements are made). Absorption measurements are taken over a period of time (typically 10 to 300 seconds) at 3 second intervals for light that is linearly polarized in a plane perpendicular to the optical bench (referred to as the 0° polarization plane or direction) and light that is linearly polarized in a plane that is parallel to the optical bench (referred to as the 90° polarization plane or direction) in the following sequence: 0°, 90°, 90°, 0° etc. The absorbance of the linearly polarized light by the cell is measured at each time interval for all of the wavelengths tested and the unactivated absorbance (i.e., the absorbance of the cell with the liquid crystal material and the unactivated photochromic compound) over the same range of wavelengths is subtracted to obtain absorption spectra for the photochromic compound in each of the 0° and 90° polarization planes to obtain an average difference absorption spectrum in each polarization plane for the photochromic compound in the saturated or near-saturated state.

Figure 1:
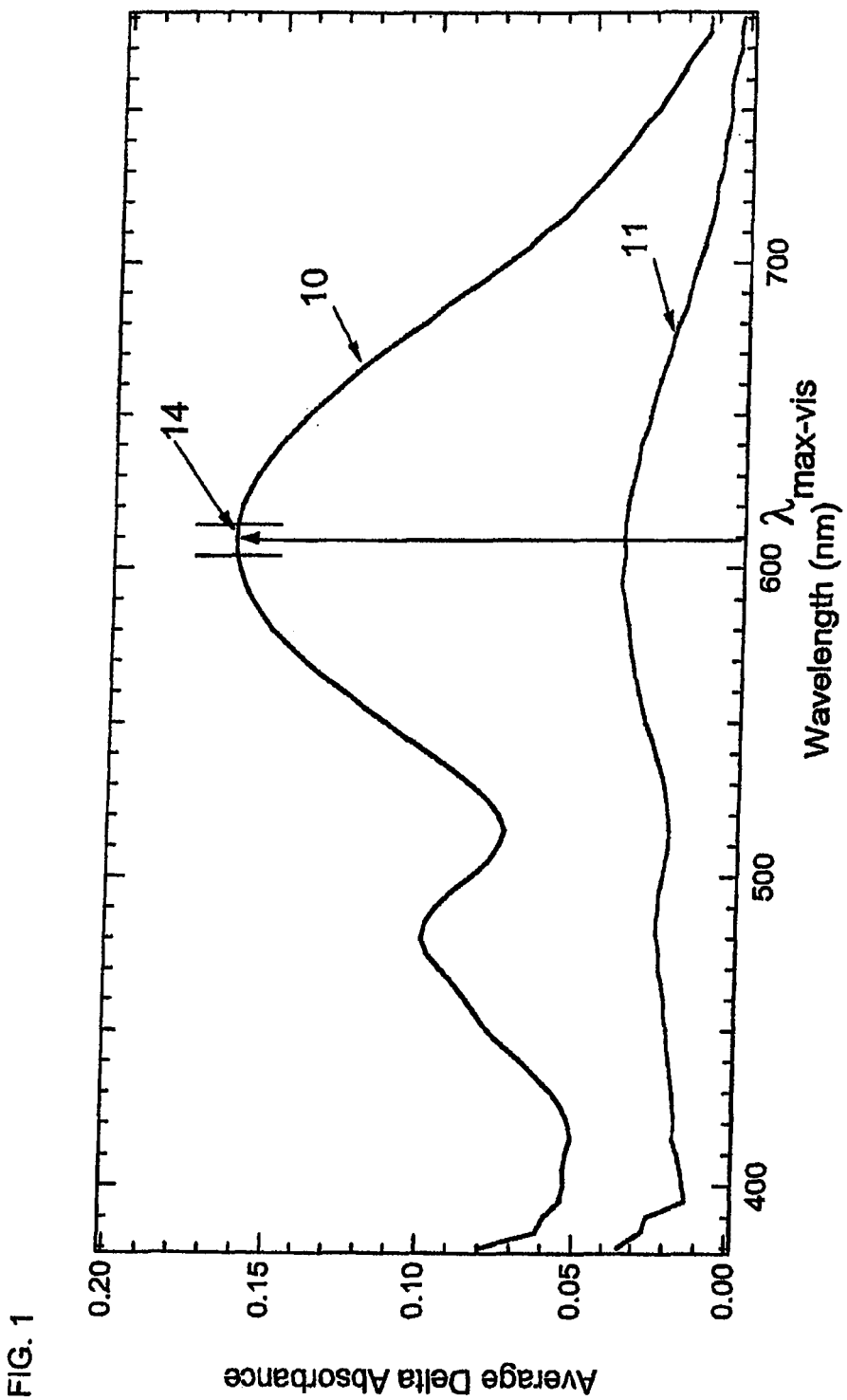
FIG. 1 shows two average difference absorption spectra obtained for a photochromic compound according to various non-limiting embodiments disclosed herein using the CELL METHOD.

For example, with reference to FIG. 1, there is shown the average difference absorption spectrum (generally indicated 10) in one polarization plane that was obtained for a photochromic compound according to one non-limiting embodiment disclosed herein. The average absorption spectrum (generally indicated 11) is the average difference absorption spectrum obtained for the same photochromic compound in the orthogonal polarization plane.

Based on the average difference absorption spectra obtained for the photochromic compound, the average absorption ratio for the photochromic compound is obtained as follows. The absorption ratio of the photochromic compound at each wavelength in a predetermined range of wavelengths corresponding to $\lambda_{max\text{-}vis}$+/−5 nanometers (generally indicated as 14 in FIG. 1), wherein $\lambda_{max\text{-}vis}$ is the wavelength at which the photochromic compound had the highest average absorbance in any plane, is calculated according to the following equation:

$$AR_{\lambda i}=Ab^1_{\lambda i}/Ab^2_{\lambda i} \qquad \text{Eq. 1}$$

wherein, $AR_{\lambda i}$ is the absorption ratio at wavelength $\lambda i$, $Ab^1_{\lambda i}$ is the average absorption at wavelength $\lambda i$ in the polarization direction (i.e., 0° or 90°) having the higher absorbance, and $Ab^2_{\lambda i}$ is the average absorption at wavelength $\lambda i$ in the remaining polarization direction. As previously discussed, the "absorption ratio" refers to the ratio of the absorbance of radiation linearly polarized in a first plane to the absorbance of the same wavelength radiation linearly polarized in a plane orthogonal to the first plane, wherein the first plane is taken as the plane with the highest absorbance.

The average absorption ratio ("AR") for the photochromic compound is then calculated by averaging the individual absorption ratios obtained for the wavelengths within the predetermined range of wavelengths (i.e., $\lambda_{max\text{-}vis}+/-5$ nanometers) according to the following equation:

$$AR=(\Sigma AR_{\lambda i})/n_i \qquad \text{Eq. 2}$$

wherein, AR is average absorption ratio for the photochromic compound, $AR_{\lambda i}$ are the individual absorption ratios (as determined above in Eq. 1) for each wavelength within the predetermined the range of wavelengths (i.e., $\lambda_{max\text{-}vis}+/-5$ nanometers), and $n_i$ is the number of individual absorption ratios averaged.

As previously discussed, conventional thermally reversible photochromic compounds are adapted to switch from a first state to a second state in response to actinic radiation, and to revert back to the first state in response to thermal energy. More specifically, conventional thermally reversible, photochromic compounds are capable of transforming from one isomeric form (for example and without limitation, a closed form) to another isomeric form (for example and without limitation, an open form) in response to actinic radiation, and reverting back to the closed form when exposed to thermal energy. However, as previously discussed, generally conventional thermally reversible photochromic compounds do not strongly demonstrate dichroism.

As discussed above, non-limiting embodiments disclosed herein provide a thermally reversible photochromic compound having an average absorption ratio greater than 2.3 in at least one state as determined according to CELL METHOD and/or a thermally reversible photochromic compound that can be used as an intermediate in the preparation of a photochromic compound having an absorption ratio greater than 2.3. Thus, the thermally reversible photochromic compound according to this non-limiting embodiment can display useful photochromic properties and/or useful photochromic and dichroic properties. That is, the thermally reversible, photochromic compound can be a thermally reversible, photochromic and/or photochromic-dichroic compound. As used herein with respect to the photochromic compounds described herein, the term "photochromic-dichroic" means displaying both photochromic and dichroic properties under certain conditions, which properties are at least detectable by instrumentation.

According to other non-limiting embodiments, the thermally reversible photochromic compounds can be thermally reversible photochromic-dichroic compounds having an average absorption ratio ranging from 4 to 20, from 3 to 30, or from 2.5 to 50 in at least one state as determined according to CELL METHOD. It will be appreciated by those skilled in the art that the higher the average absorption ratio of the photochromic compound the more linearly polarizing the photochromic compound will be. Therefore, according to various non-limiting embodiments, the thermally reversible photochromic compounds can have any average absorption ratio required to achieve a desired level of linear polarization.

Another non-limiting embodiment provides a thermally reversible, photochromic compound that is free of oxazines and adapted to have at least a first state and a second state, wherein the photochromic compound has an average absorption ratio of at least 1.5 in at least one state as determined according to CELL METHOD. Further, according to this non-limiting embodiment, the average average absorption ratio can range from 1.5 to 50 in at least one state as determined according to CELL METHOD.

In particular embodiments of the present invention, a photochromic material is provided comprising an indeno[2', 3'-3,4]naphtho[1,2-b]pyran, indeno[3',2'-3,4]naphtho[1,2-b]pyran, thiopheno[2',3'-3,4]naphtho[1,2-b]pyran, thiopheno[3',2'-3,4]naphtho[1,2-b]pyran, benzothiopheno[2',3'-3,4]naphtho[1,2-b]pyran, benzothiopheno[3',2'-3,4]naphtho[1,2-b]pyran, furo[2',3'-3,4]naphtho[1,2-b]pyran, furo[3',2'-3,4]naphtho[1,2-b]pyran, benzofuro[2',3'-3,4]naphtho[1,2-b]pyran, benzofuro[3',2'-3,4]naphtho[1,2-b]pyran, 2H-naphtho[1,2-b]pyran, 3H-naphtho[2,1-b]pyran, a benzopyran, a spiro[1,3-dihydroindole-3,3'-naphtho[2,1-b][1,4]]oxazine, a spiro[1,3-dihydroindole-2,2'-naphtho[1,2-b][1,4]]oxazine or a fulgide ; wherein:

(A) said photochromic material has at least one substituent Q attached thereto at the specific carbon atoms named hereinafter, each Q independently comprising —$N_3$, —CN, —COOR', —CCR', —C(R')C(R')R', —OCOR', —OCOOR', —SR', —$OSO_2R'''$, and/or —CON(R')R', wherein each R' independently comprises hydrogen, an unsubstituted or substituted alkyl group having from 1 to 18 carbon atoms, an unsubstituted or substituted aryl group, an unsubstituted or substituted alkene or alkyne group having from 2 to 18 carbon atoms, wherein said substituents are chosen from halo and hydroxyl and R''' comprises —$CF_3$ or a perfluorinated alkyl group having from 2 to 18 carbon atoms; provided wherein:

(a) when said photochromic material comprises an indeno[2',3'-3,4]naphtho[1,2-b]pyran, indeno[3',2'-3,4]naphtho[1,2-b]pyran, thiopheno[3',2'-3,4]naphtho[1,2-b]pyran, thiopheno[3',2'-3,4]naphtho[1,2-b]pyran, benzothiopheno[2',3'-3,4]naphtho[1,2-b]pyran, benzothiopheno[3',2'-3,4]naphtho[1,2-b]pyran, furo[2',3'-3,4]naphtho[1,2-b]pyran, furo[3',2'-3,4]naphtho[1,2-b]pyran, benzofuro[2',3'-3,4]naphtho[1,2-b]pyran, benzofuro[3',2'-3,4]naphtho[1,2-b]pyran, Q is attached thereto at the 7- and/or 10-positions and comprises —$N_3$, —COOR', —CCR', —C(R')C(R')R', —OCOR', —OCOOR', —SR', —$OSO_2R'''$ or —CN, provided that when said photochromic material is an indeno[2',3'-3,4]naphtho[1,2-b]pyran said material compound is substantially free of substituents at the 12-position;

(b) when said photochromic material comprises a 3H-naphtho[2,1--b]pyran, Q is attached thereto at the 6- and/or 7-positions and independently comprises for each occurrence, —$N_3$ or —OCOOR';

(c) when said photochromic material comprises a 2H-naphtho[1,2-b]pyran, Q is attached thereto at the 8-position and comprises —$N_3$; or —OCOOR', provided that said photochromic material is substantially free of substituents at the 5-position;

(d) when said photochromic material comprises a benzopyran, Q is attached thereto at the 7-position and comprises —$N_3$, —CN, —CCR', or —$OSO_2R'''$;

(e) when said photochromic material comprises a spiro[1,3-dihydroindole-2,2'-naphtho[1,2-b][1,4]]oxazine, substituents Q are attached thereto at the 5-, 6- and/or 8'-positions and independently comprise for each occurrence —$N_3$; —CCR', provided that the indolino group is substantially free of N-substituents; or —OSO₂R'", provided that said photochromic material is substantially free of carbonyl groups;
(f) when said photochromic material comprises a spiro [1,3-dihydroindole-2,3'-naphtho[2,1-b][1,4]oxazine, substituents Q are attached thereto at the 5-, 6-, 6' and/or 7'-positions and independently comprise for each occurrence —N₃; —CCR', provided that the indolino group is substantially free of N-substituents; or —OSO₂R'", provided that said photochromic material is substantially free of carbonyl groups; and
(g) when said photochromic material comprises a fulgide, Q comprises —N₃, —CN, —CCR', or —OSO₂R'"; and
(B) optionally, said photochromic material has at least one lengthening agent L represented by the following formula (which is described in detail below):

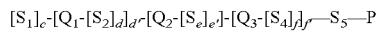

As used herein, the term "attached" means directly bonded to or indirectly bonded to through another group. Thus, for example, according to various non-limiting embodiments disclosed herein, L can be directly bonded to PC as a substituent on PC, or L can be a substituent on another group (such as a group represented by R, which is discussed below) that is directly bonded to PC (i.e., L is indirectly bonded to PC). Although not limiting herein, according to various non-limiting embodiments, L can be attached to PC so as to extend or lengthen PC in an activated state such that the absorption ratio of the extended PC (i.e., the photochromic compound) is enhanced as compared to PC alone. Although not limiting herein, according to various non-limiting embodiments, the location of attachment of L on PC can be chosen such that L lengthens PC in at least one of a direction parallel to or a direction perpendicular to a theoretical transitional dipole moment of the activated form of PC. Regarding the position of L, it may be subsequently attached to the photochromic compound at the location of the Q group. The photochromic compound of the present invention can have at least one Q group at the position(s) indicated and optionally one or more L groups. As used herein the term "theoretical transitional dipole moment" refers to transient dipolar polarization created by interaction of electromagnetic radiation with the molecule. See, for example, IUPAC Compendium of Chemical Technology, 2$^{nd}$ Ed., International Union of Pure and Applied Chemistry (1997).

With reference to L above, each $Q_1$, $Q_2$, and $Q_3$ can be independently chosen for each occurrence from: a divalent group chosen from: an unsubstituted or a substituted aromatic group, an unsubstituted or a substituted alicyclic group, an unsubstituted or a substituted heterocyclic group, and mixtures thereof, wherein substituents are chosen from: a group represented by P, liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$)alkoxy, perfluoro($C_1$-$C_{18}$)alkoxycarbonyl, perfluoro($C_1$-$C_{18}$)alkylcarbonyl, perfluoro($C_1$-$C_{18}$)alkylamino, di-(perfluoro($C_1$-$C_{18}$)alkyl)amino, perfluoro($C_1$-$C_{18}$)alkylthio, $C_1$-$C_{18}$ alkylthio, $C_1$-$C_{18}$ acetyl, $C_3$-$C_{10}$ cycloalkyl, $C_3$-$C_{10}$ cycloalkoxy, a straight-chain or branched $C_1$-$C_{18}$ alkyl group that is mono-substituted with cyano, halo, or $C_1$-$C_{18}$ alkoxy, or poly-substituted with halo, and a group comprising one of the following formulae: -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M. As used herein, the prefix "poly" means at least two.

As discussed above, $Q_1$, $Q_2$, and $Q_3$ can be independently chosen for each occurrence from a divalent group, such as an unsubstituted or a substituted aromatic group, unsubstituted or substituted heterocyclic group, and an unsubstituted or substituted alicyclic group. Non-limiting examples of useful aromatic groups include: benzo, naphtho, phenanthro, biphenyl, tetrahydro naphtho, terphenyl, and anthraceno.

As used herein the term "heterocyclic group" means a compound having a ring of atoms, wherein at least one atom forming the ring is different than the other atoms forming the ring. Further, as used herein, the term heterocyclic group specifically excludes fused heterocyclic groups. Non-limiting examples of suitable heterocyclic groups from which $Q_1$, $Q_2$, and $Q_3$ can be chosen include: isosorbitol, dibenzofuro, dibenzothieno, benzofuro, benzothieno, thieno, furo, dioxino, carbazolo, anthranilyl, azepinyl, benzoxazolyl, diazepinyl, dioazlyl, imidazolidinyl, imidazolyl, imidazolinyl, indazolyl, indoleninyl, indolinyl, indolizinyl, indolyl, indoxazinyl, isobenzazolyl, isoindolyl, isooxazolyl, isooxazyl, isopyrroyl, isoquinolyl, isothiazolyl, morpholino, morpholinyl, oxadiazolyl, oxathiazolyl, oxathiazyl, oxathiolyl, oxatriazolyl, oxazolyl, piperazinyl, piperazyl, piperidyl, purinyl, pyranopyrrolyl, pyrazinyl, pyrazolidinyl, pyrazolinyl, pyrazolyl, pyrazyl, pyridazinyl, pyridazyl, pyridyl, pyrimidinyl, pyrimidyl, pyridenyl, pyrrolidinyl, pyrrolinyl, pyrroyl, quinolizinyl, quinuclidinyl, quinolyl, thiazolyl, triazolyl, triazyl, N-arylpiperazino, aziridino, arylpiperidino, thiomorpholino, tetrahydroquinolino, tetrahydroisoquinolino, pyrryl, unsubstituted, mono- or di-substituted $C_4$-$C_{18}$ spirobicyclic amines, and unsubstituted, mono- or di-substituted $C_4$-$C_{18}$ spirotricyclic amines.

As discussed above, according to various non-limiting embodiments $Q_1$, $Q_2$, and $Q_3$ can be chosen from mono- or di- substituted $C_4$-$C_{18}$ spirobicyclic amine and $C_4$-$C_{18}$ spirotricyclic amine. Non-limiting examples of suitable substituents include aryl, $C_1$-$C_6$ alkyl, $C_1$-$C_6$ alkoxy or phenyl ($C_1$-$C_6$)alkyl. Specific non-limiting examples of mono- or di-substituted spirobicyclic amines include: 2-azabicyclo [2.2.1]hept-2-yl; 3-azabicyclo[3.2.1]oct-3-yl; 2-azabicyclo [2.2.2]oct-2-yl; and 6-azabicyclo[3.2.2]nonan-6-yl. Specific non-limiting examples of mono- or di-substituted tricyclic amines include: 2-azatricyclo[3.3.1.1(3,7)]decan-2-yl; 4-benzyl-2-azatricyclo[3.3.1.1(3,7)]decan-2-yl; 4-methoxy-6-methyl-2-azatricyclo[3.3.1.1(3,7)]decan-2-yl; 4-azatricyclo[4.3.1.1(3,8)]undecan-4-yl; and 7-methyl-4-azatricyclo [4.3.1.1(3,8)]undecan-4-yl.

Examples of alicyclic groups from which $Q_1$, $Q_2$, and $Q_3$ can be chosen include, without limitation, cyclohexyl, cyclopropyl, norbornenyl, decalinyl, adamantanyl, bicyclooctane, per-hydrofluorene, and cubanyl.

With continued reference to L, each $S_1$, $S_2$, $S_3$, $S_4$, and $S_5$ is independently chosen for each occurrence from a spacer unit chosen from:
(1) —(CH₂)$_g$—, —(CF₂)$_h$—, —Si(CH₂)$_g$—, —(Si[(CH₃)₂]O)$_h$—, wherein g is independently chosen for each occurrence from 1 to 20; h is chosen from 1 to 16 inclusive;
(2) —N(Z)—, —C(Z)=C(Z)—, —C(Z)=N—, —C(Z')—C(Z')—, or a single bond, wherein Z is independently chosen for each occurrence from hydrogen, $C_1$-$C_6$ alkyl, $C_3$-$C_{10}$ cycloalkyl and aryl, and Z' is independently chosen for each occurrence from $C_1$-$C_{18}$ alkyl, $C_3$-$C_{10}$ cycloalkyl and aryl; and (3) —O—, —C(O)—, —C≡C—, —N=N—, —S—, —S(O)—, —S(O)(O)—, —(O)S(O)O—, —O(O)S(O)O— straight-chain or branched $C_1$-$C_{24}$ alkylene residue, said $C_1$-$C_{24}$ alkylene residue being unsubstituted, mono-substituted by cyano or halo, or poly-substituted by halo; provided that when two spacer units comprising heteroatoms are linked together the spacer units are linked so that heteroatoms are not directly linked to each other and when $S_1$ and $S_5$ are linked to PC and P, respectively, they are linked so that two heteroatoms are not directly linked to each other. As used herein the term "heteroatom" means atoms other than carbon or hydrogen.

According to various non-limiting embodiments disclosed herein, in L, c, d, e, and f each can be independently chosen from an integer ranging from 1 to 20, inclusive; and d', e' and f' each can be independently chosen from 0, 1, 2, 3, and 4, provided that the sum of d'+e'+f is at least 1. According to other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f is at least 2. According to still other non-limiting embodiments disclosed herein, c, d, e, and f each can be independently chosen from an integer ranging from 0 to 20, inclusive; and d', e' and f'each can be independently chosen from 0, 1, 2, 3, and 4, provided that the sum of d'+e'+f is at least 3. According to still other non-limiting embodiments disclosed herein, c, d, e, and f each can be independently chosen from an integer ranging from 0 to 20, inclusive; and d', e' and f'each can be independently chosen from 0, 1, 2, 3, and 4, provided that the sum of d'+e'+f is at least 1.

Further, in L, P can be chosen from: hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$) alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$)alkyl, polyethyleneoxy, polypropyleneoxy, ethylenyl, acryloyl, acryloyloxy($C_1$-$C_{18}$) alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, or substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$)alkyl, cyano, cyano($C_1$-$C_{18}$) alkyl, cyano($C_1$-$C_{18}$)alkoxy or mixtures thereof, or P is a structure having from 2 to 4 reactive groups or P is an unsubstituted or substituted ring opening metathesis polymerization precursor.

According to various non-limiting embodiments disclosed herein, when P is a polymerizable group, the polymerizable group can be any functional group adapted to participate in a polymerization reaction. Non-limiting examples of polymerization reactions include those described in the definition of "polymerization" in *Hawley's Condensed Chemical Dictionary Thirteenth Edition*, 1997, John Wiley & Sons, pages 901-902, which disclosure is incorporated herein by reference. For example, although not limiting herein, polymerization reactions include: "addition polymerization," in which free radicals are the initiating agents that react with the double bond of a monomer by adding to it on one side at the same time producing a new free electron on the other side; "condensation polymerization," in which two reacting molecules combine to form a larger molecule with elimination of a small molecule, such as a water molecule; and "oxidative coupling polymerization." Further, non-limiting examples of polymerizable groups include hydroxy, acryloxy, methacryloxy, 2-(acryloxy)ethylcarbamyl, 2-(methacryloxy)ethylcarbamyl, isocyanate, aziridine, allylcarbonate, and epoxy, e.g., oxiranylmethyl.

According to one specific, non-limiting embodiment, P can be chosen from a main-chain or a side-chain liquid crystal polymer and a liquid crystal mesogen. As used herein, the term liquid crystal "mesogen" means rigid rod-like or disc-like liquid crystal molecules. Further, as used herein the term "main-chain liquid crystal polymer" refers to a polymer having liquid crystal mesogens within the backbone (i.e., the main chain) structure of the polymer. As used herein the term "side-chain liquid crystal polymer" refers to a polymer having liquid crystal mesogens attached to the polymer at the side chains. Although not limiting herein, generally, the mesogens are made up of two or more aromatic rings that restrict the movement of a liquid crystal polymer. Examples of suitable rod-like liquid crystal mesogens include without limitation: substituted or unsubstituted aromatic esters, substituted or unsubstituted linear aromatic compounds, and substituted or unsubstituted terphenyls.

According to another specific, non-limiting embodiment, P can be chosen from a steroid radical, for example and without limitation, a cholesterolic compound.

As is discussed above, various non-limiting embodiments disclosed herein provide a photochromic compound comprising (a) a photochromic group (PC) and (b) at least one Q group at the position described herein and optionally at least one lengthening agent (L) (above) attached to PC.

In alternative embodiments, the photochromic compound may be represented by the following graphic formula I, II, III, IVA, IVB, V or VI:

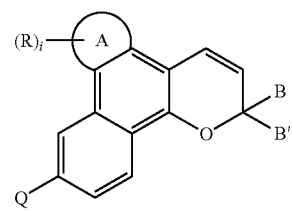

I

-continued

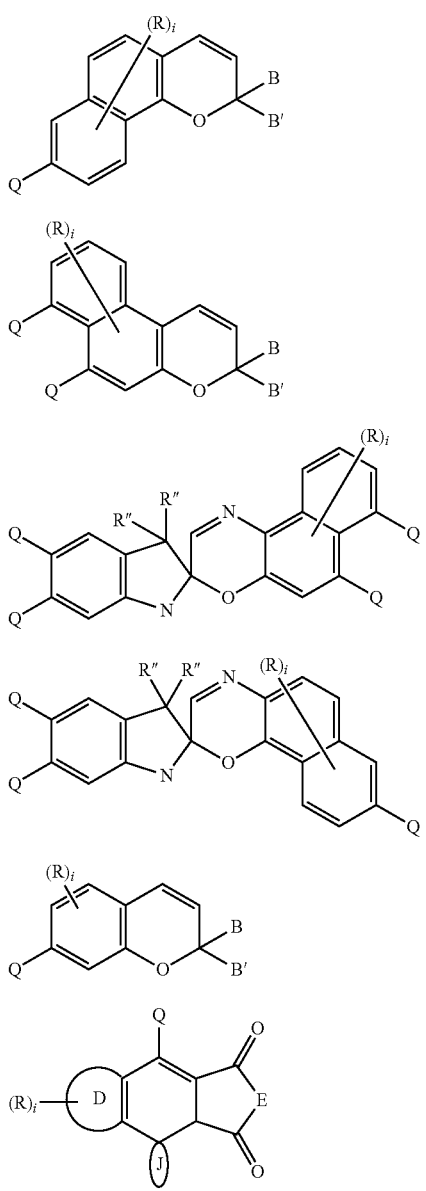

wherein:
(A) each substituent Q independently comprises —$N_3$, —CN, —COOR', —CCR', —OCOR', —OCOOR', —SR', —$OSO_2R'''$, and/or —CONHR', wherein each R' comprises hydrogen, an unsubstituted or substituted alkyl group having from 1 to 18 carbon atoms, an unsubstituted or substituted aryl group, an unsubstituted or substituted alkene or alkyne group having from 2 to 18 carbon atoms, wherein said substituents are chosen from halo and hydroxyl and R''' comprises —$CF_3$ or a perfluorinated alkyl group having from 2 to 18 carbon atoms;
(B) each i is an integer chosen from 0 to the total number of available positions and each R is independently chosen for each occurrence from:
   (a) a group represented by B described hereinafter;
   (b) —$C(O)X_{24}$, wherein $X_{24}$ is chosen from a lengthening agent L, hydroxy, $C_1$-$C_{18}$ alkyl, $C_1$-$C_{18}$ alkoxy, phenyl that is unsubstituted or mono-substituted with $C_1$-$C_{18}$ alkyl or $C_1$-$C_{18}$ alkoxy, amino that is unsubstituted, mono- or di-substituted with at least one of $C_1$-$C_{18}$ alkyl, phenyl, benzyl, and naphthyl;
   (c) —$OX_7$ and —$N(X_7)_2$; wherein $X_7$ is chosen from:
      (i) a lengthening agent L, hydrogen, $C_1$-$C_{18}$ alkyl, $C_1$-$C_{18}$ acyl, phenyl($C_1$-$C_{18}$)alkyl, mono($C_1$-$C_{18}$)alkyl substituted phenyl($C_1$-$C_{18}$)alkyl, mono($C_1$-$C_{18}$)alkoxy substituted phenyl($C_1$-$C_{18}$)alkyl; $C_1$-$C_{18}$ alkoxy($C_1$-$C_{18}$)alkyl; $C_3$-$C_{10}$ cycloalkyl; mono($C_1$-$C_{18}$)alkyl substituted $C_3$-$C_{10}$ cycloalkyl, $C_1$-$C_{18}$ haloalkyl, allyl, benzoyl, mono-subsituted benzoyl, naphthoyl or mono-substituted naphthoyl, wherein each of said benzoyl and naphthoyl substituents are independently chosen from $C_1$-$C_{18}$ alkyl, and $C_1$-$C_{18}$ alkoxy;
      (ii) —$CH(X_8)X_9$, wherein $X_8$ is chosen from a lengthening agent L, hydrogen or $C_1$-$C_{18}$ alkyl; and $X_9$ is chosen from a lengthening agent L, —CN, —$CF_3$, or —$COOX_{10}$, wherein $X_{10}$ is chosen from a lengthening agent L, hydrogen or $C_1$-$C_{18}$ alkyl;
      (iii) —$C(O)X_6$, wherein $X_6$ is chosen from at least one of: a lengthening agent L, hydrogen, $C_1$-$C_{18}$ alkoxy, phenoxy that is unsubstituted, mono- or di- substituted with $C_1$-$C_{18}$ alkyl or $C_1$-$C_{18}$ alkoxy, an aryl group that is unsubstituted, mono- or di-substituted with $C_1$-$C_{18}$ alkyl or $C_1$-$C_{18}$ alkoxy, an amino group that is unsubstituted, mono- or di-substituted with $C_1$-$C_{18}$ alkyl, and a phenylamino group that is unsubstituted, mono- or di-substituted with $C_1$-$C_{18}$ alkyl or $C_1$-$C_{18}$ alkoxy; or
      (iv) tri($C_1$-$C_{18}$)alkylsilyl, tri($C_1$-$C_{18}$)alkylsilyloxy, tri($C_1$-$C_{18}$)alkoxysilyl, tri($C_1$-$C_{18}$)alkoxysilyloxy, di($C_1$-$C_{18}$)alkyl($C_1$-$C_{18}$ alkoxy)silyl, di($C_1$-$C_{18}$)alkyl($C_1$-$C_{18}$ alkoxy)silyloxy, di($C_1$-$C_{18}$)alkoxy($C_1$-$C_{18}$ alkyl)silyl or di($C_1$-$C_{18}$)alkoxy($C_1$-$C_{18}$ alkyl)silyloxy;
   (d) —$SX_{11}$; wherein $X_{11}$ is chosen from a lengthening agent L, hydrogen, $C_1$-$C_{18}$ alkyl, $C_1$-$C_{18}$ haloalkyl, an aryl group that is unsubstituted, or mono- or di-substituted with $C_1$-$C_{18}$ alkyl, $C_1$-$C_{18}$ alkoxy, or halogen;
   (e) a nitrogen containing ring represented by Formula i:

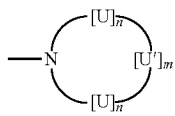

wherein
   (i) n is an integer chosen from 0, 1, 2, and 3, provided that if n is 0, U' is U, and each U is independently chosen for each occurrence from —$CH_2$—, —CH($X_{12}$)—, —$C(X_{12})_2$—, —CH($X_{13}$)—, —$C(X_{13})_2$—, and —$C(X_{12})(X_{13})$—, wherein $X_{12}$ is chosen from a lengthening agent L and $C_1$-$C_{12}$ alkyl, and $X_{13}$ is chosen from a lengthening agent L, phenyl and naphthyl, and (ii) U' is chosen from U, —O—, —S—, —S(O)—, —NH—, —N(X$_{12}$)— or —N(X$_{13}$)—, and m is an integer chosen from 1, 2, and 3;

(f) the group represented by Formula ii or iii;

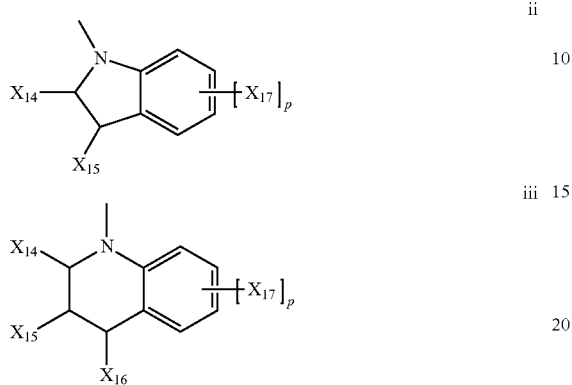

wherein X$_{14}$, X$_{15}$, and X$_{16}$ are independently chosen for each occurrence from a lengthening agent L, hydrogen, C$_1$-C$_{18}$ alkyl, phenyl or naphthyl, or X$_{14}$ and X$_{15}$ together form a ring of 5 to 8 carbon atoms; p is an integer chosen from 0, 1, or 2, and X$_{17}$ is independently chosen for each occurrence from a lengthening agent L, C$_1$-C$_{18}$ alkyl, C$_1$-C$_{18}$ alkoxy, or halogen;

(g) immediately adjacent R groups together form a group represented by Formula vii, viii, or ix:

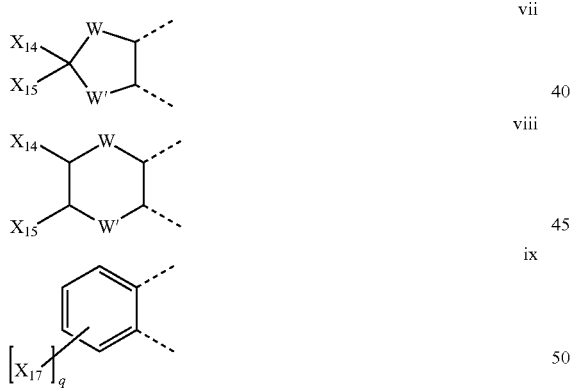

wherein
(i) W and W' are independently chosen for each occurrence from —O—, —N(X$_7$)—, —C(X$_{14}$)—, and —C(X$_{17}$)—;
(ii) X$_{14}$, X$_{15}$ and X$_{17}$, wherein X$_{14}$, and X$_{15}$ are independently chosen for each occurrence from a lengthening agent L, hydrogen, C$_1$-C$_{18}$ alkyl, phenyl or naphthyl, or X$_{14}$ and X$_{15}$ together form a ring of 5 to 8 carbon atoms; and X$_{17}$ is independently chosen for each occurrence from a lengthening agent L, C$_1$-C$_{18}$ alkyl, C$_1$-C$_{18}$ alkoxy, or halogen; and
(iii) q is an integer chosen from 0, 1, 2, 3, and 4; and (h) a lengthening agent L represented by:

wherein:
(i) each Q$_1$, Q$_2$, and Q$_3$ is independently chosen for each occurrence from: a divalent group chosen from: an unsubstituted or a substituted aromatic group, an unsubstituted or a substituted alicyclic group, an unsubstituted or a substituted heterocyclic group, and mixtures thereof, wherein substituents are chosen from: a group represented by P, liquid crystal mesogens, halogen, poly(C$_1$-C$_{18}$ alkoxy), C$_1$-C$_{18}$ alkoxycarbonyl, C$_1$-C$_{18}$ alkylcarbonyl, C$_1$-C$_{18}$ alkoxycarbonyloxy, aryloxycarbonyloxy, perfluoro(C$_1$-C$_{18}$)alkoxy, perfluoro(C$_1$-C$_{18}$)alkoxycarbonyl, perfluoro(C$_1$-C$_{18}$)alkylcarbonyl, perfluoro(C$_1$-C$_{18}$)alkylamino, di-(perfluoro(C$_1$-C$_{18}$)alkyl)amino, perfluoro(C$_1$-C$_{18}$)alkylthio, C$_1$-C$_{18}$ alkylthio, C$_1$-C$_{18}$ acetyl, C$_3$-C$_{10}$ cycloalkyl, C$_3$-C$_{10}$ cycloalkoxy, a straight-chain or branched C$_1$-C$_{18}$ alkyl group that is mono-substituted with cyano, halo, or C$_1$-C$_{18}$ alkoxy, or poly-substituted with halo, and a group comprising one of the following formulae: -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M;
(ii) c, d, e, and f are each independently chosen from an integer ranging from 0 to 20, inclusive; and each S$_1$, S$_2$, S$_3$, S$_4$, and S$_5$ is independently chosen for each occurrence from a spacer unit chosen from:
(1) —(CH$_2$)$_g$—, —(CF$_2$)$_h$—, —Si(CH$_2$)$_g$—, —(Si[(CH$_3$)$_2$]O)$_h$—, wherein g is independently chosen for each occurrence from 1 to 20; h is a whole number from 1 to 16 inclusive;
(2) —N(Z)—, —C(Z)=C(Z)—, —C(Z)=N—, —C(Z')—C(Z')— or a single bond, wherein Z is independently chosen for each occurrence from hydrogen, C$_1$-C$_{18}$ alkyl, C$_3$-C$_{10}$ cycloalkyl and aryl, and Z' is independently chosen for each occurrence from C$_1$-C$_{18}$ alkyl, C$_3$-C$_{10}$ cycloalkyl and aryl; and
(3) —O—, —C(O)—, —C≡C—, —N=N—, —S—, —S(O)—, —S(O)(O)—, —(O)S(O)—, —(O)S(O)O—, —O(O)S(O)O—, or straight-chain or branched C$_1$-C$_{24}$ alkylene residue, said C$_1$-C$_{24}$ alkylene residue being unsubstituted, mono-substituted by cyano or halo, or poly-substituted by halo; provided that when two spacer units comprising heteroatoms are linked together the spacer units are linked so that heteroatoms are not directly linked to each other and when S$_1$ and S$_5$ are linked to PC and P, respectively, they are linked so that two heteroatoms are not directly linked to each other;
(iii) P is chosen from: hydroxy, amino, C$_2$-C$_{18}$ alkenyl, C$_2$-C$_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$) alkylene, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$) alkylene, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$) alkylene, polyethyleneoxy, polypropyleneoxy, ethylenyl, acryloyl, acryloyloxy($C_1$-$C_{18}$)alkylene, methacryloyl, methacryloyloxy($C_1$-$C_{18}$) alkylene, 2-chloroacryloyl, 2-phenylacryloyl, acryloylphenylene, 2-chloroacryloylamino, 2-phenylacryloylamino-carbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, or substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$) alkyl, cyano, cyano($C_1$-$C_{18}$)alkyl, cyano($C_1$-$C_{18}$)alkoxy or mixtures thereof, or P is a structure having from 2 to 4 reactive groups or P is an unsubstituted or substituted ring opening metathesis polymerization precursor; and (iv) d', e' and f' are each independently chosen from 0, 1, 2, 3, and 4, provided that a sum of d'+e'+f' is at least 1;

(C) provided that when said photochromic material is represented by graphic formula I:
(a) Q comprises —CN, and said photochromic material of graphic formula I is substantially free of substituents at the 12-position, or Q comprises —$N_3$, —COOR', —CCR', —C(R')C(R')R', —OCOR', —OCOOR', —SR', and —OSO$_2$R'";
(b) the group A represents indeno, thiopheno, benzothiopheno, furo or benzofuro; and
(c) B and B' are each independently chosen from:
(i) hydrogen, $C_1$-$C_{18}$ alkyl, $C_2$-$C_{18}$ alkylidene, $C_2$-$C_{18}$ alkylidyne, vinyl, $C_3$-$C_{10}$ cycloalkyl, $C_1$-$C_{18}$ haloalkyl, allyl, halogen, and benzyl that is unsubstituted or mono-substituted with at least one of $C_1$-$C_{18}$ alkyl and $C_1$-$C_{18}$ alkoxy;
(ii) phenyl that is mono-substituted at the para position with at least one substituent chosen from: $C_1$-$C_{18}$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_{18}$ alkyl substituted phenylene, mono- or poly-urethane($C_1$-$C_{20}$)alkylene, mono- or poly-ester($C_1$-$C_{20}$) alkylene, mono- or poly-carbonate($C_1$-$C_{20}$) alkylene, polysilanylene, polysiloxanylene and mixtures thereof, wherein the at least one substituent is connected to an aryl group of a photochromic material;
(iii) —CH(CN)$_2$ and —CH(COOX$_1$)$_2$, wherein X$_1$ is chosen from at least one of a lengthening agent L, hydrogen, $C_1$-$C_{18}$ alkyl that is unsubstituted or mono-substituted with phenyl, phenyl($C_1$-$C_{18}$)alkyl that is mono-substituted with $C_1$-$C_{18}$ alkyl, $C_1$-$C_{18}$ haloalkyl or $C_1$-$C_{18}$ alkoxy, and an aryl group that is unsubstituted, mono- or di-substituted, wherein each aryl substituent is independently chosen from $C_1$-$C_{18}$ alkyl and $C_1$-$C_{18}$ alkoxy; and lengthening agent L;
(iv) —CH(X$_2$)(X$_3$), wherein:
(I) X$_2$ is chosen from at least one of a lengthening agent L, hydrogen, $C_1$-$C_{18}$ alkyl, and an aryl group that is unsubstituted, mono- or di-substituted, wherein each aryl substituent is independently chosen from $C_1$-$C_{18}$ alkyl and $C_1$-$C_{18}$ alkoxy; and
(2) X$_3$ is chosen from at least one of —COOX$_1$, —COX$_1$, —COX$_4$, and —CH$_2$OX$_5$, wherein: X$_4$ is chosen from at least one of morpholino, piperidino, amino that is unsubstituted, mono- or di- substituted with $C_1$-$C_{18}$ alkyl, and an unsubstituted, mono or di- substituted group chosen from phenylamino and diphenylamino, wherein each substituent is independently chosen from $C_1$-$C_{18}$ alkyl or $C_1$-$C_{18}$ alkoxy; and X$_5$ is chosen from a lengthening agent L, hydrogen, —C(O)X$_2$, $C_1$-$C_{18}$ alkyl that is unsubstituted or mono-substituted with ($C_1$-$C_{18}$)alkoxy or phenyl, phenyl($C_1$-$C_{18}$)alkyl that is mono-substituted with ($C_1$-$C_{18}$)alkoxy, and an aryl group that is unsubstituted, mono- or di-substituted, wherein each aryl substituent is independently chosen from $C_1$-$C_{18}$ alkyl and $C_1$-$C_{18}$ alkoxy;
(v) an unsubstituted, mono-, di-, or tri- substituted aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, or fluorenyl; wherein each aryl and heteroaromatic group substituent is independently chosen for each occurrence from:
(1) a lengthening agent L;
(2) —COOX$_1$ or —C(O)X$_6$;
(3) aryl, haloaryl, $C_3$-$C_{10}$ cycloalkylaryl, and an aryl group that is mono- or di-substituted with $C_1$-$C_{18}$ alkyl or $C_1$-$C_{18}$ alkoxy;
(4) $C_1$-$C_{18}$ alkyl, $C_3$-$C_{10}$ cycloalkyl, cycloalkyloxy($C_1$-$C_{18}$)alkyl, aryl($C_1$-$C_{18}$)alkyl, aryloxy($C_1$-$C_{18}$)alkyl, mono- or di-($C_1$-$C_{18}$)alkylaryl($C_1$-$C_{18}$)alkyl, mono- or di-($C_1$-$C_{18}$)alkoxyaryl($C_1$-$C_{18}$)alkyl, $C_1$-$C_{18}$ haloalkyl, and mono($C_1$-$C_{18}$)alkoxy($C_1$-$C_{18}$)alkyl;
(5) $C_1$-$C_{18}$ alkoxy, $C_3$-$C_{10}$ cycloalkoxy, cycloalkyloxy($C_1$-$C_{18}$)alkoxy, aryl($C_1$-$C_{18}$) alkoxy, aryloxy($C_1$-$C_{18}$)alkoxy, mono- or di-($C_1$-$C_{18}$)alkylaryl($C_1$-$C_{18}$)alkoxy, and mono- or di-($C_1$-$C_{18}$)alkoxyaryl($C_1$-$C_{18}$)alkoxy;
(6) aminocarbonyl, aminocarbonyl($C_1$-$C_{18}$) alkylene, amino, mono- or di-alkylamino, diarylamino, piperazino, N—(C$_1$-C$_{18}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;

(7) —OX$_7$ or N(X$_7$)$_2$;

(8) —SX$_{11}$;

(9) a nitrogen containing ring represented by Formula i;

(10) a group represented by Formula ii or iii;

(11) an unsubstituted or mono-substituted group chosen from pyrazolyl, imidazolyl, pyrazolinyl, imidazolinyl, pyrrolidinyl, phenothiazinyl, phenoxazinyl, phenazinyl, or acridinyl, wherein each substituent is independently chosen from a lengthening agent L, C$_1$-C$_{18}$ alkyl, C$_1$-C$_{18}$ alkoxy, phenyl, hydroxy, amino or halogen;

(12) a group represented by Formula iv or v:

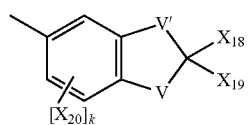

iv

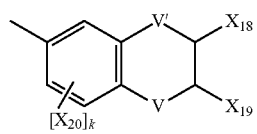

v wherein:
(I) V' is independently chosen in each formula from —O—, —CH—, C$_1$-C$_6$ alkylene, and C$_3$-C$_{10}$ cycloalkylene, (II) V is independently chosen in each formula from —O— or —N(X$_{21}$)—, wherein X$_{21}$ is a lengthening agent L, hydrogen, C$_1$-C$_{18}$ alkyl, and C$_2$-C$_{18}$ acyl, provided that if V is —N(X$_{21}$)—, V' is —CH$_2$—, (III) X$_{18}$ and X$_{19}$ are each independently chosen from a lengthening agent L, hydrogen and C$_1$-C$_{18}$ alkyl, and (IV) k is chosen from 0, 1, and 2, and each X$_{20}$ is independently chosen for each occurrence from a lengthening agent L, C$_1$-C$_{18}$ alkyl, C$_1$-C$_{18}$ alkoxy, hydroxy and halogen;

(13) a group represented by Formula vi:

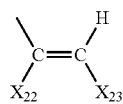

vi wherein
(I) X$_{22}$ is chosen from a lengthening agent L, hydrogen and C$_1$-C$_{18}$ alkyl, and (II) X$_{23}$ is chosen from a lengthening agent L and an unsubstituted, mono-, or di-substituted group chosen from naphthyl, phenyl, furanyl and thienyl, wherein each substituent is independently chosen for each occurrence from C$_1$-C$_{18}$ alkyl, C$_1$-C$_{18}$ alkoxy, and halogen; and

(14) B and B' together form fluoren-9-ylidene, mono- or di-substituted fluoren-9-ylidene, or a saturated C$_3$-C$_{12}$ spiro-monocyclic hydrocarbon ring, e.g., cyclopropylidene, cyclobutylidene, cyclopentylidene, cyclohexylidene, cycloheptylidene, cyclooctylidene, cyclononylidene, cyclodecylidene cycloundecylidene, cyclododecylidene; saturated C$_7$-C$_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1]octylidene, bicyclo[3.3.1]nonan-9-ylidene, bicyclo[4.3.2]undecane; saturated C$_7$-C$_{12}$ spiro-tricyclic hydrocarbon rings, e.g., tricyclo[2.2.1.0$^{2.6}$]heptylidene, tricyclo[3.3.1.1$^{3.7}$]decylidene, i.e., adamantylidene, and tricyclo[5.3.1.1$^{2.6}$]dodecyliden; and a lengthening agent L, said fluoren-9-ylidene substituents being selected from the group consisting of C$_1$-C$_4$ alkyl, C$_1$-C$_4$ alkoxy, bromo, fluoro and chloro;

(D) provided that when said photochromic material is represented by graphic formula II, Q comprises —N$_3$ or —OCOOR' provided that said photochromic material of graphic formula II is substantially free of substituents at the 5-position; and R, i, B and B' are the same as stated hereinbefore;

(E) provided that when said photochromic material is represented by graphic formula III, Q independently comprises for each occurrence, —N$_3$ or —OCOOR'; and R, B and B' are the same as hereinbefore;

(F) provided that when said photochromic material is represented by graphic formula IVA or IVB, Q independently comprises for each occurrence —N$_3$; or —CCR', provided that the indolino group is substantially free of N-substituents; or —OSO$_2$R''', provided that said photochromic material is substantially free of carbonyl groups and each R'' is independently chosen for each occurrence from hydrogen, a substituted or unsubstituted alkyl, cycloalkyl, arylalkyl, or together form cycloalkyl that is substituted or unsubstituted; and R and i are the same as hereinbefore;

(G) provided that when said photochromic material is represented by graphic formula V, Q comprises —N$_3$, —CN, —CCR', or —OSO$_2$R'''; and R, i, B and B' are the same as hereinbefore; and (H) provided that when said photochromic material is represented by graphic formula VI, Q comprises: —N$_3$, —CN, —CCR', or —OSO$_2$R'''; E is —O— or —N(Q)- ; and D is represented by the following graphic formula:

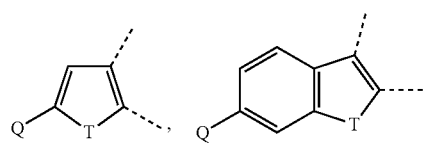

wherein: T is —S—, —O— or —N(R)—, J is a spiroalicyclic ring and Q is the same as described hereinbefore.

According to one specific, non-limiting embodiment, wherein the photochromic group comprises at least two PCs, the PCs can be linked to one another via linking group substituents on the individual PCs. For example, the PCs can be polymerizable photochromic groups or photochromic groups that are adapted to be compatible with a host material ("compatibilized photochromic group"). Non-limiting examples of polymerizable photochromic groups from which PC can be chosen and that are useful in conjunction with various non-limiting embodiments disclosed herein are disclosed in U.S. Pat. No. 6,113,814, which is hereby specifically incorporated by reference herein. Non-limiting examples of compatibilized photochromic groups from which PC can be chosen and that are useful in conjunction with various non-limiting embodiments disclosed herein are disclosed in U.S. Pat. No. 6,555,028, which is hereby specifically incorporated by reference herein.

Other suitable photochromic groups and complementary photochromic groups are described in U.S. Pat. No. 6,080,338 at column 2, line 21 to column 14, line 43; U.S. Pat. No. 6,136,968 at column 2, line 43 to column 20, line 67; U.S. Pat. No. 6,296,785 at column 2, line 47 to column 31, line 5; U.S. Pat. No. 6,348,604 at column 3, line 26 to column 17, line 15; U.S. Pat. No. 6,353,102 at column 1, line 62 to column 11, line 64; and U.S. Pat. No. 6,630,597 at column 2, line 16 to column 16, line 23; the disclosures of the aforementioned patents are incorporated herein by reference.

Another non-limiting embodiment provides the aforementioned lengthening agent (L) attached to the at least one photochromic group, wherein the at least one lengthening agent is chosen from one of the following compounds listed (and graphically represented) below:

(1)

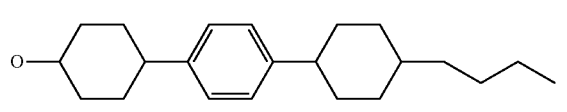

4-[4-(4-butyl-cyclohexyl)-phenyl]-cyclohexyloxy (2)

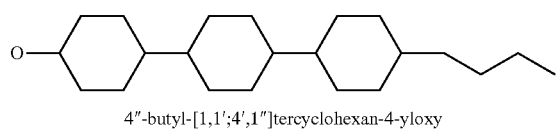

4″-butyl-[1,1′;4′,1″]tercyclohexan-4-yloxy (3)

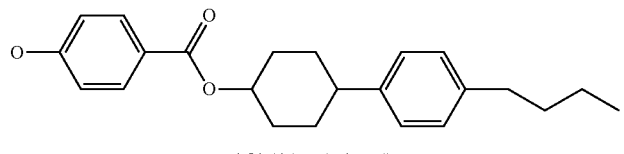

4-[4-(4-butyl-phenyl)-cyclohexyloxycarbonyl]-phenoxy (4)

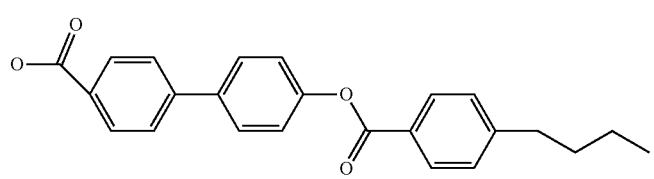

4′-(4-butyl-benzoyloxy)-biphenyl-4-carbonyloxy (5)

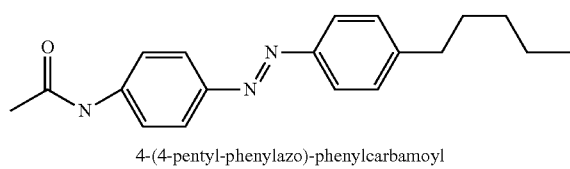

4-(4-pentyl-phenylazo)-phenylcarbamoyl (6)

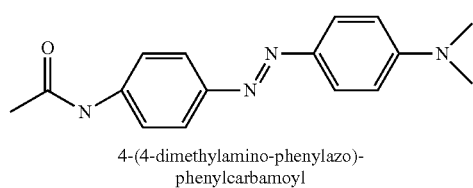

4-(4-dimethylamino-phenylazo)-phenylcarbamoyl

-continued (7)

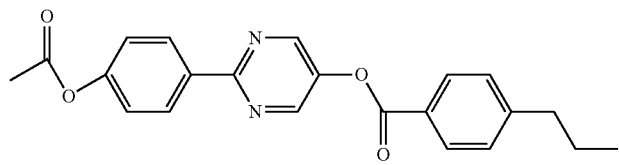

{4-[5-(4-propyl-benzoyloxy)-pyrimidin-2-yl]-phenyl}ester (8)

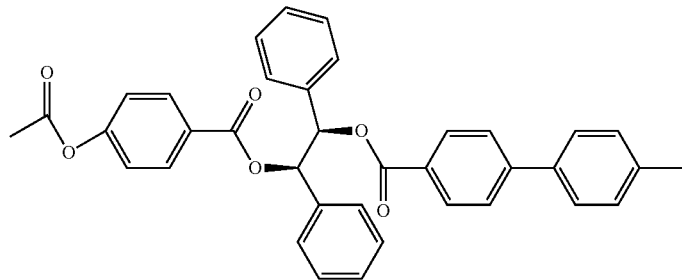

{4-[2-(4'-methyl-biphenyl-4-carbonyloxy)-1,2-diphenyl-ethoxycarbonyl]-phenyl}ester (9)

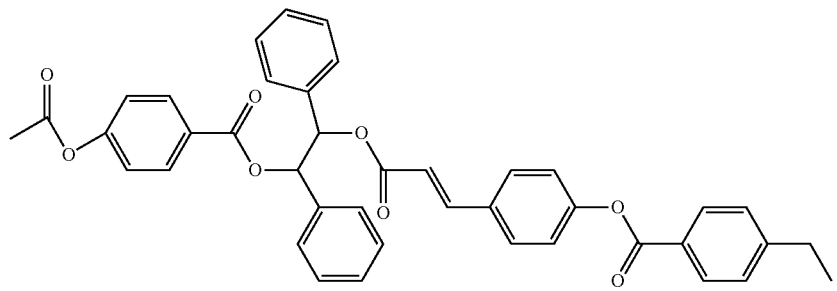

[4-[1,2-phenyl-2-{3-[4-(4-propyl-benzoyloxy)-phenyl]-acryloyloxy}-ethoxycarbonyl)-phenyl]ester (10)

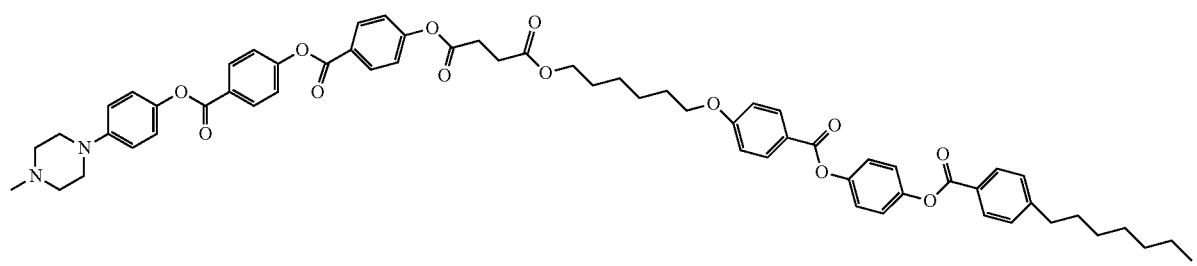

4-[4-(4-{4-[3-(6-{4-[4-(4-nonyl-benzoyloxy)-phenoxycarbonyl]-phenoxy}-hexyloxycarbonyl)-propionyloxy]-benzoyloxy}-benzoyloxy)-phenyl]-piperazin-1-yl (11)

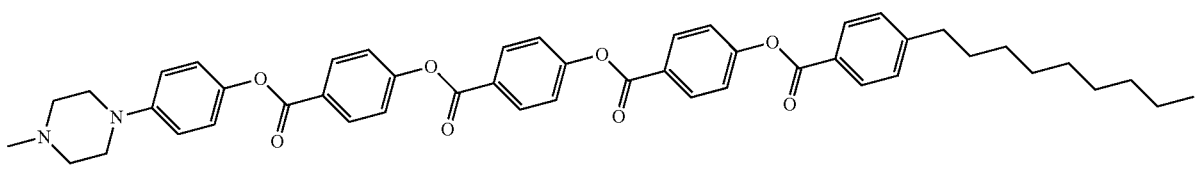

{4-[4-(4-{4-[4-(4-nonyl-benzoyloxy)-benzoyloxy]-benzoyloxy}-benzoyloxy)-phenyl]-piperazin-1-yl}

(12)
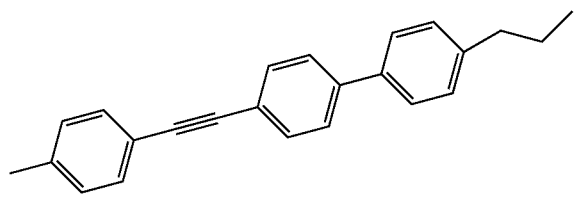
4-(4′-propyl-biphenyl-4-ylethynyl)-phenyl
(13)
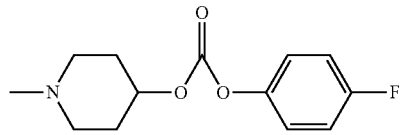
4-(4-fluoro-phenoxycarbonyloxy)-
piperidin-1-yl
(14)
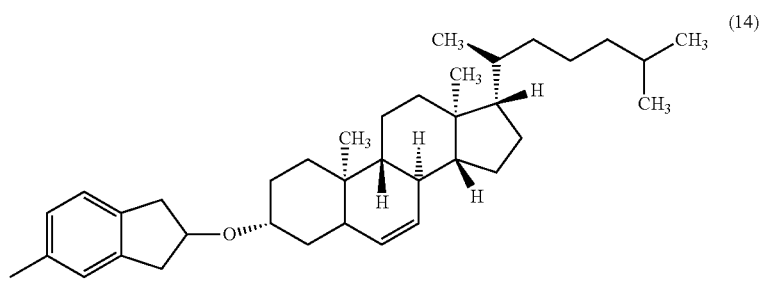
2-[17-(1,5-dimethyl-hexyl)-10,13-
dimethyl-2,3,4,7,8,9,10,11,12,13,14,15,16,17-
tetradecahydro-1H-
cyclopenta[a]phenanthren-3-yloxy]-indan-5-yl
(15)
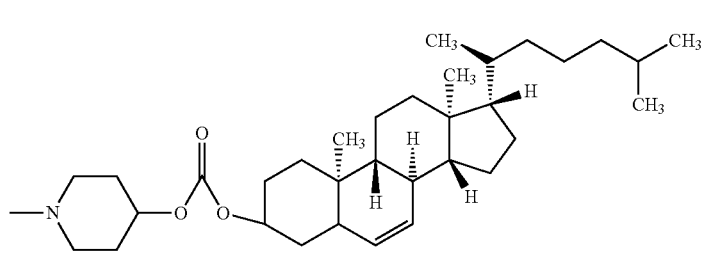
4-[17-(1,5-dimethyl-hexyl)-10,13-
dimethyl-
2,3,4,7,8,9,10,11,12,13,14,15,16,17-
tetradecahydro-1H-
cyclopenta[a]phenanthren-3-
yloxycarbonyloxy]-piperidin-1-yl
(16)
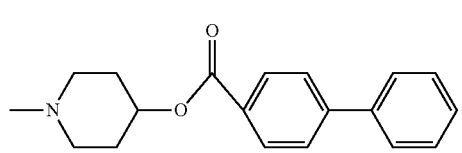
4-(biphenyl-4-carbonyloxy)-piperidin-1-yl
(17)
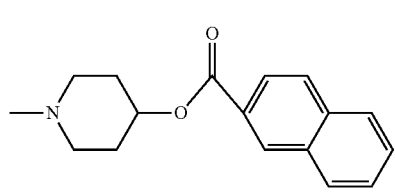
4-(naphthalene-2-carbonyloxy)-
piperidin-1-yl -continued

(18)
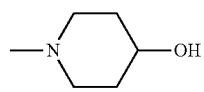
4-hydroxy-piperidin-1-yl

(19)
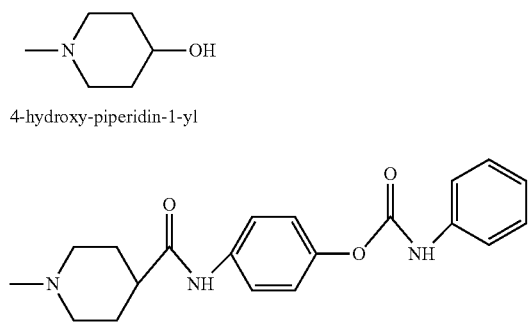
4-(4-phenylcarbamoyl-
phenylcarbamoyl)-piperidin-1-yl

(20)
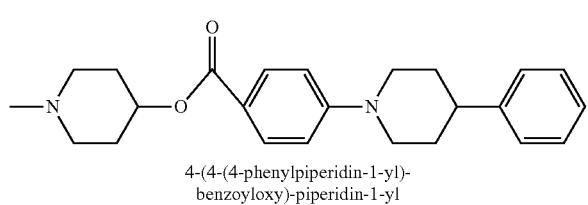
4-(4-(4-phenylpiperidin-1-yl)-
benzoyloxy)-piperidin-1-yl

(21)
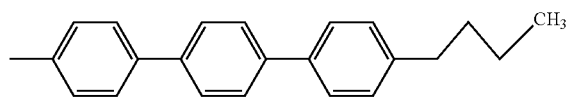
4-butyl-[1,1';4',1'']terphenyl-4-yl

(22)
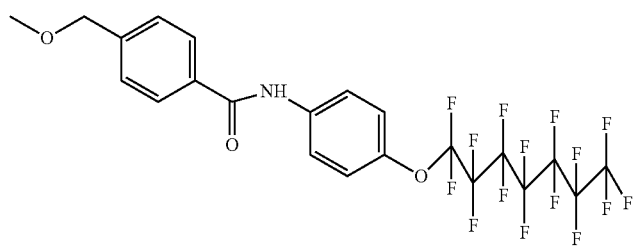
4-(4-pentadecafluoroheptyloxy-
phenylcarbamoyl)-benzyloxy

(23)
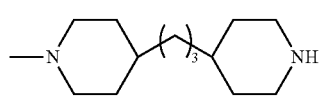
4-(3-piperidin-4-yl-propyl)-piperidin-1-
yl

(24)
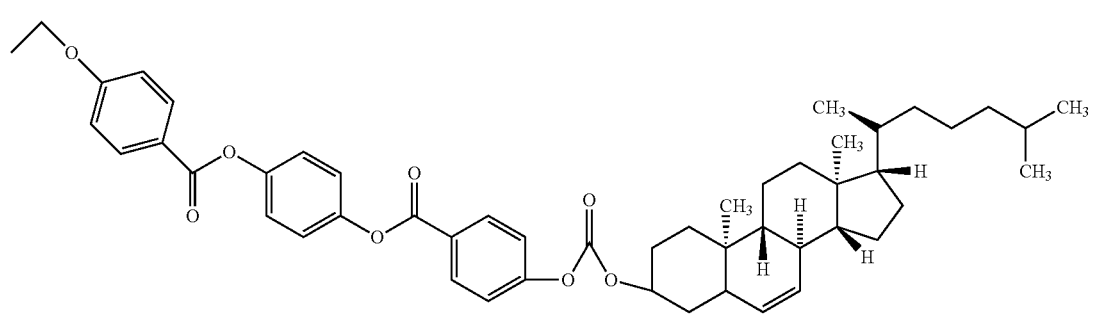
4-(4-{4-[17-(1,5-dimethyl-hexyl)-10,13-
dimethyl-2,3,4,7,8,9,10,11,12,13,14,15,16,17-
tetradecahydro-1H-
cyclopenta[a]phenanthren-3-
yloxycarbonyloxy]-benzoyloxy}-
phenpxycarbonyl)-phenoxymethyl

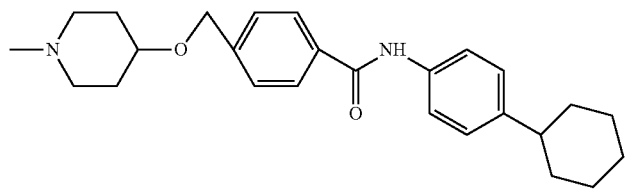
4-[4-(4-cyclohexyl-phenylcarbomoyl)-benzyloxy]-piperidin-1-yl
(25)
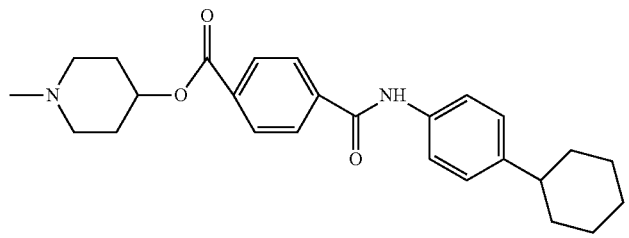
4-[4-(4-cyclohexyl-phenylcarbomoyl)-benzoyloxy]-piperidin-1-yl
(26)
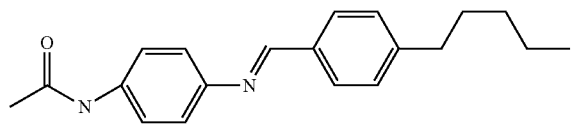
N-{4-[(4-pentyl-benzylidene)-amino]-phenyl}-acetamidyl
(27)
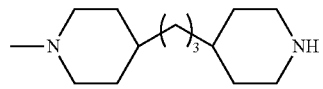
4-(3-piperidin-4-yl-propyl)-piperidin-1-yl
(28)
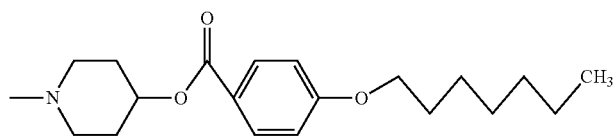
4-(4-hexyloxy-benzoyloxy)-piperidin-1-yl
(29)
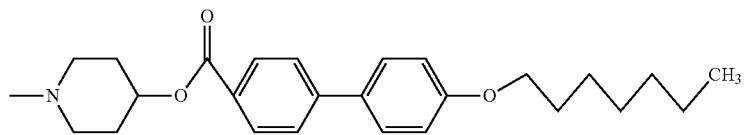
4-(4'-hexyloxy-biphenyl-4-carbonyloxy)-piperidin-1-yl
(30)
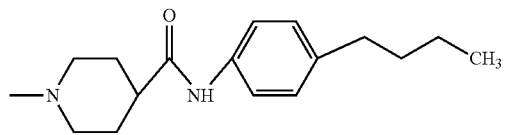
4-(4-butyl-phenylcarbamoyl)-piperidin-1-yl
(31)

-continued

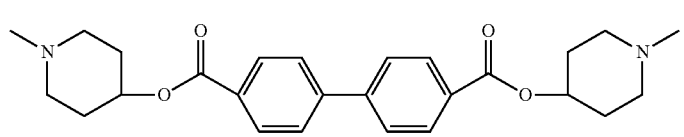

biphenyl-4,4'-dicarboxylic acid bis-[1-
Name of PC Group]-piperidin-4-yl] ester (32)

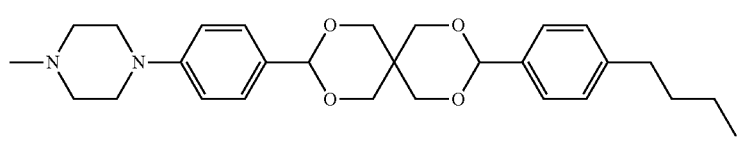

4-(4-(9-(4-butylphenyl)-2,4,8,10-
tetraoxaspiro[5.5]undec-3-
yl)phenyl)piperazin-1-yl (33)

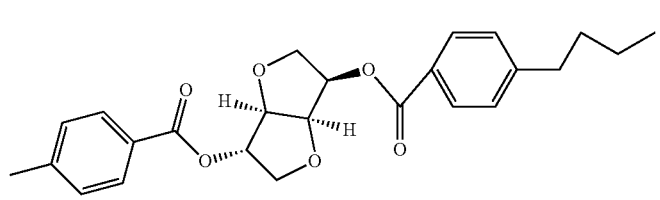

4-(6-(4-butylphenyl)carbonyloxy-(4,8-
dioxabicyclo[3.3.0]oct-2-
yl))oxycarbonyl)pheny (34)

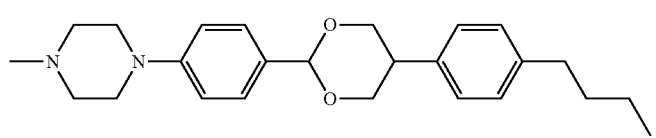

1-{4-[5-(4-butyl-phenyl)-[1,3]dioxan-2-
yl]-phenyl}-4-methyl-piperazin-1-yl (35)

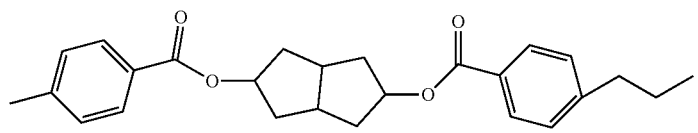

4-(7-(4-
propylphenylcarbonyloxy)bicyclo[3.3.0]oct-2-
yl)oxycarbonyl)phenyl (36)

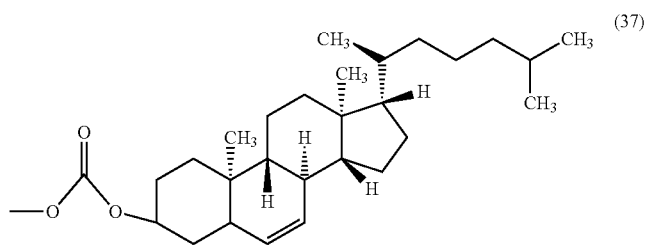

4-[17-(1,5-dimethyl-hexyl)-10,13-
dimethyl-
2,3,4,7,8,9,10,11,12,13,14,15,16,17-
tetradecahydro-1H-
cyclopenta[a]phenanthren-3-
yloxycarbonyloxy (37)

Another non-limiting embodiment disclosed herein provides a photochromic compound of graphic formula I represented by the following graphic formula:

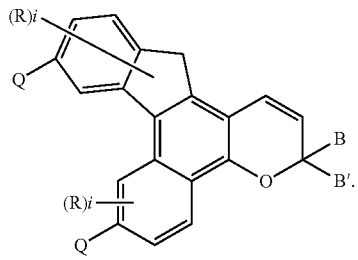

Additionally, according to various non-limiting embodiments disclosed herein, the photochromic compound represented by Formulas I, II, III, IVA, IVB, V and VI may comprise one or more lengthening agents (L). As previously discussed, in L, c, d, e, and f each can be independently chosen from an integer ranging from 1 to 20, inclusive; and d', e' and f' each can be independently chosen from 0, 1, 2, 3, and 4, provided that the sum of d'+e'+f' is at least 1. According to other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f is at least 2. According to still other non-limiting embodiments disclosed herein, c, d, e, and f each can be independently chosen from an integer ranging from 0 to 20, inclusive; and d', e' and f each can be independently chosen from 0, 1, 2, 3, and 4, provided that the sum of d'+e'+f is at least 3. According to still other non-limiting embodiments disclosed herein, c, d, e, and f each can be independently chosen from an integer ranging from 0 to 20, inclusive; and d', e' and f' each can be independently chosen from 0, 1, 2, 3, and 4, provided that the sum of d'+e'+f' is at least 1.

Thus, for example, in Formulas I, II, III, IVA, IVB, V and VI, "i" can be at least 1 and at least one of the R groups can be a lengthening agent L. Additionally or alternatively, the photochromic compound can comprise at least one R group, at least one B group, or at least one B' group that is substituted with a lengthening agent L. For example, although not limiting herein, in one non-limiting embodiment the photochromic compound can comprise a B group comprising a phenyl group that is mono-substituted with a lengthening agent L.

Moreover, although not limiting herein, according to various non-limiting embodiments disclosed herein, the lengthening agent (L) can be attached to a photochromic group (e.g., the pyran group of Formula I, II, III or V) at any available position such that L extends or lengthens the photochromic group in an activated state such that the absorption ratio of the extended photochromic group (i.e., the photochromic compound) is enhanced as compared to the unextended photochromic group. Thus, for example and without limitation, according to various non-limiting embodiments wherein the photochromic compound is represented by Formula I, II, III or V, L can be directly bonded to the pyran group, for example, wherein i is at least 1 and R is L, or it can be indirectly bonded to the pyran group, for example, as a substituent on an R group, B, or B' group such that L extends the pyran group in an activated state such that the absorption ratio of the photochromic compound is enhanced as compared to the unextended pyran group.

Further, the photochromic compound according to various non-limiting embodiments disclosed herein and generally represented by Formula I, II, III, V and VI can have an average absorption ratio of at least 1.5 in an activated state as determined according to CELL METHOD. According to other non-limiting embodiments, the photochromic compound can have an average absorption ratio ranging from 4 to 20, 3 to 30, or 2.5 to 50 in an activated state as determined according to CELL METHOD. According to still other non-limiting embodiments, the photochromic compounds can have an average absorption ratio ranging from 1.5 to 50 in an activated state as determined according to CELL METHOD.

Reaction sequences for forming a photochromic compound according to various non-limiting embodiments disclosed herein having an L group are disclosed in Reaction Sequences A through J, K, M, N, P, Q, T in U.S. Pat. No. 7,342,112, which disclosure is incorporated herein by reference.

Figure 2:
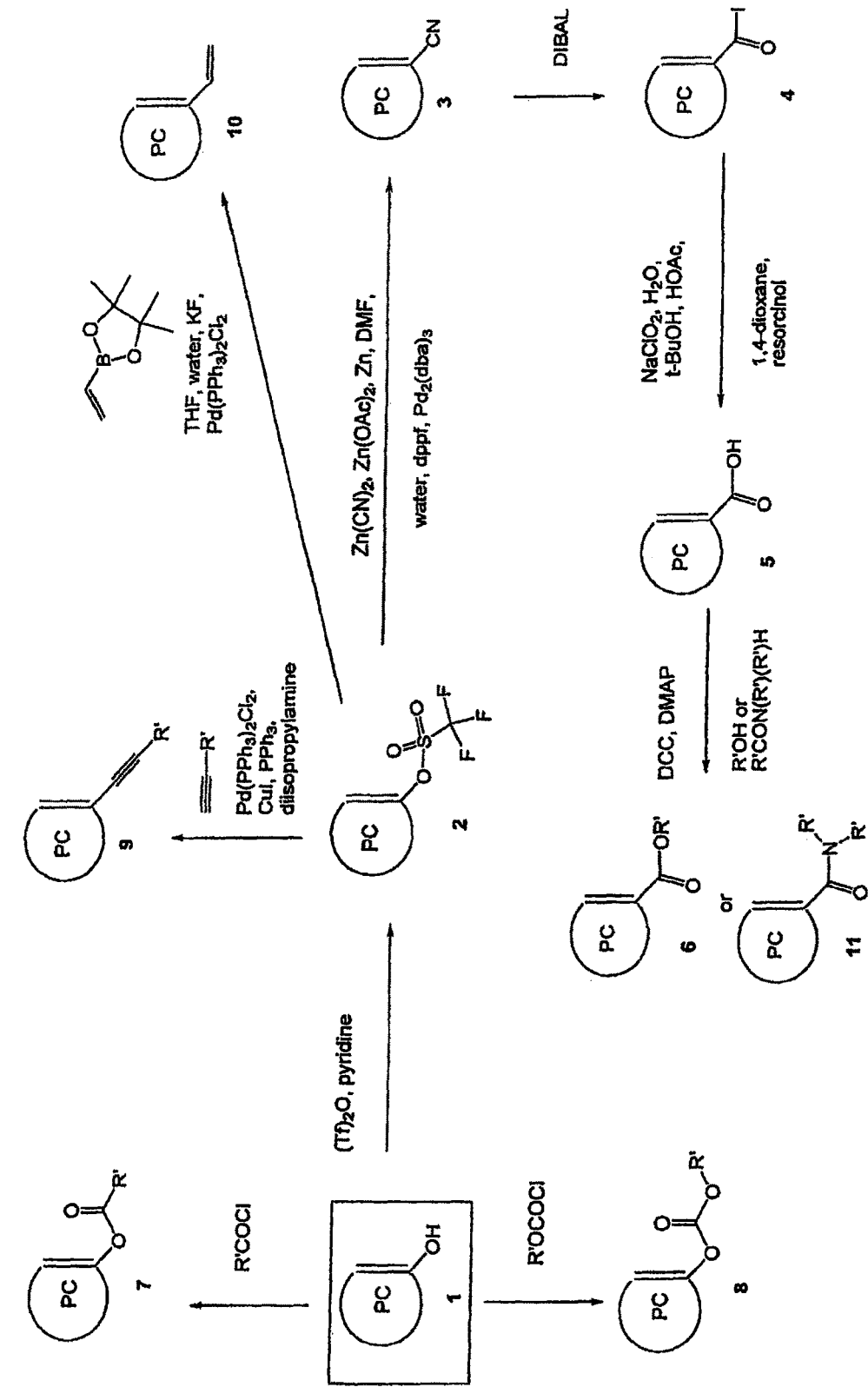
FIG. 2 shows a general reaction scheme for preparing photochromic compounds (PC) having different Q groups according to the present invention.

A general reaction scheme for preparing photochromic compounds represented by Formulas I, II, III, IVA, IVB, V and VI, is shown in FIG. 2. Starting with a photochromic compound having a hydroxyl group shown by Structure #1, or a photochromic compound of Structure #2 having triflate, as shown, or a halogen at the same position, photochromic compounds of Structures #3, 5, 6, 7, 8, 9, 10 and 11 having Q groups of —OSO$_2$R''', —CN, —COOR', —OCOR', OCOOR', —CCR', —C(R')C(R')R' and —CON(R')R', respectively, can be prepared. Examples 1, 2, 3 and 5 were prepared following the general reaction scheme of FIG. 2.

The following abbreviations were used for the chemicals listed in the reaction schemes and examples described hereinafter:

DHP—3,4-dihydro-2H-pyran
DCC—dicyclohexylcarbodiimide
DMAP—4-dimethylaminopyridine
PPTS—pyridine p-toluenesulfonate
pTSA—p-toluenesulfonic acid
NMP—N-methyl pyrrolidone
THF—tetrahyrdofuran
KMnO$_4$—potassium permanganate
MeLi—methyl lithium
ppTs—pyridinium p-toluenesulfonate
(Tf)$_2$O—trifluoromethanesulfonic acid anhydride
Dppf—1,1'-bis(diphenylphosphino)ferrocene
Pd2(dba)3-tris(dibenzylideneacetone)dipalladium(0)
DIBAL—diisobutylaluminium hydride
t-BuOH—t-butanol
HOAc—acetic acid
PdCl$_2$(PPh$_3$)$_2$—bis(triphenylphosphine)palladium(II) chloride
CuI—copper iodide
PPh$_3$—triphenyl phosphine
(iPr)$_2$NH: diisopropyl amine
EtMgBr—ethyl magnesium bromide
Zn(OAc)$_2$—zinc acetate
Zn(CN)$_2$—Zinc cyanide Another general reaction scheme for making Q-substituted naphthols and Q-substituted phenol intermediates for preparing photochromic compounds represented by Formulas I, II, III, IVA, IVB, and V, is shown in FIGS. 3 and 4. Starting with a naphthol or phenol of Structure #12 in FIG. 3, one example of which can be prepared following Steps 1-3 of Example 4, naphthols of Structures #13, 14, 15, 19 and 21 having Q groups of —N$_3$, —CCR', —CR'C(R')R', —COOR', —CON(R')R', respectively, can be prepared. Starting with a naphthol or phenol of Structure #12 in FIG.

4, naphthols of Structures #22, 24, 28, 29 and 30 having Q groups of —CN, —SR', —OSO$_2$R''', —OCOOR', and —OCOR', respectively, can be prepared. The Q-substituted naphthols and Q-substituted phenol intermediates prepared in the reaction schemes of FIGS. 3 and 4 can be used in a coupling reaction with appropriate propargyl alcohols, as known to those skilled in the art, and described for benzopyrans in Reaction C of U.S. Pat. No. 5,429,774 and for naphthopyrans in Reaction E of U.S. Pat. No. 5,458,814 and for indenonaphthopyrans in Reaction G of U.S. Pat. No. 7,262,295, the disclosures of these reactions are incorporated herein by reference. Examples 4, 6 and 7 were prepared following the general reaction schemes of FIGS. 3 and 4.

Another non-limiting embodiment provides a photochromic compound chosen from:
(a) 3-phenyl-3-(4-(4-methoxyphenylpiperazin-1-yl)phenyl)-13,13-dimethyl-6-methoxy-7-trifluoromethanesulfonyloxy-3H,13H-indeno[2',3':3,4]naphtho[1,2-b]pyran;
(b) 3-phenyl-3-(4-(4-methoxyphenylpiperazin-1-yl)phenyl)-13,13-dimethyl-6-methoxy-7-cyano-3H,13H-indeno[2',3':3,4]naphtho[1,2-b]pyran;
(c) 3-phenyl-3-(4-(4-methoxyphenylpiperazin-1-yl)phenyl)-13,13-dimethyl-6-methoxy-7-(2-hydroxy-2-methyl-3-butyn-4-yl)-indeno[2',3':3,4]naphtho[1,2-b]pyran;
(d) 2-phenyl-2-[4-(4-methoxy-phenyl)-piperazin-1-yl]-phenyl-5-methoxycarbonyl-6-methyl-8-cyano-2H-naphtho[1,2-b]pyran;
(e) 2,2-bis(4-methoqphenyl)-5methoxyethylcarbonyl-6-methyl-8-vinyl-2H-naphtho[1,2-b]pyran;
(f) 2,2-bis(4-methoxyphenyl)-5-methoxyethoxycarbonyl-6-methyl-8-hydroxycarbonyl-2H-naphtho[1,2-b]pyran; and
(g) 2,2-bis(4-methoxyphenyl)-5-methoxyethylcarbonyl-6-methyl-8-methoxycarbonyl-2H-naphtho-[1.2-b]pyran.

Also provided by the present invention is a naphthol represented by one of the following graphic formulae:

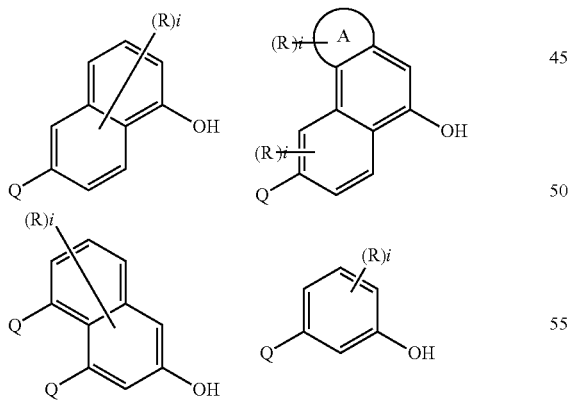

wherein:
(A) each substituent Q independently comprising —N$_3$, —CN, —COOR', —CCR', —C(R')C(R')R', —OCOR', —OCOOR', —SR', —OSO$_2$R''', and/or —CON(R')R', wherein each R' independently comprises hydrogen, an unsubstituted or substituted alkyl group having from 1 to 18 carbon atoms, an unsubstituted or substituted aryl group, an unsubstituted or substituted alkene or alkyne group having from 2 to 18 carbon atoms, wherein said substituents are chosen from halo and hydroxyl and R''' comprises —CF$_3$ or a perfluorinated alkyl group having from 2 to 18 carbon atoms;
(B) each i is an integer chosen from 0 to the total number of available positions and each R is independently chosen for each occurrence from:
(a) hydrogen, $C_1$-$C_{18}$ alkyl, $C_2$-$C_{18}$ alkylidene, $C_2$-$C_{18}$ alkylidyne, vinyl, $C_3$-$C_{10}$ cycloalkyl, $C_1$-$C_{18}$ haloalkyl, allyl, halogen, and benzyl that is unsubstituted or mono-substituted with at least one of $C_1$-$C_{18}$ alkyl and $C_1$-$C_{18}$ alkoxy;
(b) phenyl that is mono-substituted at the para position with at least one substituent chosen from: $C_1$-$C_{18}$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_{18}$ alkyl substituted phenylene, mono- or poly-urethane($C_1$-$C_{20}$)alkylene, mono- or poly-ester($C_1$-$C_{20}$)alkylene, mono- or poly-carbonate(C-$C_{20}$)alkylene, polysilanylene, polysiloxanylene and mixtures thereof, wherein the at least one substituent is connected to an aryl group of a photochromic material;
(c) —CH(CN)$_2$ and —CH(COOX$_1$)$_2$, wherein X$_1$ is chosen from at least one of a lengthening agent L, hydrogen, $C_1$-$C_{18}$ alkyl that is unsubstituted or mono-substituted with phenyl, phenyl($C_1$-$C_{18}$) alkyl that is mono-substituted with $C_1$-$C_{18}$ alkyl, $C_1$-$C_{18}$ haloalkyl, or $C_1$-$C_{18}$ alkoxy, and an aryl group that is unsubstituted, mono- or di-substituted, wherein each aryl substituent is independently chosen from $C_1$-$C_{18}$ alkyl, $C_1$-$C_{18}$ haloalkyl, lengthening agent L and $C_1$-$C_{18}$ alkoxy;
(d) —CH(X$_2$)(X$_3$), wherein:
(i) X$_2$ is chosen from at least one of a lengthening agent L, hydrogen, $C_1$-$C_{18}$ alkyl, and an aryl group that is unsubstituted, mono- or di-substituted, wherein each aryl substituent is independently chosen from $C_1$-$C_{18}$ alkyl and $C_1$-$C_{18}$ alkoxy; and
(ii) X$_3$ is chosen from at least one of —COOX$_1$, —COX$_1$, —COX$_4$, and —CH$_2$OX$_5$,
wherein:
(A) X$_4$ is chosen from at least one of morpholino, piperidino, amino that is unsubstituted, mono- or di-substituted with $C_1$-$C_{18}$ alkyl, and an unsubstituted, mono or di-substituted group chosen from phenylamino and diphenylamino, wherein each substituent is independently chosen from $C_1$-$C_{18}$ alkyl or $C_1$-$C_{18}$ alkoxy; and
(B) X$_5$ is chosen from a lengthening agent L, hydrogen, —C(O)X$_2$, $C_1$-$C_{18}$ alkyl that is unsubstituted or mono-substituted with ($C_1$-$C_{18}$)alkoxy or phenyl, phenyl($C_1$-$C_{18}$)alkyl that is mono-substituted with ($C_1$-$C_{18}$)alkoxy, and an aryl group that is unsubstituted, mono- or di-substituted, wherein each aryl substituent is independently chosen from $C_1$-$C_{18}$ alkyl and $C_1$-$C_{18}$ alkoxy;
(e) an unsubstituted, mono-, di-, or tri-substituted aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl;

wherein each aryl and heteroaromatic substituent is independently chosen for each occurrence from:

(i) a lengthening agent L;

(ii) —COOX$_1$ or —C(O)X$_6$, wherein X$_6$ is chosen from at least one of: a lengthening agent L, hydrogen, C$_1$-C$_{18}$ alkoxy, phenoxy that is unsubstituted, mono- or di-substituted with C$_1$-C$_{18}$ alkyl or C$_1$-C$_{18}$ alkoxy, an aryl group that is unsubstituted, mono- or di-substituted with C$_1$-C$_{18}$ alkyl or C$_1$-C$_{18}$ alkoxy, an amino group that is unsubstituted, mono- or di-substituted with C$_1$-C$_{18}$ alkyl, and a phenylamino group that is unsubstituted, mono- or di-substituted with C$_1$-C$_{18}$ alkyl or C$_1$-C$_{18}$ alkoxy;

(iii) aryl, haloaryl, C$_3$-C$_{10}$ cycloalkylaryl, and an aryl group that is mono- or di-substituted with C$_1$-C$_{18}$ alkyl or C$_1$-C$_{18}$ alkoxy;

(iv) C$_1$-C$_{18}$ alkyl, C$_3$-C$_{10}$ cycloalkyl, C$_3$-C$_{10}$ cycloalkyloxy(C$_1$-C$_{18}$)alkyl, aryl(C$_1$-C$_{18}$)alkyl, aryloxy(C$_1$-C$_{18}$)alkyl, mono- or di-(C$_1$-C$_{18}$)alkylaryl(C$_1$-C$_{18}$)alkyl, mono- or di-(C$_1$-C$_{18}$)alkoxyaryl(C$_1$-C$_{18}$)alkyl, C$_1$-C$_{18}$ haloalkyl, and mono(C$_1$-C$_{18}$)alkoxy(C$_1$-C$_{18}$)alkyl;

(v) C$_1$-C$_{18}$ alkoxy, C$_3$-C$_{10}$ cycloalkoxy; cycloalkyloxy(C$_1$-C$_{18}$)alkoxy, aryl(C$_1$-C$_{18}$) alkoxy, aryloxy(C$_1$-C$_{18}$)alkoxy, mono- or di-(C$_1$-C$_{18}$)alkylaryl(C$_1$-C$_{18}$)alkoxy, and mono- or di-(C$_1$-C$_{18}$)alkoxyaryl(C$_1$-C$_{18}$)alkoxy;

(vi) aminocarbonyl, aminocarbonyl(C$_1$-C$_{18}$)alkylene, amino, mono- or di-(C$_1$-C$_{18}$)alkylamino, diarylamino, piperazino, N—(C$_1$-C$_{18}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;

(vii) —OX$_7$ or —N(X$_7$)$_2$, wherein X$_7$ is chosen from:

(A) a lengthening agent L, hydrogen, C$_1$-C$_{18}$ alkyl, C$_1$-C$_{18}$ acyl, phenyl(C$_1$-C$_{18}$)alkyl, mono(C$_1$-C$_{18}$) alkyl substituted phenyl(C$_1$-C$_{18}$) alkyl, mono(C$_1$-C$_{18}$)alkoxy substituted phenyl(C$_1$-C$_{18}$)alkyl; C$_1$-C$_{18}$ alkoxy(C$_1$-C$_{18}$)alkyl; C$_3$-C$_{10}$ cycloalkyl; mono(C$_1$-C$_{18}$)alkyl substituted C$_3$-C$_{10}$ cycloalkyl, C$_1$-C$_{18}$ haloalkyl, allyl, benzoyl, mono-subsituted benzoyl, naphthoyl or mono-substituted naphthoyl, wherein each of said benzoyl and naphthoyl substituents are independently chosen from C$_1$-C$_{18}$ alkyl, and C$_1$-C$_{18}$ alkoxy;

(B) —CH(X$_8$)X$_9$, wherein X$_8$ is chosen from a lengthening agent L, hydrogen or C$_1$-C$_{18}$ alkyl; and X$_9$ is chosen from a lengthening agent L, —CN, —CF$_3$, or —COOX$_{10}$, wherein X$_{10}$ is chosen from a lengthening agent L, hydrogen or C$_1$-C$_{18}$ alkyl;

(C) —C(O)X$_6$; or (D) tri(C$_1$-C$_{18}$)alkylsilyl, tri(C$_1$-C$_{18}$)alkylsilyloxy, tri(C$_1$-C$_{18}$)alkoxysilyl, tri(C$_1$-C$_{18}$)alkoxysilyloxy, di(C$_1$-C$_{18}$)alkyl(C$_1$-C$_{18}$)alkoxy)silyl, di(C$_1$-C$_{18}$) alkyl(C$_1$-C$_{18}$ alkoxy)silyloxy, di(C$_1$-C$_{18}$)alkoxy (C$_1$-C$_{18}$ alkyl)silyl or di(C$_1$-C$_{18}$)alkoxy(C$_1$-C$_{18}$ alkyl)silyloxy;

(viii) SX$_{11}$, wherein X$_{11}$ is chosen from a lengthening agent L, hydrogen, C$_1$-C$_{18}$ alkyl, C$_1$-C$_{18}$ haloalkyl, an aryl group that is unsubstituted, or mono- or di-substituted with C$_1$-C$_{18}$ alkyl, C$_1$-C$_{18}$ alkoxy, or halogen;

(ix) a nitrogen containing ring represented by Formula i:

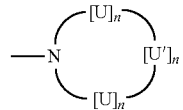

i wherein (A) n is an integer chosen from 0, 1, 2, and 3, provided that if n is 0, U' is U, and each U is independently chosen for each occurrence from —CH$_2$—, —CH(X$_{12}$)—, —C(X$_{12}$)$_2$—, —CH (X$_{13}$)—, —C(X$_{13}$)$_2$—, and —C(X$_{12}$)(X$_{13}$)—, wherein X$_{12}$ is chosen from a lengthening agent L and C$_1$-C$_{18}$ alkyl, and X$_{13}$ is chosen from a lengthening agent L, phenyl and naphthyl, and (B) U' is chosen from U, —O—, —S—, —NH—, —N(X$_{12}$)— or N(X$_{13}$)—, and m is an integer chosen from 1, 2, and 3, and (x) a group represented by Formula ii or iii:

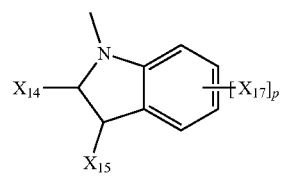

ii

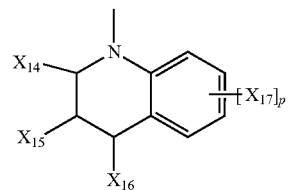

iii wherein X$_{14}$, X$_{15}$, and X$_{16}$ are independently chosen for each occurrence from a lengthening agent L, hydrogen, C$_1$-C$_{18}$ alkyl, phenyl or naphthyl, or X$_{14}$ and X$_{15}$ together form a ring of 5 to 8 carbon atoms; p is an integer chosen from 0, 1, or 2, and X$_{17}$ is independently chosen for each occurrence from a lengthening agent L, C$_1$-C$_{18}$ alkyl, C$_1$-C$_{18}$ alkoxy, or halogen;

(f) an unsubstituted or mono-substituted group chosen from pyrazolyl, imidazolyl, pyrazolinyl, imidazolinyl, pyrrolidinyl, phenothiazinyl, phenoxazinyl, phenazinyl, or acridinyl, wherein each substituent is independently chosen from a lengthening agent L, C$_1$-C$_{18}$ alkyl, C$_1$-C$_{18}$ alkoxy, phenyl, hydroxy, amino or halogen;

(g) a group represented by Formula iv or v:

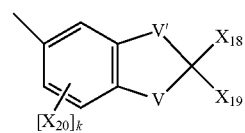

iv

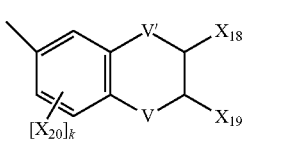

wherein
(i) V' is independently chosen in each formula from —O—, —CH—, $C_1$-$C_6$ alkylene, and $C_3$-$C_{10}$ cycloalkylene,
(ii) V is independently chosen in each formula from —O— or —N($X_{21}$)—, wherein $X_{21}$ is from a lengthening agent L represented by Formula I above, hydrogen, $C_1$-$C_{18}$ alkyl, and $C_2$-$C_{18}$ acyl, provided that if V is —N($X_{21}$)—, V' is —$CH_2$—,
(iii) $X_{18}$ and $X_{19}$ are each independently chosen from a lengthening agent L, hydrogen and $C_1$-$C_{18}$ alkyl, and
(iv) k is chosen from 0, 1, and 2, and each $X_{20}$ is independently chosen for each occurrence from a lengthening agent L, $C_1$-$C_{18}$ alkyl, $C_1$-$C_{18}$ alkoxy, hydroxy and halogen;
(h) a group represented by Formula vi:

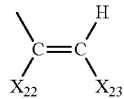

(i) $X_{22}$ is chosen from a lengthening agent L, hydrogen and $C_1$-$C_{18}$ alkyl, and
(ii) $X_{23}$ is chosen from a lengthening agent L and an unsubstituted, mono-, or di-substituted group chosen from aryl, furanyl and thienyl, wherein each substituent is independently chosen for each occurrence from $C_1$-$C_{18}$ alkyl, $C_1$-$C_{18}$ alkoxy, and halogen;
(i) —C(O)$X_{24}$, wherein $X_{24}$ is chosen from a lengthening agent L, hydroxy, $C_1$-$C_{18}$ alkyl, $C_1$-$C_{18}$ haloalkyl, $C_1$-$C_{18}$ alkoxy, phenyl that is unsubstituted or mono-substituted with $C_1$-$C_{18}$ alkyl or $C_1$-$C_{18}$ alkoxy, amino that is unsubstituted, mono- or di-substituted with at least one of $C_1$-$C_{18}$ alkyl, aryl and benzyl;
(j) —COO$X_1$;
(k) —O$X_7$ and —N($X_7$)$_2$;
(l) —S$X_{11}$;
(m) the nitrogen containing ring represented by Formula i;
(n) the group represented by one of Formula ii or iii;
(o) a lengthening agent L represented by:

—[$S_1$]$_c$-[$Q_1$-[$S_2$]$_d$]$_{d'}$-[$Q_2$-[$S_3$]$_e$]$_{e'}$-[$Q_3$-[$S_4$]$_f$]$_{f'}$—$S_5$—P wherein:
(i) each $Q_1$, $Q_2$, and $Q_3$ is independently chosen for each occurrence from: a divalent group chosen from: an unsubstituted or a substituted aromatic group, an unsubstituted or a substituted alicyclic group, an unsubstituted or a substituted heterocyclic group, and mixtures thereof, wherein substituents are chosen from: a group represented by P, liquid crystal meso-gens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$)alkoxy, perfluoro($C_1$-$C_{18}$) alkoxycarbonyl, perfluoro($C_1$-$C_{18}$)alkylcarbonyl, perfluoro($C_1$-$C_{18}$)alkylamino, di-(perfluoro($C_1$-$C_{18}$)alkyl)amino, perfluoro($C_1$-$C_{18}$)alkylthio, $C_1$-$C_{18}$ alkylthio, $C_1$-$C_{18}$ acetyl, $C_3$-$C_{10}$ cycloalkyl, $C_3$-$C_{10}$ cycloalkoxy, a straight-chain or branched $C_1$-$C_{18}$ alkyl group that is mono-substituted with cyano, halo, or $C_1$-$C_{18}$ alkoxy, or poly-substituted with halo, and a group comprising one of the following formulae: -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M;
(ii) c, d, e, and f are each independently chosen from an integer ranging from 0 to 20, inclusive; and each $S_1$, $S_2$, $S_3$, $S_4$, and $S_5$ is independently chosen for each occurrence from a spacer unit chosen from:
(1) —($CH_2$)$_g$—, —($CF_2$)$_h$—, —Si($CH_2$)$_g$—, —(Si[($CH_3$)$_2$]O)$_h$—, wherein g is independently chosen for each occurrence from 1 to 20; h is a whole number from 1 to 16 inclusive;
(2) —N(Z)—, —C(Z)=C(Z)—, —C(Z)=N—, —C(Z')—C(Z')— or a single bond, wherein Z is independently chosen for each occurrence from hydrogen, $C_1$-$C_{18}$ alkyl, $C_3$-$C_{10}$ cycloalkyl and aryl, and Z' is independently chosen for each occurrence from $C_1$-$C_{18}$ alkyl, $C_3$-$C_{10}$ cycloalkyl and aryl; and
(3) —O—, —C(O)—, —C≡C—, —N=N—, —S—, —S(O)—, —S(O)(O)—, —(O)S(O)—, —(O)S(O)O—, —O(O)S(O)O—, or straight-chain or branched $C_1$-$C_{24}$ alkylene residue, said $C_1$-$C_{24}$ alkylene residue being unsubstituted, mono-substituted by cyano or halo, or poly-substituted by halo; provided that when two spacer units comprising heteroatoms are linked together the spacer units are linked so that heteroatoms are not directly linked to each other and when $S_1$ and $S_5$ are linked to PC and P, respectively, they are linked so that two heteroatoms are not directly linked to each other;
(iii) P is chosen from: hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$) alkyl, $C_1$-$C_{18}$alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$) alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$) alkyl, polyethyleneoxy, polypropyleneoxy, ethylenyl, acryloyl, acryloyloxy($C_1$-$C_{18}$)alkylene, methacryloyl, methacryloyloxy($C_{18}$-$C_{18}$)alkyl, 2-chloroacryloyl, 2-phenylacryloyl, acryloyloxyphenyl, 2-chloroacryloylamino, 2-phenylacryloylamino-carbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, or substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl ($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy or mixtures thereof, or P is a structure having from 2 to 4 reactive groups or P is an unsubstituted or substituted ring opening metathesis polymerization precursor; and (iv) d', e' and f are each independently chosen from 0, 1, 2, 3, and 4, provided that a sum of d'+e'+f' is at least 1;

(p) immediately adjacent R groups together form a group represented by Formula vii, viii, or ix:

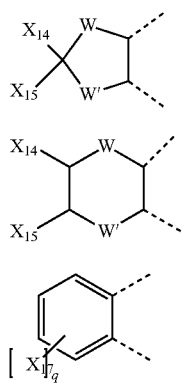

wherein (i) W and W' are independently chosen for each occurrence from —O—, —N($X_7$)—, —C($X_{14}$)—, —C($X_{17}$)—, (ii) $X_{14}$, $X_{15}$ and $X_{17}$ are as set forth above, and (iii) q is an integer chosen from 0, 1, 2, 3, and 4; and (C) the group A represents indeno, thiopheno, benzothiopheno, furo or benzofuro.

In particular embodiments of the present invention, the naphthol may be represented by one of the following graphic formulae:

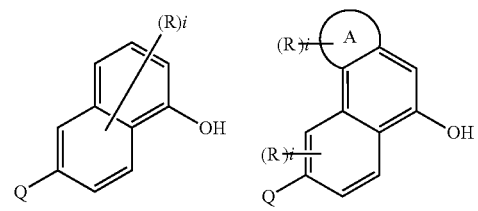

wherein each substituent Q independently comprises —CN, —COOR', —CCR', —C(R')C(R')R', —OCOR', —OCOOR', —SR', —OSO$_2$R''', and/or —CON(R')R', wherein each R' independently comprises an alkyl group having from 1 to 12 carbon atoms and R''' comprises —CF$_3$ or a perfluorinated alkyl group having from 2 to 12 carbon atoms and the group A is indeno.

In another particular embodiment, the naphthol may be represented by the following graphic formula:

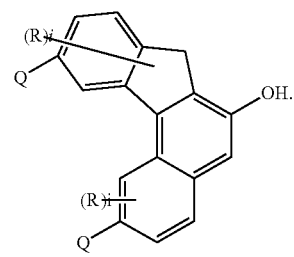

Further reaction schemes for preparing the naphthols of the present invention are described in FIGS. 5 and 6. In both reaction schemes, a group Q' which can be converted into Q is used. Examples of Q' include alkoxy and halogen groups. The conversion of Q' into Q may occur at the naphthol or photochromic compound stage. In Example 4, Q' is converted into Q at the naphthol stage and in Example 1, Q' is converted into Q at the photochromic compound stage. FIG. 5 shows how substituted indeno-fused naphthols are prepared. The synthesis sequence starts from benzophenone of Structure #31, which has the desired substitutions (Q' and R') in place. Such materials are commercially available or prepared by methods known to those skilled in the art. A Stobbe reaction of Structure #31 with dimethyl succinate in the presence of potassium t-butoxide provides condensed product of Structure #32, which easily undergoes a ring closure reaction in acetic anhydride to form the naphthol of Structure #33. The naphthol can be further converted to indeno-fused naphthol of Structure #34 with various substitutions on the bridge carbon via various multistep reactions that can be found in U.S. Pat. Nos. 5,645,767; 5,869,658; 5,698,141; 5,723,072; 5,961,892; 6,113,814; 5,955,520; 6,555,028; 6,296,785; 6,555,028; 6,683,709; 6,660,727; 6,736,998; 7,008,568; 7,166,357; 7,262,295; and 7,320,826, which patents are incorporated herein by reference.

FIG. 6 shows how Q' substituted naphthols are prepared in a similar manner as done in FIG. 5. Starting with the ketone of Structure #35, a Stobbe reaction of Structure #35 with dimethyl succinate in the presence of potassium t-butoxide provides condensed product of Structure #36, which easily undergoes a ring closure reaction in acetic anhydride to form the compound of Structure #37 which is further converted to the naphthol of Structure #38. Naphthols having Q' substituents at various locations can be prepared using procedures known to those skilled in the art.

The thermally reversible photochromic compounds according to various non-limiting embodiments disclosed herein can be used in a variety of applications to provide photochromic and/or photochromic-dichroic properties.

One non-limiting embodiment provides a photochromic article comprising an organic host material and a photochromic composition of the present invention connected to at least a portion of the organic host material. As used herein the term "connected to" means in direct contact with an object or indirect contact with an object through one or more other structures or materials, at least one of which is in direct contact with the object. Further, according to this non-limiting embodiment, the photochromic compound can be connected to at least a portion of the host by incorporation into the host material or by application onto the host material, for example, as part of a coating or layer. In addition to the photochromic compound, the photochromic composition may further comprise at least one additive chosen from dyes, alignment promoters, kinetic enhancing additives, photoinitiators, thermal initiators, polymerization inhibitors, solvents, light stabilizers, heat stabilizers, mold release agents, rheology control agents, leveling agents, free radical scavengers, gelators and adhesion promoters.

Non-limiting examples of organic host materials that may be used in conjunction with various non-limiting embodiments disclosed herein include polymeric materials, for example, homopolymers and copolymers, prepared from the monomers and mixtures of monomers disclosed in U.S. Pat. No. 5,962,617 and in U.S. Pat. No. 5,658,501 from column 15, line 28 to column 16, line 17, the disclosures of which U.S. patents are specifically incorporated herein by reference, an oligomeric material, a monomeric material or a mixture or combination thereof. Polymeric materials can be thermoplastic or thermoset polymeric materials, can be transparent or optically clear, and can have any refractive index required. Non-limiting examples of such disclosed monomers and polymers include: polyol(allyl carbonate) monomers, e.g., allyl diglycol carbonates such as diethylene glycol bis(allyl carbonate), which monomer is sold under the trademark CR-39 by PPG Industries, Inc.; polyurea-polyurethane (polyurea-urethane) polymers, which are prepared, for example, by the reaction of a polyurethane prepolymer and a diamine curing agent, a composition for one such polymer being sold under the trademark TRIVEX by PPG Industries, Inc.; polyol(meth)acryloyl terminated carbonate monomer; diethylene glycol dimethacrylate monomers; ethoxylated phenol methacrylate monomers; diisopropenyl benzene monomers; ethoxylated trimethylol propane triacrylate monomers; ethylene glycol bismethacrylate monomers; poly(ethylene glycol) bismethacrylate monomers; urethane acrylate monomers; poly(ethoxylated bisphenol A dimethacrylate); poly(vinyl acetate); poly(vinyl alcohol); poly(vinyl chloride); poly(vinylidene chloride); polyethylene; polypropylene; polyurethanes; polythiourethanes; thermoplastic polycarbonates, such as the carbonate-linked resin derived from bisphenol A and phosgene, one such material being sold under the trademark LEXAN; polyesters, such as the material sold under the trademark MYLAR; poly(ethylene terephthalate); polyvinyl butyral; poly(methyl methacrylate), such as the material sold under the trademark PLEXIGLAS, and polymers prepared by reacting polyfunctional isocyanates with polythiols or polyepisulfide monomers, either homopolymerized or co-and/or terpolymerized with polythiols, polyisocyanates, polyisothiocyanates and optionally ethylenically unsaturated monomers or halogenated aromatic-containing vinyl monomers. Also contemplated are copolymers of such monomers and blends of the described polymers and copolymers with other polymers, for example, to form block copolymers or interpenetrating network products.

According to one specific non-limiting embodiment, the organic host material is chosen from polyacrylates, polymethacrylates, poly($C_1$-$C_{12}$) alkyl methacrylates, polyoxy(alkylene methacrylates), poly (alkoxylated phenol methacrylates), cellulose acetate, cellulose triacetate, cellulose acetate propionate, cellulose acetate butyrate, poly (vinyl acetate), poly(vinyl alcohol), poly(vinyl chloride), poly(vinylidene chloride), poly(vinylpyrrolidone), poly ((meth)acrylamide), poly(dimethyl acrylamide), poly(hydroxyethyl methacrylate), poly((meth)acrylic acid), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate)monomers, mono-functional acrylate monomers, mono-functional methacrylate monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

According to another specific non-limiting embodiment, the organic host material is a homopolymer or copolymer of monomer(s) chosen from acrylates, methacrylates, methyl methacrylate, ethylene glycol bis methacrylate, ethoxylated bisphenol A dimethacrylate, vinyl acetate, vinylbutyral, urethane, thiourethane, diethylene glycol bis(allyl carbonate), diethylene glycol dimethacrylate, diisopropenyl benzene, and ethoxylated trimethylol propane triacrylate. The polymeric material most often comprises self-assembling materials, polycarbonate, polyamide, polyimide, poly(meth)acrylate, polycyclic alkene, polyurethane, poly(urea)urethane, polythiourethane, polythio(urea)urethane, polyol(allyl carbonate), cellulose acetate, cellulose diacetate, cellulose triacetate, cellulose acetate propionate, cellulose acetate butyrate, polyalkene, polyalkylene-vinyl acetate, poly(vinylacetate), poly(vinyl alcohol), poly(vinyl chloride), poly (vinylformal), poly(vinylacetal), poly(vinylidene chloride), poly(ethylene terephthalate), polyester, polysulfone, polyolefin, copolymers thereof, and/or mixtures thereof.

Further, according to various non-limiting embodiments disclosed herein, the organic host material can form an optical element or portion thereof. Non-limiting examples of optical elements include ophthalmic elements, display elements, windows, and mirrors. As used herein the term "optical" means pertaining to or associated with light and/or vision. For example, although not limiting herein, according to various non-limiting embodiments, the optical element or device can be chosen from ophthalmic elements and devices, display elements and devices, windows, mirrors, packaging material, and active and passive liquid crystal cell elements and devices.

As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors. As used herein the term "display" means the visible or machine-readable representation of information in words, numbers, symbols, designs or drawings. Non-limiting examples of display elements and devices include screens, monitors, and security elements, including without limitation, security marks and authentication marks. As used herein the term "window" means an aperture adapted to permit the transmission of radiation therethrough. Non-limiting examples of windows include automotive and aircraft transparencies, filters, shutters, and optical switches. As used herein the term "mirror" means a surface that specularly reflects a large fraction of incident light.

For example, in one non-limiting embodiment, the organic host material is an ophthalmic element, and more particularly, is an ophthalmic lens.

Further, it is contemplated that the photochromic compounds disclosed herein can be used alone or in conjunction with at least one other complementary organic photochromic compound having at least one activated absorption maxima within the range of 300 nm to 1000 nm, inclusive (or substances containing the same). For example, the photochromic compound disclosed herein can be combined with at least one other conventional organic photochromic compound such that the combination of photochromic compound, when activated, exhibits a desired hue. Non-limiting examples of suitable conventional organic photochromic compounds include those photochromic pyrans, oxazines, and fulgides, set forth above. Other complementary photochromic compounds include, for example, the pyrans, oxazines, fulgides and fulgimides described hereinafter.

Non-limiting examples of thermally reversible complementary photochromic pyrans include benzopyrans, naphthopyrans, e.g., naphtho[1,2-b]pyrans, naphtho[2,1-b]pyrans, indeno-fused naphthopyrans, such as those disclosed in U.S. Pat. No. 5,645,767, and heterocyclic-fused naphthopyrans, such as those disclosed in U.S. Pat. Nos. 5,723,072, 5,698,141, 6,153,126, and 6,022,497, which are hereby incorporated by reference; spiro-9-fluoreno[1,2-b]pyrans; phenanthropyrans; quinopyrans; fluoroanthenopyrans; spiropyrans, e.g., spiro(benzindoline)naphthopyrans, spiro(indoline)benzopyrans, spiro(indoline)naphthopyrans, spiro(indoline)quinopyrans and spiro(indoline)pyrans. More specific examples of naphthopyrans and the complementary organic photochromic substances are described in U.S. Pat. No. 5,658,501, which are hereby specifically incorporated by reference herein. Spiro(indoline)pyrans are also described in the text, *Techniques in Chemistry*, Volume III, "Photochromism", Chapter 3, Glenn H. Brown, Editor, John Wiley and Sons, Inc., New York, 1971, which is hereby incorporated by reference.

Non-limiting examples of thermally reversible complementary photochromic oxazines include benzoxazines, naphthoxazines, and spiro-oxazines, e.g., spiro(indoline)naphthoxazines, spiro(indoline)pyridobenzoxazines, spiro(benzindoline)pyridobenzoxazines, spiro(benzindoline)naphthoxazines, spiro(indoline)benzoxazines, spiro(indoline)fluoranthenoxazine, and spiro(indoline)quinoxazine.

More non-limiting examples of thermally reversible complementary photochromic fulgides include: fulgimides, and the 3-furyl and 3-thienyl fulgides and fulgimides, which are disclosed in U.S. Pat. No. 4,931,220 (which are hereby specifically incorporated by reference) and mixtures of any of the aforementioned photochromic materials/compounds.

For example, it is contemplated that the photochromic compounds disclosed herein can be used alone or in conjunction with another conventional organic photochromic compound (as discussed above), in amounts or ratios such that the organic host material into which the photochromic compounds are incorporated, or onto which the organic host materials are applied, can exhibit a desired color or colors, either in an activated or a "bleached" state. Thus the amount of the photochromic compounds used is not critical provided that a sufficient amount is present to produce a desired photochromic effect. As used herein, the term "photochromic amount" refers to the amount of the photochromic compound necessary to produce the desired photochromic effect.

Another non-limiting embodiment provides a photochromic article comprising a substrate, and an at least partial coating of a coating composition having a photochromic amount of a photochromic compound of the present invention connected to at least a portion of at least one surface thereof of the substrate. Further, although not limiting herein, at least a portion of the at least partial coating can be at least partially set. As used herein the term "set" means to fix in a desired orientation.

For example, according to the above-mentioned non-limiting embodiment, the coating composition can be chosen from, without limitation, polymeric coating compositions, paints, and inks. Further, in addition to the photochromic compounds disclosed herein, the coating compositions according to various non-limiting embodiments can further comprise at least one other conventional organic photochromic compounds having at least one activated absorption maxima within the range of 300 nm to 1000 nm, inclusive.

Non-limiting examples of suitable substrates to which the coating composition comprising the photochromic amount of the photochromic compounds can be applied include glass, masonry, textiles, ceramics, metals, wood, paper and polymeric organic materials. Non-limiting examples of suitable polymeric organic materials are set forth above.

Still other non-limiting embodiments provide optical elements comprising a substrate and an at least partial coating comprising at least one photochromic compound of the present invention connected to at least a portion of the substrate. Non-limiting examples of optical elements include, ophthalmic elements, display elements, windows, and mirrors. For example, according to one non-limiting embodiment, the optical element is an ophthalmic element, and the substrate is an ophthalmic substrate chosen from corrective and non-corrective lenses, partially formed lenses, and lens blanks.

Although not limiting herein, the optical elements according to various non-limiting embodiments disclosed herein can comprise any amount of the photochromic compound necessary to achieve the desired optical properties, such as but not limited to, photochromic properties and dichroic properties.

Other non-limiting examples of substrates that are suitable for use in conjunction with the foregoing non-limiting embodiment include untinted substrates, tinted substrates, photochromic substrates, tinted-photochromic substrates, linearly polarizing substrates, circularly polarizing substrates, elliptically polarizing substrates, and reflective substrates. As used herein with reference to substrates the term "untinted" means substrates that are essentially free of coloring agent additions (such as, but not limited to, conventional dyes) and have an absorption spectrum for visible radiation that does not vary significantly in response to actinic radiation. Further, with reference to substrates the term "tinted" means substrates that have a coloring agent addition (such as, but not limited to, conventional dyes) and an absorption spectrum for visible radiation that does not vary significantly in response to actinic radiation.

As used herein the term "linearly polarizing" with reference to substrates refers to substrates that are adapted to linearly polarize radiation (i.e., confine the vibrations of the electric vector of light waves to one direction). As used herein the term "circularly polarizing" with reference to substrates refers to substrates that are adapted to circularly polarize radiation. As used herein the term "elliptically polarizing" with reference to substrates refers to substrates that are adapted to elliptically polarize radiation. As used herein with the term "photochromic" with reference to substrates refers to substrates having an absorption spectrum for visible radiation that varies in response to at least actinic radiation and is thermally reversible. Further, as used herein with reference to substrates, the term "tinted-photochromic" means substrates containing a coloring agent addition as well as a photochromic compound, and having an absorption spectrum for visible radiation that varies in response to at least actinic radiation and is thermally reversible. Thus for example, in one non-limiting embodiment, the tinted-photochromic substrate can have a first color characteristic of the coloring agent and a second color characteristic of the combination of the coloring agent and the photochromic compound when exposed to actinic radiation.

One specific non-limiting embodiment provides an optical element comprising a substrate and an at least partial coating comprising at least one photochromic compound of the present invention connected to at least a portion of the substrate. Further, according to this non-limiting embodiment, the at least one thermally reversible photochromic compound can be a photochromic-dichroic compound having an average absorption ratio greater than 2.3 in an activated state as determined according to CELL METHOD.

As discussed above, the optical elements according to various non-limiting embodiments disclosed herein can be display elements, such as, but not limited to screens, monitors, and security elements. For example, one non-limiting embodiment provides a display element comprising a first substrate having a first surface, a second substrate having a second surface, wherein the second surface of the second substrate is opposite and spaced apart from the first surface of the first substrate so as to define a gap; and a fluid material comprising at least one photochromic compound of the present invention positioned within the gap defined by the first surface of the first substrate and the second surface of the second substrate. Further, the at least one photochromic compound can be a photochromic-dichroic compound having an average absorption ratio greater than 2.3 in an activated state as determined according to CELL METHOD.

Further, according to this non-limiting embodiment, the first and second substrates can be independently chosen from untinted substrates, tinted substrates, photochromic substrates, tinted-photochromic substrates, linearly polarizing substrates, circularly polarizing substrates, elliptically polarizing substrates and reflective substrates.

Another non-limiting embodiment provides a security element comprising a substrate and at least one photochromic compound of the present invention connected to at least a portion of the substrate. Non-limiting examples of security elements include security marks and authentication marks that are connected to at least a portion of a substrate, such as and without limitation: access cards and passes, e.g., tickets, badges, identification or membership cards, debit cards etc.; negotiable instruments and non-negotiable instruments e.g., drafts, checks, bonds, notes, certificates of deposit, stock certificates, etc.; government documents, e.g., currency, licenses, identification cards, benefit cards, visas, passports, official certificates, deeds etc.; consumer goods, e.g., software, compact discs ("CDs"), digital-video discs ("DVDs"), appliances, consumer electronics, sporting goods, cars, etc.; credit cards; and merchandise tags, labels and packaging.

Although not limiting herein, according to this non-limiting embodiment, the security element can be connected to at least a portion of a substrate chosen from a transparent substrate and a reflective substrate. Alternatively, according to certain non-limiting embodiments wherein a reflective substrate is required, if the substrate is not reflective or sufficiently reflective for the intended application, a reflective material can be first applied to at least a portion of the substrate before the security mark is applied thereto. For example, a reflective aluminum coating can be applied to the at least a portion of the substrate prior to forming the security element thereon. Still further, security element can be connected to at least a portion of a substrate chosen from untinted substrates, tinted substrates, photochromic substrates, tinted-photochromic substrates, linearly polarizing, circularly polarizing substrates, and elliptically polarizing substrates.

Additionally, according to the aforementioned non-limiting embodiment the at least one photochromic compound can be a thermally reversible photochromic-dichroic compound having an average absorption ratio greater than 2.3 in the activated state as determined according to CELL METHOD.

Furthermore, security element according to the aforementioned non-limiting embodiment can further comprise one or more other coatings or sheets to form a multi-layer reflective security element with viewing angle dependent characteristics as described in U.S. Pat. No. 6,641,874, which is hereby specifically incorporated by reference herein.

The photochromic articles and optical elements described above can be formed by methods known in the art. Although not limiting herein, it is contemplated that the photochromic compounds disclosed herein can be connected to a substrate or host by incorporation into the host material or application onto the host or substrate, such as in the form of a coating.

For example, the photochromic-dichroic compound can be incorporated into an organic host material by dissolving or dispersing the photochromic compound within the host material, e.g., casting it in place by adding the photochromic compound to the monomeric host material prior to polymerization, imbibition of the photochromic compound into the host material by immersion of the host material in a hot solution of the photochromic compound or by thermal transfer. As used herein the term "imbibition" includes permeation of the photochromic compound alone into the host material, solvent assisted transfer of the photochromic compound into a porous polymer, vapor phase transfer, and other such transfer methods.

Additionally, the photochromic compound disclosed herein can be applied to the organic host material or other substrate as part of a coating composition (as discussed above) or a sheet comprising the photochromic compound. As used herein the term "coating" means a supported film derived from a flowable composition, which may or may not have a uniform thickness. As used herein the term "sheet" means a pre-formed film having a generally uniform thickness and capable of self-support.

Non-limiting methods of applying coating compositions comprising the photochromic compounds disclosed herein include those methods known in the art for applying coatings, such as, spin coating, spray coating, spray and spin coating, curtain coating, flow coating, dip coating, injection molding, casting, roll coating, wire coating, and overmolding. According to one non-limiting embodiment, a coating comprising the photochromic compound is applied to a mold and the substrate is formed on top of the coating (i.e., overmolding). Additionally or alternatively, a coating composition without the photochromic compound can be first applied to the substrate or organic host material using any of the aforementioned techniques and thereafter imbibed with the photochromic compound as described above.

Non-limiting methods of applying sheets comprising the photochromic compound disclosed herein to a substrate include, for example, at least one of: laminating, fusing, in-mold casting, and adhesively bonding the polymeric sheet to the at least a portion of the substrate. As used herein, the in-mold casting includes a variety of casting techniques, such as but not limited to: overmolding, wherein the sheet is placed in a mold and the substrate is formed (for example by casting) over at least a portion of the substrate; and injection molding, wherein the substrate is formed around the sheet. Further, it is contemplated that the photochromic compound can be applied to the sheet as a coating, incorporated into the sheet by imbibition or by other suitable methods, either prior to applying the sheet to the substrate or thereafter.

Moreover, as discussed above, the photochromic compounds disclosed herein can be incorporated or applied alone, or in combination with at least one other conventional organic photochromic compound, which can also be applied or incorporated into the host materials and substrates as described above. Additional coatings may be applied to the photochromic article including other photochromic coatings, anti-reflective coatings, linearly polarizing coatings, transitional coatings, alignment layers, primer coatings, adhesive coatings, mirrored coatings and protective coatings including antifogging coatings, oxygen barrier coatings and ultraviolet light absorbing coatings.

Various embodiments disclosed herein will now be illustrated in the following non-limiting examples.

EXAMPLES

Part I: Preparation

Example 1

Step 1

2,3-Dimethoxy-7,7-dimethyl-7H-benzo[c]fluoren-5-ol (100.17 grams (g), 0.31 mole (mol)), 2,6-dimethylpiperidine (38.93 g, 0.344 mole), tetrahydrofuran (THF) (400 milliliters (mL)) and toluene (400 mL) were added to a reaction flask equipped with an addition funnel and a condenser. The resulting mixture was stirred. Ethyl magnesium bromide (240 mL of a 3 Molar solution in hexanes) was added slowly with the condenser open to the atmosphere. After the addition, about 300 mL of solvent was removed by distillation and nitrogen was applied through the condenser. The remaining mixture was refluxed for about 16 hours. The mixture was then poured into a beaker containing 3 L of water. The pH was adjusted to about 3 using 12 N hydrochloric acid (HCl). The water was decanted and the resulting oily mixture was dissolved in ethyl acetate, dried over magnesium sulfate and concentrated. Methylene chloride was added to the mixture to crystallize the product. The product was collected by vacuum filtration and dried in a vacuum desiccator yielding 57 grams of off-white crystals. A Nuclear Magnetic Resonance (NMR) spectrum showed that the recovered product had a structure consistent with 7,7-dimethyl-3-methoxy-7H-benzo[c]fluorene-2,5-diol.

Step 2

4-Fluorobenzophenone (44.6 g) and anhydrous dimethyl sulfoxide (DMSO) (200 mL) were added to a reaction flask under nitrogen. 1-(4-methoxyphenyl)-piperazine (94 g) was added, and the suspension was heated to 160° C. After 2 hours, heat was removed, and the mixture was poured into 4 liters of water. The precipitate was collected by vacuum filtration, washed with acetone and dried in vacuum. NMR data showed that the resulting product (81.5 g), recovered as a white solid, had a structure consistent with 4-(4-(4-methoxyphenyl) piperazin-1-yl)benzophenone.

Step 3

The product of Step 2, 4-(4-(4-methoxyphenyl)piperazin-1-yl)benzophenone (80.6 g) and dimethylformamide (DMF) (750 mL, saturated with acetylene) were added to a reaction flask. A sodium acetylide suspension (121 g of a 18 weight percent slurry in toluene, obtained from Aldrich) was added to the mixture with stirring. After 30 minutes, the reaction was poured into a stirred mixture of deionized water (2 L) and hexanes (500 mL). The solid formed was collected by vacuum filtration and dried in vacuum. An NMR spectrum showed that the final product (85 g), an off-white powder, had a structure consistent with 1-phenyl-1-(4-(4-methoxyphenylpiperazin-1-yl)phenyl)-prop-2-yn-1-ol.

Step 4

The product of Step 1, 7,7-dimethyl-3-methoxy-7H-benzo[c]fluorene-2,5-diol (1.93 g, 6.3 millimole (mmole)), and the product of Step 3, 1-phenyl-1-(4-(4-methoxyphenylpiperazin-1-yl)phenyl)-prop-2-yn-1-ol (2.76 g, 6.9 mmole), trimethyl orthoformate (1.47 g, 13.9 mmole), pyridinium p-toluenesulfonate (0.08 g, 0.3 mmole) and chloroform (40 mL) was added to a reaction flask, stirred and refluxed for 6 hours. The resulting product was kept stirring at room temperature (approximately 23° C.) for 12 hours. The solution was then concentrated to a smaller volume until the product started to foam. Methanol, 250 mL was added to precipitate the product. A black solid (4.1 g) was obtained after vacuum filtration. The recovered product was identified by NMR as having a structure consistent with 3-phenyl-3-(4-(4-methoxyphenylpiperazin-1-yl) phenyl)-13,13-dimethyl-6-methoxy-7-hydroxyl-3H, 13H-indeno[2',3':3,4]naphtho[1,2-b]pyran.

Step 5

The product of Step 4, 3-phenyl-3-(4-(4-methoxyphenylpiperazin-1-yl)phenyl)-13,13-dimethyl-6-methoxy-7-hydroxyl-indeno[2',3':3,4]naphtho[1,2-b]pyran (3.1 g, 4.5 mmole), and pyridine (30 mL) at 0° C. were added to a reaction flask and stirred, trifluoromethanesulfonic acid anhydride (1.53 g, 5.4 mmole) was added in one portion. The resulting reaction was stirred for 4 hours at room temperature and then poured into a beaker containing water (500 mL). The precipitated product was collected by vacuum filtration. It was dissolved in chloroform followed by precipitation from methanol. An NMR spectrum showed that the recovered product (3.3 g), a green solid, had a structure consistent with 3-phenyl-3-(4-(4-methoxyphenylpiperazin-1-yl)phenyl)-13,13-dimethyl-6-methoxy-7-trifluoromethanesulfonyloxy-3H,13H-indeno[2',3':3,4] naphtho[1,2-b]pyran.

Example 2

The product of Example 1, 3-phenyl-3-(4-(4-methoxyphenylpiperazin-1-yl)phenyl)-13,13-dimethyl-6-methoxy-7-trifluoromethanesulfonyloxy-3H,13H-indeno[2',3':3,4]naphtho[1,2-b]pyran (11.37 g, 13.9 mmole), zinc cyanide (1.71 g, 14.6 mmole), zinc acetate (0.1 g, 0.56 mmole), zinc (0.036 g, 0.56 mmole), dimethylformamide (DMF) (40 mL), deionized water (0.4 mL), bis(diphenylphosphino)ferrocene (0.02 g, 0.035 mmole) and tris(dibenzylideneacetone) dipalladium (0.013 g, 0.014 mmole) was added to a reaction flask degassed and stirred under the protection of nitrogen. The reaction flask was kept in an oil bath maintained at a temperature of 90-100° C. After 12 hours 1,1'-bis(diphenylphosphino)ferrocene (0.05 g) and tris(dibenzylideneacetone)dipalladium (0.032 g) was added. After 24 more hours, the reaction mixture was diluted with ethyl acetate (300 mL), filtered through Grade 60, 230-400 mesh silica gel available from Fisher Scientific, and concentrated. The resulting product was purified by flash chromatography using ethyl acetate/hexanes with a volume ratio of 1/4. A green solid (5.6 g) was recovered as the product. An NMR spectrum showed that the product had a structure consistent with 3-phenyl-3-(4-(4-methoxyphenylpiperazin-1-yl)phenyl)-13,13-dimethyl-6-methoxy-7-cyano-3H,13H-indeno[2',3':3,4]naphtho[1,2-b]pyran.

Example 3

The product of Example 1, 3-phenyl-3-(4-(4-methoxyphenylpiperazin-1-yl)phenyl)-13,13-dimethyl-6-methoxy-7-trifluoromethanesulfonyloxy-3H,13H-indeno[2',3':3,4]naphtho[1,2-b]pyran (1.71 g, 2.1 mmole), 2-methyl-3-butyn-2-ol (0.26 g, 3.1 mmole), bis(triphenylphosphine)palladium(II) chloride 0.015 g, 0.02 mmole), copper (I) iodide (8 mg, 0.04 mmole), triphenyl phosphine (22 mg, 0.08 mmole) and diisopropyl amine (10 ml) was added to a reaction flask, degassed, protected by dry nitrogen and stirred at 70-80° C. for about 12 hours. The reaction mixture was poured into cold water (100 mL) and the resulting precipitate was collected. The resulting product was then purified by flash chromatography using ethyl acetate/hexanes with a volume ratio of 3/7. A green solid (1.18 g) was recovered as the product. An NMR spectrum showed that the product had a structure consistent with 3-phenyl-3-(4-(4-methoxyphenylpiperazin-1-yl)phenyl)-13,13-dimethyl-6-methoxy-7-(2-hydroxy-2-methyl-3-butyn-4-yl)-indeno[2',3':3,4]naphtho[1,2-b]pyran.

Example 4

Step 1

3'-Bromoacetophenone (200.0 g, 1 mol), dimethyl succinate (190 g, 1.3 mmole) and toluene (800 mL) were added to a 3 L flask and placed on magnetic stir under nitrogen. Potassium t-butoxide (123 g, 1.1 mole) was added over a one hour period. The temperature was controlled to less than 40° C. After one hour, the resulting reaction mixture was poured into 1 L of water and stirred for 15 minutes. The layers were separated, and the aqueous layer was acidified to pH 4 while stirring. Ethyl acetate (500 mL) was added to the stirring mixture, and the layers were separated after 15 minutes. The solvent was removed by rotary evaporator, and the resulting product was isolated as translucent brown oil. The oil was not purified but used directly in the next step.

Step 2

Acetic anhydride (300 ml) was added to a 2 L flask containing the product from Step 1 (220 g, 0.7 mole). The solution was heated to 100° C. under nitrogen. After 4 hours, the resulting reaction was concentrated to brown oil. The oil was dissolved in methylene chloride, washed twice with sodium bicarbonate saturated water, dried over magnesium sulfate and concentrated. The resulting oil was crystallized from ether (34 g crystals were obtained). The remaining crude oil (102 g) was used in next step.

Step 3

Methanol (300 mL) was added to a 1 L flask containing the crude oil from Step 2 (102 g), Concentrated HCl (1 mL) was added and the solution was heated to reflux temperature and maintained there for 4 hours. More of the concentrated HCL (1 mL) was added and the reaction mixture was refluxed another 4 hours. Afterwards, the reaction mixture was concentrated into oil. The crude product was purified by crystallization from acetonitrile and t-butyl methyl ether. A white solid was obtained as the product (40 g), which was identified by NMR as having a structure consistent with 6-bromo-1-hydroxy-4-methyl-3-naphthoic acid methyl ester.

Step 4

A mixture of 6-bromo-1-hydroxy-4-methyl-3-naphthoic acid methyl ester (5 g, 17 mmole), zinc cyanide (2.2 g, 19 mmole), zinc acetate (0.13 g, 0.7 mmole), zinc (0.046 g, 0.7 mmole), DMF (100 mL), water (1 mL), 1,1'-bis(diphenylphosphino)ferrocene (0.047 g, 0.085 mmole) and tris(dibenzylideneacetone)dipalladium (0.031 g, 0.034 mmole) was added to a reaction flask, degassed and stirred under the protection of nitrogen. The reaction mixture was heated to 70° C. After 24 hours, 1,1'-bis(diphenylphosphino)ferrocene (0.5 g) and tris(dibenzylideneacetone)-dipalladium (0.03 g) were added and the reaction was maintained under the same conditions for 15 hours. The resulting suspension was vacuum filtered to remove zinc. The solution was poured into 200 mL water and stirred for 15 minutes. The solid product was collected by vacuum filtration and recrystallized from ethyl acetate The recovered product, 1.1 g of yellow-white crystals, was identified by NMR as having a structure consistent with 6-cyano-1-hydroxy-4-methyl-3-naphthoic acid methyl ester.

Step 5

The product of Step 4, 6-cyano-1-hydroxy-4-methyl-3-naphthoic acid methyl ester (1 g, 4 mmole), the product of Step 3 of Example 1, 1-phenyl-1-(4-(4-methoxyphenylpiperazin-1-yl)phenyl)-prop-2-yn-1-ol (1.9 g, 4.8 mmole), pyridinium p-toluenesulfonate (0.2 g, 0.8 mmole) and chloroform (100 mL) was heated to reflux. After 4 hours, the incomplete reaction mixture was concentrated to an oil and purified by column separation using hexanes:ethyl acetate with a volume ratio of 4:1. The product was further purified by recrystallization from ethyl acetate. A pink-white solid (0.3 g) was obtained as the desired product. The product was confirmed by NMR as having a structure consistent with 2-phenyl-2-[4-(4-Methoxy-phenyl)-piperazin-1-yl]-phenyl-5-methoxycarbonyl-6-methyl-8-cyano-2H-naphtho[1,2-b]pyran.

Example 5

Step 1

Toluene (3.0L) was added under nitrogen to a suitable 16 liter reactor. 3-Bromoacetophenone (600 grams) and dimethyl succinate (512 mL) were added to the reactor. Potassium tert-pentoxide in an approximately 25 weight percent solution in toluene (2,640 mL) was added to the reactor at a rate of approximately 50 mL per minute while keeping the temperature below 35° C. After completion of the addition, the resulting reaction mixture was stirred for 1 to 3 hours until the amount of 3-bromoacetophenone was less than 1 weight percent as determined by High Performance Liquid Chromatography (HPLC). The reaction mixture was cooled to 15° C. and water (4 L) was added. The resulting mixture was warmed to 20-25° C. and stirred for 30 minutes. After phase separation, the bottom aqueous phase was collected. Toluene (1.5 L) was added and stirring continued for 15 minutes. After phase separation, the bottom aqueous phase was collected and methylene chloride (4 L) was added to it. The resulting mixture was maintained at a temperature of 20-25° C. and 6N HCl (850-900 mL) was added while stirring to reduce the pH to approximately 2.0. The resulting mixture was stirred for 20 minutes. After phase separation, the bottom organic phase was collected, washed with water (2 L) and filtered through a plug of 200 grams of silica with a half inch (1.27 cm) thick layer of magnesium sulfate on the top. The plug was rinsed with 1.5 L methylene chloride and then with a 30 weight percent ethyl acetate in methylene chloride mixture until all the product as determined by Thin Layer Chromatography (TLC). The resulting solution was distilled to a volume of 4L and transferred to a 6 L reactor as a crude solution without the isolation of pure product.

Step 2

Xylene (1.8L) was added to the crude solution from Step 1 and the resulting mixture was distilled at 100° C. to remove the methylene chloride. Afterwards, the temperature of the reactor contents was reduced to 60° C. and 4-dimethylamino pyridine (3.6 grams) and acetic anhydride (615 grams) were added to the reactor. The resulting mixture was heated to 120° C. and maintained at that temperature for 24 to 30 hours. After the reaction was completed, the reaction mixture was cooled to 70° C. HCl, 10 weight percent, (150 mL) was added through a dropping funnel while maintaining the reaction mixture temperature below 80° C. The resulting reaction was maintained at 77° C. for 24 to 30 hours. After the reaction was completed, xylene (500 mL) and heptanes (1.2 L) were slowly added to the reaction mixture while it was maintained above 65° C. After the addition, the resulting reaction mixture was cooled to about 20° C. over a period of 3-4 hours. After cooling to 20° C., the reaction mixture was stirred for 6-12 hours for crystallization. The reaction mixture was cooled to 10° C. and the product (crystals) was filtered, washed with 1:1 volume ratio of xylene:heptanes (1-2 L) followed by a wash with heptanes (2-3 L) and dried at 80° C. The resulting product was confirmed by NMR to have a structure consistent with 2-methoxycarbonyl-7-bromo-1-methyl-2-naphth-4-ol.

Step 3

To a suitable reactor was added methanol (2.5 L), 2-methoxycarbonyl-7-bromo-1-methyl-2-naphth-4-ol, the product of Step 2 (250 grams), and water (200 mL). The resulting reaction mixture was stirred while sodium hydroxide, 50 weight percent, 150 mL was added slowly through a dropping funnel and the funnel was washed with water (50 mL). The resulting mixture was maintained at 65° C. with stirring for about 3 hours. After about 3 hours, the temperature of the reaction mixture was increased to 75° C. and methanol (2 L) was distilled off. Water (250 mL) was added to the reaction mixture and the temperature was increased to 80° C. while the distillation was continued. Then the reaction mixture was cooled to 15° C. HCl, 10 weight percent, (1.5 L) was added to the reaction mixture while maintaining the temperature below 25° C. Ethyl acetate (2.5 L) was added followed by HCl, 10 weight percent, (300-400 mL) until a pH of 2.0 was obtained. The lower aqueous layer was separated and discarded. The organic phase was washed with sodium chloride, 10 weight percent, (1 L) and filtered through a small plug of Celite and magnesium sulfate. The filtered organic phase was transferred to a reactor and distilled to a minimum volume. Toluene (1 L) was added and the distillation was continued until the mixture reached 100° C. The resulting mixture was cooled to 15° C., stirred for 2-3 hours and the crystallized product was filtered. The resulting product was washed with 1:1 volume ratio of toluene:heptanes (1 L), followed by a washing with heptanes (1-1.5 L) and dried at 80° C. The resulting product was confirmed by NMR as having a structure consistent with 7-bromo-4-hydroxy-1-methyl-2-naphthoic acid.

Step 4

7-Bromo-4-hydroxy-1-methyl-2-naphthoic acid from Step 3 (20.15 g, 74.35 mmole), 2-methoxy ethanol (200 mL) and p-toluenesulfonic acid (8.00 g, 37.17 mol) were added to a round bottom flask (500 mL) equipped with a Dean-Stark apparatus and stirring bar. The mixture was heated to reflux for 24 h and then cooled to room temperature. The solvent was removed under vacuum to produce an oily residue. The residue was dissolved in ethyl acetate (300 mL) and washed with saturated aqueous sodium bicarbonate three times, each time with 100 mL. The resulting ethyl acetate solution was dried with anhydrous sodium sulfate and concentrated under vacuum to produce a brown solid (17.4 g). NMR analysis of the brown solid indicated that the solid has a structure consistent with 2-methoxyethyl-7-bromo-4-hydroxy-1-methyl-2-naphthoate.

Step 5

1,1-Bis(4-methoxyphenyl)prop-2-yn-1-ol (2.99 g, 11.18 mmole) and p-toulenesulfonic acid (141 mg, 0.74 mmole) were added to a reaction flask containing a chloroform solution of the product from Step 4, 2-methoxyethyl-7-bromo-4-hydroxy-1-methyl-2-naphthoate (2.52 g, 7.46 mmole). The solution was heated to reflux for 4 hours and then the reaction mixture was cooled and the solvent removed under vacuum to produce an oily residue. The residue was purified by column chromatography, using 9:1, based on volume, of a hexane and ethyl acetate mixture as the eluant. Fractions containing the desired product were grouped and concentrated under vacuum to produce an oily residue (3.06 g). NMR analysis of the residue indicated a structure that was consistent with 2,2-bis(4-methoxyphenyl)-5-methoxyethylcarbonyl-6-methyl-8-bromo-2H-naphtho[1,2-13]pyran.

Step 6

To a reaction flask containing 2,2-bis(4-methoxyphenyl)-5-methoxyethylcarbonyl-6-methyl-8-bromo-2H-naphtho[1,2-b]pyran from Step 5 (2.89 g, 4.91 mmole) and vinylboronic acid pinacol ester (1 mL, 5.89 mmole) in a 1:1 mixture of THF (25 mL) and water (25 mL) was added potassium fluoride (4.56 g, 78.62 mmole). The solution was degassed by bubbling nitrogen for 10 min. To the degassed solution bis(triphenylphosphine)palladium(II) chloride (0.34 g, 0.49 mmole) was added. The solution was heated to reflux for 18 h, cooled to room temperature and diluted with ethyl acetate. The mixture was then filtered through a bed of Celite and the filtrate was partitioned with ethyl acetate and water. The ethyl acetate extract was collected, dried with anhydrous sodium sulfate and concentrated under vacuum to produce an oily residue. The residue was purified by column chromatography using 4:1, based on volume, of a hexane and ethyl acetate mixture as the eluant. Fractions that contained the desired product were grouped and concentrated under vacuum to produce a glassy residue (1.98 g). NMR analysis of the residue indicated a structure that was consistent with 2,2-bis(4-methoxyphenyl)-5-methoxyethylcarbonyl-6-methyl-8-vinyl-2H-naphtho[1,2-b]pyran.

Example 6

Step 1

A mixture of the product of Step 1 of Example 5, (17.4 g, 51.5 mmole) and vinylboronic acid pinacol ester (11.0 mL, 61.8 mmole) in 1:1 mixture of THF (250 mL) and water (250 mL) was added potassium fluoride (48.0 g, 824 mmole). The solution was degassed by bubbling nitrogen for 20 min. To the degassed solution bis(triphenylphosphine)palladium(II) chloride (1.81 g, 2.58 mmole) was added. The solution was heated to reflux for 20 h, the reaction mixture was cooled to room temperature and diluted with ethyl acetate. The mixture was then filtered through a bed of Celite and the filtrate was partitioned with ethyl acetate and water. The ethyl acetate extract was collected, dried with anhydrous sodium sulfate and concentrated in vacuo to afford an oily residue. The residue was purified by column chromatography using 4:1 hexane and ethyl acetate mixture as the eluant. Fractions that contained the desired product were grouped and concentrated under vacuum to produce a brown solid (11.5 g). NMR analysis of the brown solid indicated a structure that was consistent with 2-methoxyethyl 7-vinyl-4-hydroxy-1-methyl-2-naphthoate.

Step 2

The product from Step 1, 2-methoxyethyl-7-vinyl-4-hydroxy-1-methyl-2-naphthoate (11.55 g, 40.38 mmole) was added to a reaction flask containing methylene chloride (200 mL) and pyridine (7.00 mL, 80.76 mmole) was added. The mixture was stirred for 5 min. and triisopropylsilyl trifluoromethane sulfonate (16.30 mL, 60.57 mmole) was slowly added. The mixture was stirred for 30 min at room temperature, poured into ice cold water (500 mL) and stirred for 10 min. The mixture was partitioned and the methylene chloride solution was collected, dried with anhydrous sodium sulfate and concentrated under vacuum to produce an oily residue. The residue was purified using a silica plug with a 19:1, volume basis, of a hexane and ethyl acetate mixture. Fractions containing the desired material were grouped and concentrated under vacuum to produce a colorless oil (17.85 g). NMR analysis indicated a structure that was consistent with 2-methoxyethyl-7-vinyl-4-(triisopropylsilyloxy)-1-methyl-2-naphthoate.

Step 3

The product of Step 2, 2-methoxyethyl-7-vinyl-4-(triisopropylsilyloxy)-1-methyl-2-naphthoate (17.85 g, 40.38 mmole) was added to a reaction flask containing t-butanol (121 mL) and water (283 mL) and cooled to 0° C. A solution of potassium permanganate (19.35 g, 122.49 mmole) in water (180 mL) was added slowly to the reaction flask. The pH of the solution was adjusted to 8-10 by the addition of aqueous sodium carbonate. The ice bath was removed and the reaction mixture was warmed to room temperature and stirred for 4 hours. The resulting mixture was filtered through a bed of Celite and the filtrate was carefully acidified to pH 4 by the addition of 10 weight percent aqueous hydrochloric acid. The resulting aqueous solution was extracted with ethyl acetate three times, each time with 300 mL, and the organic layer was collected, dried with anhydrous sodium sulfate, and concentrated under vacuum to produce an oily residue. The oily residue was purified through a silica plug using a 4:1, volume basis, of an ethyl acetate and hexane mixture. Fractions containing the desired material were grouped and concentrated under vacuum to produce a yellow solid (9.14 g). NMR analysis indicated a structure that was consistent with 7-(2-methoxyethoxy)carbonyl)-8-methyl-5-(triisopropylsilyloxy)-2-naphthoic acid.

Step 4

The product of Step 3, 7-((2-methoxyethoxy)carbonyl)-8-methyl-5-(triisopropylsilyloxy)-2-naphthoic acid (1.17 g, 2.54 mmole) was added to a reaction flask containing methylene chloride (10 mL). Methanol (0.09 mL, 2.12 mmole) was added followed by dimethylamino pyridine (0.04 g, 0.33 mmole) and N,N'-dicyclohexylcabodiimide (0.53 g, 2.57 mmole). The mixture was stirred for 1 h at room temperature. The resulting mixture was diluted with methylene chloride and filtered. The filtrate was collected and concentrated under vacuum to produce a yellow solid that was not further purified. The yellow solid was added to a reaction flask containing tetrahydrofuran (10 mL) and water (10 mL). Potassium fluoride (0.35 g, 6.03 mmole) was added and the mixture stirred at room temperature for 20 h. The resulting mixture was extracted with ethyl acetate (100 mL) and partitioned with water. The ethyl acetate extract was collected, dried with anhydrous sodium sulfate, and concentrated under vacuum to produce an oily residue. The residue was dissolved in a minimum amount of methylene chloride and hexanes were added until a precipitate formed. The precipitate (0.61 g) was collected by vacuum filtration and washed with cold hexane. NMR analysis of the precipitate indicated a structure that was consistent with 2-(2-methoxyethyl)-7-methyl-4-hydroxy-1-methylnaphthalene-2,7-dicarboxylate.

Step 5

The product from Step 4, 2-(2-methoxyethyl)-7-methyl-4-hydroxy-1-methylnaphthalene-2,7-dicarboxylate (0.61 g, 1.92 mmole), was added to a reaction flask containing chloroform (20 mL). 1,1-Bis(4-methoxyphenyl)prop-2-yn-1-ol (0.77 g, 2.87 mmole) and p-toluenesulfonic acid (0.04 g, 0.0.21 mmole) were added. The resulting solution was heated to reflux and maintained at reflux temperature for 4 hours. Afterwards, the reaction mixture was cooled and the solvent removed under vacuum to produce an oily residue. The residue was purified by column chromatography and eluted with a 4:1, volume basis, of a hexane and ethyl acetate mixture. Fractions containing the desired product were grouped and concentrated under vacuum to produce an oily residue (0.76 g). NMR analysis of the residue indicated a structure that was consistent with 2,2-bis(4-methoxyphenyl)-5-methoxyethylcarbonyl-6-methyl-8-methoxycarbonyl-2H-naphtho-[1.2-b]pyran.

Example 7

Step 1
To a reaction flask containing the product of Step 5 of Example 6, 5-(2-methoxyethyl)-8-methyl 2,2-bis(4-methoxyphenyl)-6-methyl-2H-naphtho-[1.2-b]pyran-5,8-dicarboxylate (0.56 g, 0.98 mmole) was added tetrahydrofuran (10 mL), methanol (5 mL) and 50 weight percent aqueous sodium hydroxide (3 mL). The mixture was stirred for 30 min. and then poured into a beaker containing 10 weight percent aqueous hydrochloric acid (100 mL) solution. The resulting mixture was extracted with ethyl acetate, three times each time with 100 mL. The ethyl acetate extracts were collected, dried with anhydrous sodium sulfate and concentrated under vacuum to produce an oily residue. The residue was purified using a silica plug eluted with a 19:1, volume basis, ethyl acetate and methanol mixture. The fractions containing the desired product were grouped and concentrated under vacuum to produce foam (0.45 g). NMR analysis of the foam indicated a structure that was consistent with 2,2-bis(4-methoxyphenyl)-5-methoxyethoxycarbonyl-6-methyl-8-hydroxycarbonyl-2H-naphtho[1,2-b]pyran.

Comparative Example 1

A mixture of the product of Example 1, 3-phenyl-3-(4-(4-methoxyphenylpiperazin-1-yl)phenyl)-13,13-dimethyl-6-methoxy-7-trifluoromethanesulfonyloxy-3H, 13H-indeno[2',3':3,4]naphtho[1,2-b]pyran (0.13 g, 0.16 mmol), potassium carbonate (0.054 g, 0.4 mmole), Tetrakistriphenylphosphine palladium (0) (0.018 g, 0.016 mmole), 2-butanol (3 mL) and THF (1 mL) was added to a reaction flask, degassed and stirred under the protection of nitrogen. The reaction mixture was heated to reflux. After 3 hours, reaction mixture was diluted with 100 mL ethyl acetate, washed with water, dried over magnesium sulfate and concentrated. The crude product was purified by flash chromatography (3/7 ethyl acetate/hexanes). The product was further purified by dissolution into methylene chloride followed by precipitation from methanol. A grey solid (0.08 g) was obtained. It was identified by NMR as having a structure consistent with 3-phenyl-3-(4-(4-methoxyphenylpiperazin-1-yl)phenyl)-13,13-dimethyl-6-3H,13H-methoxy-indeno[2',3':3,4]naphtho[1,2-b]pyran.

Comparative Example 2

Step 1
A mixture of the product of Step 3 of Example 6, 74(2-methoxyethoxy)-carbonyl)-8-methyl-5-(triisopropylsilyloxy)-2-naphtoic acid (2.3 g, 7.8 mmole), potassium carbonate (4.4 g, 32 mmole), tetrakistriphenylphosphine palladium (0) (0.52 g, 0.44 mmole), 2-butanol (20 ml) and methanol (10 ml) was added to a reaction flask, degassed and stirred under the protection of nitrogen. The reaction mixture was heated to reflux. After 6 hours, reaction mixture was diluted with 100 ml ethyl acetate, washed with water, dried over magnesium sulfate, filtered through a thin layer of silica gel and concentrated. A brownish glassy solid (1.7 g) was obtained and used directly in the next step. It was identified by NMR as having a structure consistent with 1-hydroxy-4-methyl-3-naphthoic acid methyl ester.

Step 2
A mixture of the product of Step 1, 1-hydroxy-4-methyl-3-naphthoic acid methyl ester (1.6 g, 7.4 mmole), 1-phenyl-1-(4-(4-methoxyphenylpiperazin-1-yl)phenyl)-prop-2-yn-1-ol (2.9 g, 7.4 mmole), p-toluenesulfonic acid (0.14 g, 0.74 mmol) and methylene chloride (30 mL) was stirred and refluxed for 17 hours. Product in the reaction mixture was then separated by flash chromatography (3/7 ethyl acetate/hexanes). The recovered dark red solid was stirred in methanol for 20 hours. A light yellow solid (1.3 g) was obtained as the desired product. The product was confirmed by NMR as having a structure consistent with 2-phenyl-2-[4-(4-Methoxy-phenyl)-piperazin-1-yl]-phenyl-5-methoxycarbonyl-6-methyl-2H-naphtho[1,2-b]pyran.

Comparative Example 3

Step 1
A mixture of the product of Step 5 of Example 5, 2,2-bis(4-methoxyphenyl)-5-methoxyethylcarbonyl-6-methyl-8-methoxycarbonyl-2H-naphtho-[1.2-13]pyran (1.37 g, 2.33 mmole), potassium carbonate (1.29 g, 9.32 mmole), 2-butanol (10 mL) and methanol (10 mL) were added to a round bottom flask (100 mL) and degassed for 10 min. Tetrakistriphenylphosphine palladium (0) (0.13 g, 0.12 mmol) was added and the mixture was heated to reflux under nitrogen. The mixture was maintained at reflux temperature for 4 hours. The resulting mixture was diluted with ethyl acetate, washed with water, dried with anhydrous sodium sulfate and concentrated under vacuum to produce an oily residue. The residue was purified by flash column chromatography using 9:1, volume basis, of a hexane and ethyl acetate mixture as the eluant. Fractions that contained the desired product were grouped and concentrated under vacuum to produce a red oily residue (0.95 g). The product was confirmed by NMR as having a structure consistent with 2,2-bis(4-methoxyphenyl)-5-((2-methoxyethoxy) carbonyl-6-methyl-2H-naphtho[1,2-b]pyran.

Part II: Testing
The photochromic performance of the photochromic materials of Examples 1-7, and Comparative Examples (CE) 1, 2 and 3 were tested using the optical bench set-up described below. Each of the photochromic materials were incorporated into methacrylate test squares as described hereinafter. CE 1 was included for comparison to Examples 1-3 and CE 2 was included for comparison to Example 4 and CE 3 was included for comparison to Examples 5-7.

It will be appreciated by those skilled in the art that the photochromic materials of Examples 1-7 and CE1-3 may be made in accordance with the teachings and examples disclosed herein with appropriate modifications, which will be readily apparent to those skilled in the art upon reading the present disclosure. Further, those skilled in the art will recognize that various modifications to the disclosed methods, as well as other methods, may be used in making the photochromic materials of Examples 1-7 without deviating from the scope of the present disclosure as set forth in the specification and claims herein.

A quantity of the photochromic material to be tested, calculated to yield a $1.5 \times 10^{-3}$ M solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) ("AIBN"). The photochromic material was dissolved into the monomer blend by stirring and gentle heating. After a clear solution was obtained, it was vacuum degassed before being poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, and then lower the temperature to 60° C. for at least 2 hours. After the mold was opened, the polymer sheet was cut using a diamond blade saw into 2 inch (5.1 cm) test squares.

The test squares incorporating the photochromic materials prepared as described above were tested for photochromic response on an optical bench. Prior to testing on the optical bench, the photochromic test squares were exposed to 365 nm ultraviolet light for about 30 minutes to cause the photochromic materials therein to transform from the unactivated ground (or bleached) state to an activated (or colored) state, and then placed in a 75° C. oven for about 15 minutes to allow the photochromic material to revert back to the unactivated state. The test squares were then cooled to room temperature, exposed to fluorescent room lighting for at least 2 hours, and then kept covered (that is, in a dark environment) for at least 2 hours prior to testing on an optical bench maintained at 23° C. The bench was fitted with a 300-watt xenon arc lamp, a remote controlled shutter, a Melles Griot KG2 3 mm filter that modifies the UV and IR wavelengths and acts as a heat-sink, neutral density filter(s), and a sample holder, situated within a 23° C. water bath, in which the square to be tested was inserted. The sample holder and sample were positioned at a small angle (approximately 31°) to the activation beam produced by the 300 Watt xenon arc lamp. A collimated beam of light from a tungsten lamp was passed through the sample square normal to the square and 31° to that activation beam. After passing through the square, the light from the tungsten lamp was directed to a collection (integration) sphere, where the light was blended, and on to an Ocean Optics S2000 spectrometer where the spectrum of the measuring beam was collected and analyzed. The $\lambda_{max-vis}$ is the wavelength in the visible spectrum at which the maximum absorption of the activated (colored) form of the photochromic material in the test square occurs. The $\lambda_{max-vis}$ wavelength was determined by testing the photochromic test squares in a Varian Cary 4000 UV-Visible spectrophotometer.

The saturated optical density ("Sat'd OD") for each test square was determined by opening the shutter from the xenon lamp and measuring the transmittance at $\lambda_{max-vis}$ before and after exposing the test chip to UV radiation for 30 minutes. This Sat'd OD at $\lambda_{max-vis}$ was calculated from the initial and activated spectra measured by the S2000 spectrometer on the optical bench. The Sensitivity is a measure of how quickly the photochromic initially begins to activate and is calculated as 12 times the optical density achieved at 5 seconds of activation. The Fade Rate, as measured by the fade half life (i.e., T½), is the time interval in seconds for the absorbance of the activated form of the photochromic material in the test squares to reach one half of the Sat'd OD absorbance value at room temperature (23° C.), after removal of the source of activating light. The results are recorded in Table 1.

TABLE 1

Photochromic Performance Test Results

| Example Number | $\lambda_{max-vis}$ (nm) | Sensitivity ΔOD/MIN | ΔOD @ Saturation | T½ seconds |
|---|---|---|---|---|
| 1 | 601 | 0.41 | 0.68 | 179 |
| 2 | 631 | 0.67 | 0.70 | 92 |
| 3 | 609 | 0.65 | 1.19 | 252 |
| 4 | 583 | 0.33 | 0.25 | 49 |
| 5 | 507 | 0.26 | 0.36 | 212 |
| 6 | 526 | 0.41 | 0.23 | 28 |
| 7 | 522 | 0.42 | 0.23 | 27 |
| CE-1 | 600 | 0.61 | 1.34 | 358 |
| CE-2 | 542 | 0.31 | 0.77 | 224 |
| CE-3 | 508 | 0.27 | 0.29 | 60 |

It is to be understood that the present description illustrates aspects of the invention relevant to a clear understanding of the invention. Certain aspects of the invention that would be apparent to those of ordinary skill in the art and that, therefore, would not facilitate a better understanding of the invention have not been presented in order to simplify the present description. Although the present invention has been described in connection with certain embodiments, the present invention is not limited to the particular embodiments disclosed, but is intended to cover modifications that are within the spirit and scope of the invention, as defined by the appended claims.

We claim:

1. A photochromic material represented by the following graphic formula:

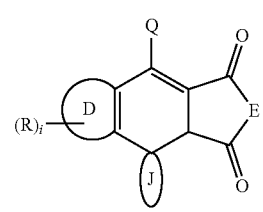

VI wherein:
(A) substituent Q comprises —$N_3$, —CN, —COOR', —CCR', —C(R')C(R')R', —OCOR', —OCOOR', —SR', —$OSO_2R'''$, and/or —CONHR', wherein R' independently comprises hydrogen, an unsubstituted or substituted alkyl group having from 1 to 18 carbon atoms, an unsubstituted or substituted aryl group, an unsubstituted or substituted alkene or alkyne group having from 2 to 18 carbon atoms, wherein said substituents are chosen from halo and hydroxyl and R''' comprises —$CF_3$ or a perfluorinated alkyl group having from 2 to 18 carbon atoms;

(B) i is an integer chosen from 0 to the total number of available positions and each R is independently chosen for each occurrence from:
(a) a group represented by B described hereinafter;
(b) —$C(O)X_{24}$, wherein $X_{24}$ is chosen from a lengthening agent L, hydroxy, $C_1$-$C_{18}$ alkyl, $C_1$-$C_{18}$ alkoxy, phenyl that is unsubstituted or mono-substituted with $C_1$-$C_{18}$ alkyl or $C_1$-$C_{18}$ alkoxy, amino that is unsubstituted, mono- or di-substituted with at least one of $C_1$-$C_{18}$ alkyl, phenyl, benzyl, and naphthyl;
(c) —$OX_7$ and —$N(X_7)_2$; wherein $X_7$ is chosen from:
  (i) a lengthening agent L, hydrogen, $C_1$-$C_{18}$ alkyl, $C_1$-$C_{18}$ acyl, phenyl($C_1$-$C_{18}$)alkyl, mono($C_1$-$C_{18}$)alkyl substituted phenyl($C_1$-$C_{18}$)alkyl, mono($C_1$-$C_{18}$)alkoxy substituted phenyl($C_1$-$C_{18}$)alkyl; $C_1$-$C_{18}$ alkoxy($C_1$-$C_{18}$)alkyl; $C_3$-$C_{10}$ cycloalkyl; mono($C_1$-$C_{18}$)alkyl substituted $C_3$-$C_{10}$ cycloalkyl, $C_1$-$C_{18}$ haloalkyl, allyl, benzoyl, mono-subsituted benzoyl, naphthoyl or mono-substituted naphthoyl, wherein each of said benzoyl and naphthoyl substituents are independently chosen from $C_1$-$C_{18}$ alkyl, and $C_1$-$C_{18}$ alkoxy;
  (ii) —$CH(X_8)X_9$, wherein $X_8$ is chosen from a lengthening agent L, hydrogen or $C_1$-$C_{18}$ alkyl; and $X_9$ is chosen from a lengthening agent L, —CN, —$CF_3$, or —$COOX_{10}$, wherein $X_{10}$ is chosen from a lengthening agent L, hydrogen or $C_1$-$C_{18}$ alkyl;
  (iii) —$C(O)X_6$, wherein $X_6$ is chosen from at least one of: a lengthening agent L, hydrogen, $C_1$-$C_{18}$ alkoxy, phenoxy that is unsubstituted, mono- or di- substituted with $C_1$-$C_{18}$ alkyl or $C_1$-$C_{18}$ alkoxy, an aryl group that is unsubstituted, mono- or di-substituted with $C_1$-$C_{18}$ alkyl or $C_1$-$C_{18}$ alkoxy, an amino group that is unsubstituted, mono- or di-substituted with $C_1$-$C_{18}$ alkyl, and a phenylamino group that is unsubstituted, mono- or di-substituted with $C_1$-$C_{18}$ alkyl or $C_1$-$C_{18}$ alkoxy; or
  (iv) tri($C_1$-$C_{18}$)alkylsilyl, tri($C_1$-$C_{18}$)alkylsilyloxy, tri($C_1$-$C_{18}$)alkoxysilyl, tri($C_1$-$C_{18}$)alkoxysilyloxy, di($C_1$-$C_{18}$)alkyl($C_1$-$C_{18}$ alkoxy)silyl, di($C_1$-$C_{18}$)alkyl($C_1$-$C_{18}$ alkoxy)silyloxy, di($C_1$-$C_{18}$)alkoxy($C_1$-$C_{18}$ alkyl)silyl or di($C_1$-$C_{18}$)alkoxy($C_1$-$C_{18}$ alkyl)silyloxy;
(d) —$SX_{11}$; wherein $X_{11}$ is chosen from a lengthening agent L, hydrogen, $C_1$-$C_{18}$ alkyl, $C_1$-$C_{18}$ haloalkyl, an aryl group that is unsubstituted, or mono- or di-substituted with $C_1$-$C_{18}$ alkyl, $C_1$-$C_{18}$ alkoxy, or halogen;
(e) a nitrogen containing ring represented by Formula i:

i wherein
  (i) n is an integer chosen from 0, 1, 2, and 3, and each U is independently chosen for each occurrence from —$CH_2$—, —$CH(X_{12})$—, —$C(X_{12})_2$—, —$CH(X_{13})$—, —$C(X_{13})_2$—, and —$C(X_{12})(X_{13})$—, wherein $X_{12}$ is chosen from a lengthening agent L and $C_1$-$C_{12}$ alkyl, and $X_{13}$ is chosen from a lengthening agent L, phenyl and naphthyl, and
  (ii) U' is chosen from U, —O—, —S—, —S(O)—, —NH—, —$N(X_{12})$— or —$N(X_{13})$—, and m is an integer chosen from 1, 2, and 3;
(f) the group represented by Formula ii or iii;

ii iii wherein $X_{14}$, $X_{15}$, and $X_{16}$ are independently chosen for each occurrence from a lengthening agent L, hydrogen, $C_1$-$C_{18}$ alkyl, phenyl or naphthyl, or $X_{14}$ and $X_{15}$ together form a ring of 5 to 8 carbon atoms; p is an integer chosen from 0, 1, or 2, and $X_{17}$ is independently chosen for each occurrence from a lengthening agent L, $C_1$-$C_{18}$ alkyl, $C_1$-$C_{18}$ alkoxy, or halogen;
(g) immediately adjacent R groups together form a group represented by Formula vii, viii, or ix:

vii viii ix wherein
  (i) W and W' are independently chosen for each occurrence from —O—, —$N(X_7)$—, —$C(X_{14})$—, and —$C(X_{17})$—;
  (ii) $X_{14}$, $X_{15}$ and $X_{17}$, wherein $X_{14}$, and $X_{15}$ are independently chosen for each occurrence from a lengthening agent L, hydrogen, $C_1$-$C_{18}$ alkyl, phenyl or naphthyl, or $X_{14}$ and $X_{15}$ together form a ring of 5 to 8 carbon atoms; and $X_{17}$ is independently chosen for each occurrence from a lengthening agent L, $C_1$-$C_{18}$ alkyl, $C_1$-$C_{18}$ alkoxy, or halogen; and (iii) q is an integer chosen from 0, 1, 2, 3, and 4; and (h) a lengthening agent L represented by:

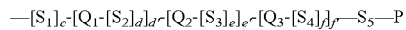

—$[S_1]_c$-$[Q_1$-$[S_2]_d]_{d'}$-$[Q_2$-$[S_3]_e]_{e'}$-$[Q_3$-$[S_4]_f]_{f'}$—$S_5$—P wherein:

(i) each $Q_1$, $Q_2$, and $Q_3$ is independently chosen for each occurrence from: a divalent group chosen from: an unsubstituted or a substituted aromatic group, an unsubstituted or a substituted alicyclic group, an unsubstituted or a substituted heterocyclic group, and mixtures thereof, wherein substituents are chosen from: a group represented by P, liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$)alkoxy, perfluoro ($C_1$-$C_{18}$)alkoxycarbonyl, perfluoro($C_1$-$C_{18}$) alkylcarbonyl, perfluoro($C_1$-$C_{18}$)alkylamino, di-(perfluoro($C_1$-$C_{18}$)alkyl)amino, perfluoro($C_1$-$C_{18}$) alkylthio, $C_1$-$C_{18}$ alkylthio, $C_1$-$C_{18}$ acetyl, $C_3$-$C_{10}$ cycloalkyl, $C_3$-$C_{10}$ cycloalkoxy, a straight-chain or branched $C_1$-$C_{18}$ alkyl group that is mono-substituted with cyano, halo, or $C_1$-$C_{18}$ alkoxy, or poly-substituted with halo, and a group comprising one of the following formulae: -$M(T)_{(t-1)}$ and -$M(OT)_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M;

(ii) c, d, e, and f are each independently chosen from an integer ranging from 0 to 20, inclusive; and each $S_1$, $S_2$, $S_3$, $S_4$, and $S_5$ is independently chosen for each occurrence from a spacer unit chosen from:

(1) —$(CH_2)_g$—, —$(CF_2)_h$—, —$Si(CH_2)_g$—, —$Si[(CH_3)_2]O)_h$—, wherein g is independently chosen for each occurrence from 1 to 20; h is a whole number from 1 to 16 inclusive;

(2) —N(Z)—, —C(Z)=C(Z)—, —C(Z)=N—, —C(Z')—C(Z')— or a single bond, wherein Z is independently chosen for each occurrence from hydrogen, $C_1$-$C_{18}$ alkyl, $C_3$-$C_{10}$ cycloalkyl and aryl, and Z' is independently chosen for each occurrence from $C_1$-$C_{18}$ alkyl, $C_3$-$C_{10}$ cycloalkyl and aryl; and (3) —O—, —C(O)—, —C≡C—, —N=N—, —S—, —S(O)—, —S(O)(O)—, —(O)S(O)—, —(O)S(O)O—, —O(O)S(O)O—, or straight-chain or branched $C_1$-$C_{24}$ alkylene residue, said $C_1$-$C_{24}$ alkylene residue being unsubstituted, mono-substituted by cyano or halo, or poly-substituted by halo; provided that when two spacer units comprising heteroatoms are linked together the spacer units are linked so that heteroatoms are not directly linked to each other and when $S_1$ and $S_5$ are linked to PC and P, respectively, they are linked so that two heteroatoms are not directly linked to each other;

(iii) P is chosen from: hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, amino carbonyl($C_1$-$C_{18}$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy ($C_1$-$C_{18}$)alkyl, polyethyleneoxy, polypropyleneoxy, ethyl enyl, acryloyl, acryloyloxy($C_1$-$C_{18}$)alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato ($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, or substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl ($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy or mixtures thereof, or P is a structure having from 2 to 4 reactive groups or P is an unsubstituted or substituted ring opening metathesis polymerization precursor; and (iv) d', e' and f' are each independently chosen from 0, 1, 2, 3, and 4, provided that a sum of d' +e' +f' is at least 1;

(C) each B is independently chosen from:

(i) hydrogen, $C_1$-$C_{18}$ alkyl, $C_2$-$C_{18}$ alkylidene, $C_2$-$C_{18}$ alkylidyne, vinyl, $C_3$-$C_{10}$ cycloalkyl, $C_1$-$C_{18}$ haloalkyl, allyl, halogen, and benzyl that is unsubstituted or mono-substituted with at least one of $C_1$-$C_{18}$ alkyl and $C_1$-$C_{18}$ alkoxy;

(ii) phenyl that is mono-substituted at the para position with at least one substituent chosen from: $C_1$-$C_{18}$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_{18}$ alkyl substituted phenylene, mono- or polyurethane($C_1$-$C_{20}$)alkylene, mono- or poly-ester($C_1$-$C_{20}$)alkylene, mono-or poly-carbonate($C_1$-$C_{20}$)alkylene, polysilanylene, polysiloxanylene and mixtures thereof wherein the at least one substituent is connected to an aryl group of a photochromic material;

(iii) —$CH(CN)_2$ and —$CH(COOX_1)_2$, wherein $X_1$ is chosen from at least one of a lengthening agent L, hydrogen, $C_1$-$C_{18}$ alkyl that is unsubstituted or mono-substituted with phenyl, phenyl($C_1$-$C_{18}$)alkyl that is mono-substituted with $C_1$-$C_{18}$ alkyl, $C_1$-$C_{18}$ haloalkyl or $C_1$-$C_{18}$ alkoxy, and an aryl group that is unsubstituted, mono- or di-substituted, wherein each aryl substituent is independently chosen from $C_1$-$C_{18}$ alkyl and $C_1$-$C_{18}$ alkoxy; and lengthening agent L;
(iv) —CH($X_2$)($X_3$), wherein:
  (I) $X_2$ is chosen from at least one of a lengthening agent L, hydrogen, $C_1$-$C_{18}$ alkyl, and an aryl group that is unsubstituted, mono-or di-substituted, wherein each aryl substituent is independently chosen from $C_1$-$C_{18}$ alkyl and $C_1$-$C_{18}$ alkoxy; and
  (2) $X_3$ is chosen from at least one of —COO$X_1$, —CO$X_1$, —CO$X_4$, and —CH$_2$O$X_5$, wherein: $X_4$ is chosen from at least one of morpholino, piperidino, amino that is unsubstituted, mono- or di-substituted with $C_1$-$C_{18}$ alkyl, and an unsubstituted, mono or di- substituted group chosen from phenylamino and diphenylamino, wherein each substituent is independently chosen from $C_1$-$C_{18}$ alkyl or $C_1$-$C_{18}$ alkoxy;
  and $X_5$ is chosen from a lengthening agent L, hydrogen, —C(O)$X_2$, $C_1$-$C_{18}$ alkyl that is unsubstituted or mono-substituted with ($C_1$-$C_{18}$)alkoxy or phenyl, phenyl($C_1$-$C_{18}$)alkyl that is mono-substituted with ($C_1$-$C_{18}$)alkoxy, and an aryl group that is unsubstituted, mono- or di-substituted, wherein each aryl substituent is independently chosen from $C_1$-$C_{18}$ alkyl and $C_1$-$C_{18}$ alkoxy;
(v) an unsubstituted, mono-, di-, or tri- substituted aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, or fluorenyl; wherein each aryl and heteroaromatic group substituent is independently chosen for each occurrence from:
  (1) a lengthening agent L;
  (2) —COO$X_1$ or —C(O)$X_6$;
  (3) aryl, haloaryl, $C_3$-$C_{10}$ cycloalkylaryl, and an aryl group that is mono- or di-substituted with $C_1$-$C_{18}$ alkyl or $C_1$-$C_{18}$ alkoxy;
  (4) $C_1$-$C_{18}$ alkyl, $C_3$-$C_{10}$ cycloalkyl, $C_3$-$C_{10}$ cycloalkyloxy($C_1$-$C_{18}$)alkyl, aryl($C_1$-$C_{18}$)alkyl, aryloxy($C_1$-$C_{18}$)alkyl, mono- or di- ($C_1$-$C_{18}$)alkylaryl($C_1$-$C_{18}$)alkyl, mono- or di- ($C_1$-$C_{18}$)alkoxyaryl($C_1$-$C_{18}$)alkyl, $C_1$-$C_{18}$ haloalkyl, and mono ($C_1$-$C_{18}$)alkoxy($C_1$-$C_{18}$)alkyl;
  (5) $C_1$-$C_{18}$ alkoxy, $C_3$-$C_{10}$ cycloalkoxy, cycloalkyloxy($C_1$-$C_{18}$)alkoxy, aryl($C_1$-$C_{18}$)alkoxy, aryloxy($C_1$-$C_{18}$)alkoxy, mono- or di- ($C_1$-$C_{18}$)alkylaryl($C_1$-$C_{18}$)alkoxy, and mono- or di- ($C_1$-$C_{18}$)alkoxyaryl($C_1$-$C_{18}$)alkoxy;
  (6) aminocarbonyl, aminocarbonyl($C_1$-$C_{18}$)alkylene, amino, mono- or di-alkylamino, diarylamino, piperazino, N-($C_1$-$C_{18}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;
  (7) —OXO or —N($X_7$)$_2$;
  (8) —S$X_{11}$;
  (9) a nitrogen containing ring represented by Formula i;
  (10) a group represented by Formula ii or iii;
  (11) an unsubstituted or mono-substituted group chosen from pyrazolyl, imidazolyl, pyrazolinyl, imidazolinyl, pyrrolidinyl, phenothiazinyl, phenoxazinyl, phenazinyl, or acridinyl, wherein each substituent is independently chosen from a lengthening agent L, $C_1$-$C_{18}$ alkyl, $C_1$-$C_{18}$ alkoxy, phenyl, hydroxy, amino or halogen;
  (12) a group represented by Formula iv or v:

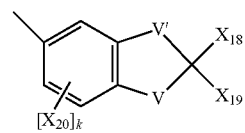

iv

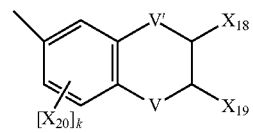

v wherein:
  (I) V' is independently chosen in each formula from —O—, —CH—, $C_1$-$C_6$ alkylene, and $C_3$-$C_{10}$ cycloalkylene,
  (II) V is independently chosen in each formula from —O— or —N($X_{21}$)—, wherein $X_{21}$ is a lengthening agent L, hydrogen, $C_1$-$C_{18}$ alkyl, and $C_2$-$C_{18}$ acyl, provided that if V is —N($X_{21}$)—, V' is —CH$_2$—,
  (III) $X_{18}$ and $X_{19}$ are each independently chosen from a lengthening agent L, hydrogen and $C_1$-$C_{18}$ alkyl, and
  (IV) k is chosen from 0, 1, and 2, and each $X_{20}$ is independently chosen for each occurrence from a lengthening agent L, $C_1$-$C_{18}$ alkyl, $C_1$-$C_{18}$ alkoxy, hydroxy and halogen; or
  (13) a group represented by Formula vi:

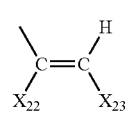

vi wherein
  (I) $X_{22}$ is chosen from a lengthening agent L, hydrogen and $C_1$-$C_{18}$ alkyl, and
  (II) $X_{23}$ is chosen from a lengthening agent L and an unsubstituted, mono-, or di-substituted group chosen from naphthyl, phenyl, furanyl and thienyl, wherein each substituent is independently chosen for each occurrence from $C_1$-$C_{18}$ alkyl, $C_1$-$C_{18}$ alkoxy, and halogen;
(D) provided that when said photochromic material is represented by graphic formula VI, Q comprises: —N$_3$, —CN, —CCR', or —OSO$_2$R'''; E is —O— or —N(Q)-; and D is represented by the following graphic formula:

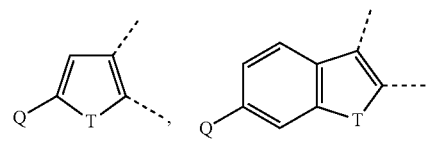

wherein: T is —S—, —O— or —N(R)—, J is a spiro-alicyclic ring and Q is the same as described hereinbefore.

2. A photochromic composition comprising the photochromic material of claim 1 incorporated into at least a portion of an organic material, said organic material being a polymeric material, an oligomeric material, a monomeric material or a mixture or combination thereof.

3. The photochromic composition of claim 2, wherein said polymeric material comprises self-assembling materials, polycarbonate, polyamide, polyimide, poly(meth)acrylate, polycyclic alkene, polyurethane, poly(urea)urethane, polythiourethane, polythio(urea)urethane, polyol(allyl carbonate), cellulose acetate, cellulose diacetate, cellulose triacetate, cellulose acetate propionate, cellulose acetate butyrate, polyalkene, polyalkylene-vinyl acetate, poly(vinylacetate), poly(vinyl alcohol), poly(vinyl chloride), poly(vinylformal), poly(vinylacetal), poly(vinylidene chloride), poly(ethylene terephthalate), polyester, polysulfone, polyolefin, copolymers thereof, and/or mixtures thereof.

4. The photochromic composition of claim 2, wherein the photochromic composition further comprises at least one additive chosen from dyes, alignment promoters, kinetic enhancing additives, photoinitiators, thermal initiators, polymerization inhibitors, solvents, light stabilizers, heat stabilizers, mold release agents, rheology control agents, leveling agents, free radical scavengers, gelators and adhesion promoters.

5. The photochromic composition of claim 2, comprising a coating composition chosen from self-assembling materials and film forming materials.

6. A photochromic article comprising a substrate and a photochromic material according to claim 1 connected to at least a portion of a substrate.

7. The photochromic article of claim 6, comprising an optical element, said optical element being at least one of an ophthalmic element, a display element, a window, a mirror, packaging material and an active or passive liquid crystal cell element.

8. The photochromic article of claim 7, wherein the ophthalmic element comprises corrective lenses, non-corrective lenses, contact lenses, intra-ocular lenses, magnifying lenses, protective lenses, or visors.

9. The photochromic article of claim 7, wherein the display element comprises screens, monitors and security elements.

10. The photochromic article of claim 6, wherein the substrate comprises a polymeric material and the photochromic material is incorporated into at least a portion of the polymeric material.

11. The photochromic article of claim 10, wherein the photochromic material is blended with at least a portion of the polymeric material, bonded to at least a portion of the polymeric material, and/or imbibed into at least a portion of the polymeric material.

12. The photochromic article of claim 6, wherein the photochromic article comprises a coating or film connected to at least a portion of the substrate, said coating or film comprising the photochromic material.

13. The photochromic article of claim 12, wherein said substrate is formed from organic materials, inorganic materials, or combinations thereof.

14. The photochromic article of claim 11, further comprising at least one additional at least partial coating chosen from photochromic coatings, anti-reflective coatings, linearly polarizing coatings, transitional coatings, alignment layers, primer coatings, adhesive coatings, mirrored coatings and protective coatings including antifogging coatings, oxygen barrier coatings and ultraviolet light absorbing coatings.

* * * * *

UNITED STATES PATENT AND TRADEMARK OFFICE
CERTIFICATE OF CORRECTION

PATENT NO. : 10,501,446 B2
APPLICATION NO. : 16/007067
DATED : December 10, 2019
INVENTOR(S) : Meng He et al.

It is certified that error appears in the above-identified patent and that said Letters Patent is hereby corrected as shown below:

On the Title Page

Item [57], Line 12, after "atoms" insert -- . --

In the Specification

Column 1, Line 7, delete "No" and insert -- No. --

In the Claims

Column 59, Line 23, Claim 1, delete "subsituted" and insert -- substituted --

Column 59, Line 47, Claim 1, delete "C $_{18}$" and insert -- $C_{18}$ --

Column 61, Line 17, Claim 1, delete "C $_{18}$" and insert -- $C_{18}$ --

Column 61, Lines 20-21, Claim 1, "perfluoro ($C_1$-$C_{18}$)" and insert -- perfluoro($C_1$-$C_{18}$) --

Column 61, Line 29, Claim 1, delete "-M(T)$_{(t-1)}$and" and insert -- -M(T)$_{(t-1)}$ and --

Column 62, Line 7, Claim 1, delete "amino carbonyl($C_1$ -$C_{18}$)" and insert -- aminocarbonyl($C_1$-$C_{18}$) --

Column 62, Line 9, Claim 1, delete "($C_1$-C $_{18}$)" and insert -- ($C_1$-$C_{18}$) --

Column 62, Line 11, Claim 1, delete "($C_1$- $C_{18}$)" and insert -- ($C_1$-$C_{18}$) --

Column 62, Line 14, Claim 1, delete "($C_1$-C $_{18}$)" and insert -- ($C_1$-$C_{18}$) --

Column 62, Line 15, Claim 1, delete "ethyl enyl," and insert -- ethylenyl, --

Signed and Sealed this
Fifth Day of October, 2021

Drew Hirshfeld
*Performing the Functions and Duties of the
Under Secretary of Commerce for Intellectual Property and
Director of the United States Patent and Trademark Office*

Column 62, Line 43, Claim 1, delete "+e′ +f′" and insert -- + e′ + f′ --

Column 62, Line 59, Claim 1, after "thereof" insert -- , --

Column 62, Line 64, Claim 1, delete "C $_{18}$" and insert -- $C_{18}$ --

Column 63, Line 8, Claim 1, delete "$C_1$ -$C_{18}$" and insert -- $C_1$-$C_{18}$ --

Column 63, Line 8, Claim 1, delete "$C_1$ -$C_{18}$" and insert -- $C_1$-$C_{18}$ --

Column 63, Line 58, Claim 1, delete "--OXO" and insert -- --$OX_7$ --

Column 64, Line 21, Claim 1, delete "$C_1$- $C_6$" and insert -- $C_1$-$C_6$ --